US011672774B2

(12) United States Patent
Burrows et al.

(10) Patent No.: US 11,672,774 B2
(45) Date of Patent: Jun. 13, 2023

(54) METHODS OF TREATING SQUAMOUS CELL CARCINOMAS WITH FARNESYLTRANSFERASE INHIBITORS

(71) Applicant: Kura Oncology, Inc., San Diego, CA (US)

(72) Inventors: Francis Burrows, Solana Beach, CA (US); Yi Liu, San Diego, CA (US)

(73) Assignee: Kura Oncology, Inc., San Diego, CA (US)

( * ) Notice: Subject to any disclaimer, the term of this patent is extended or adjusted under 35 U.S.C. 154(b) by 0 days.

(21) Appl. No.: 17/488,194

(22) Filed: Sep. 28, 2021

(65) Prior Publication Data

US 2022/0117927 A1    Apr. 21, 2022

Related U.S. Application Data

(63) Continuation of application No. PCT/US2020/025149, filed on Mar. 27, 2020.

(60) Provisional application No. 62/992,749, filed on Mar. 20, 2020, provisional application No. 62/826,771, filed on Mar. 29, 2019.

(51) Int. Cl.

| | | |
|---|---|---|
| *A61K 31/223* | (2006.01) | |
| *A61P 35/00* | (2006.01) | |
| *A61K 33/243* | (2019.01) | |
| *A61K 31/045* | (2006.01) | |
| *A61K 31/365* | (2006.01) | |
| *A61K 31/4155* | (2006.01) | |
| *A61K 31/4439* | (2006.01) | |
| *A61K 31/4545* | (2006.01) | |
| *A61K 31/4709* | (2006.01) | |
| *A61K 31/496* | (2006.01) | |
| *A61K 31/519* | (2006.01) | |
| *A61K 31/55* | (2006.01) | |
| *A61K 31/5513* | (2006.01) | |
| *A61K 39/395* | (2006.01) | |
| *A61K 45/06* | (2006.01) | |

(52) U.S. Cl.
CPC .......... *A61K 31/223* (2013.01); *A61K 31/045* (2013.01); *A61K 31/365* (2013.01); *A61K 31/4155* (2013.01); *A61K 31/4439* (2013.01); *A61K 31/4545* (2013.01); *A61K 31/4709* (2013.01); *A61K 31/496* (2013.01); *A61K 31/519* (2013.01); *A61K 31/55* (2013.01); *A61K 31/5513* (2013.01); *A61K 33/243* (2019.01); *A61K 39/3955* (2013.01); *A61K 45/06* (2013.01); *A61P 35/00* (2018.01)

(58) Field of Classification Search
CPC .. A61K 31/223; A61K 31/045; A61K 31/365; A61K 31/4155; A61K 31/4439; A61K 31/4545; A61K 31/4709; A61K 31/496; A61K 31/519; A61K 31/55; A61K 31/5513; A61K 33/243; A61K 39/3955; A61K 45/06; A61P 35/00
See application file for complete search history.

(56) References Cited

U.S. PATENT DOCUMENTS

| | | | |
|---|---|---|---|
| 2017/0051356 A1* | 2/2017 | Gualberto | ............... A61P 35/00 |
| 2018/0187266 A1 | 7/2018 | Gualberto | |

OTHER PUBLICATIONS

Klauss et al. (Journal of Clinical Oncology 24, No. 18_suppl (Jun. 20, 2006) 5581-5581).*
Keam et al. (Anticancer Research 35: 175-182 (2015)).*
Ho, Alan et al., "Preliminary results from a phase 2 trial of tipifamib in HRAS mutant Head & Neck Squamous Cell Carcinomas (HNSCCs)," retrieved online from https://https://kuraoncology.com/wp-content/uploads/KO-TIP-001-HN-Scottsdale-Poster-44-in-by-40-in-v2018-02-12-FINAL.pdf, retrieved on Apr. 3, 2020.
Oh, S-H et al., "Identification of insulin-like growth factor binding protein-3 as a farnesyl transferase inhibitor SCH66336-induced negative regulator of angiogenesis in head and neck squamous cell carcinoma," Clin. Cancer Res., 12(2):653-661 (2006).
Saba, N. F. et al., "Effect of the combined treatment with tipifamib and cetuximab on EGFR and RAS related signaling pathways in H-RAS wild type squamous cell carcinoma of the head and neck (HNSCC)," International Jounal of Radiation, 106(5):1187 (2020).
International Search Report and Written Opinion, dated Jul. 13, 2020 for PCT/US2020/025149.
Pylayeva-Gupta et al., "RAS oncogenes: weaving a tumorigenic web," Nat Rev Cancer, 11(11):761-774 (2013).

* cited by examiner

*Primary Examiner* — Robert H Havlin
(74) *Attorney, Agent, or Firm* — Jones Day

(57) ABSTRACT

The present invention relates to the field of cancer therapy. Specifically, provided are methods of treating Squamous Cell Carcinoma in a subject with a farnesyltransferase inhibitor (FTI) that include determining whether the subject is likely to be responsive to the FTI treatment based on the expression level of H-Ras.

50 Claims, 24 Drawing Sheets

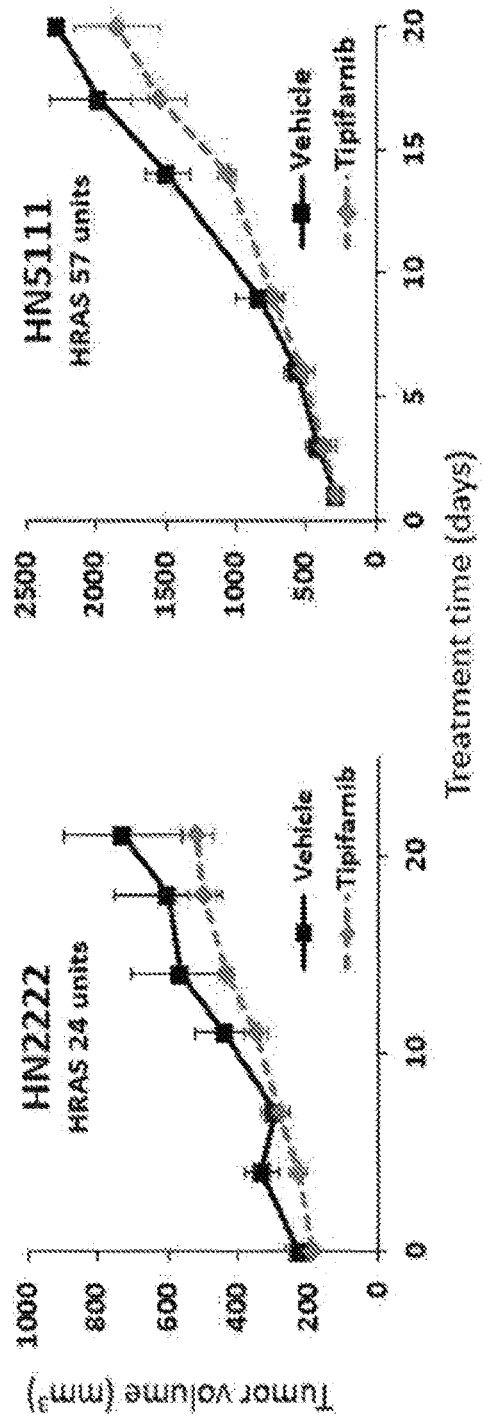
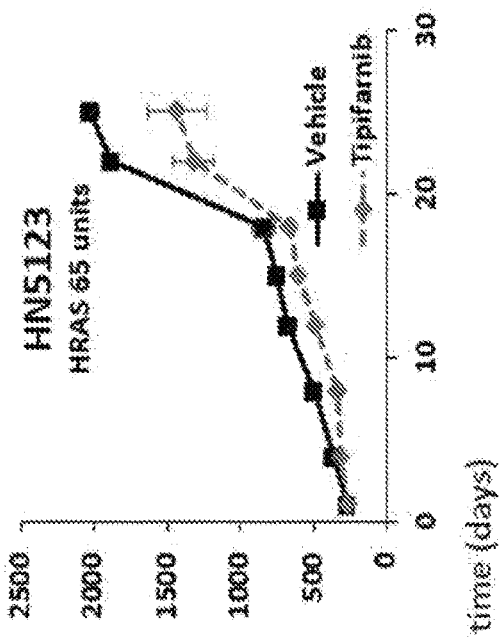
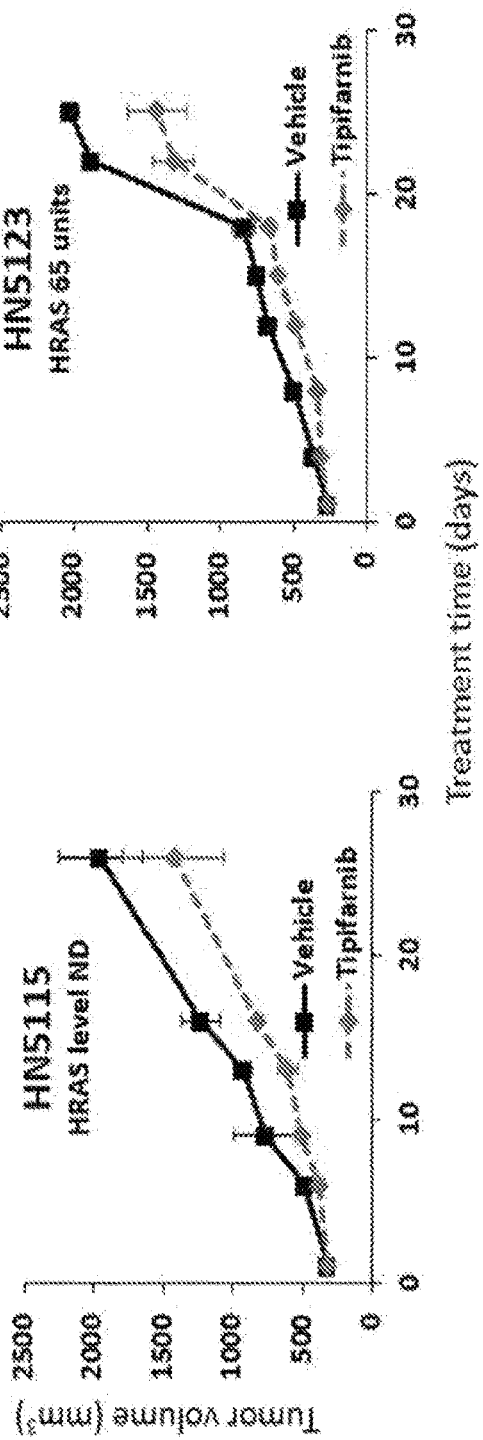

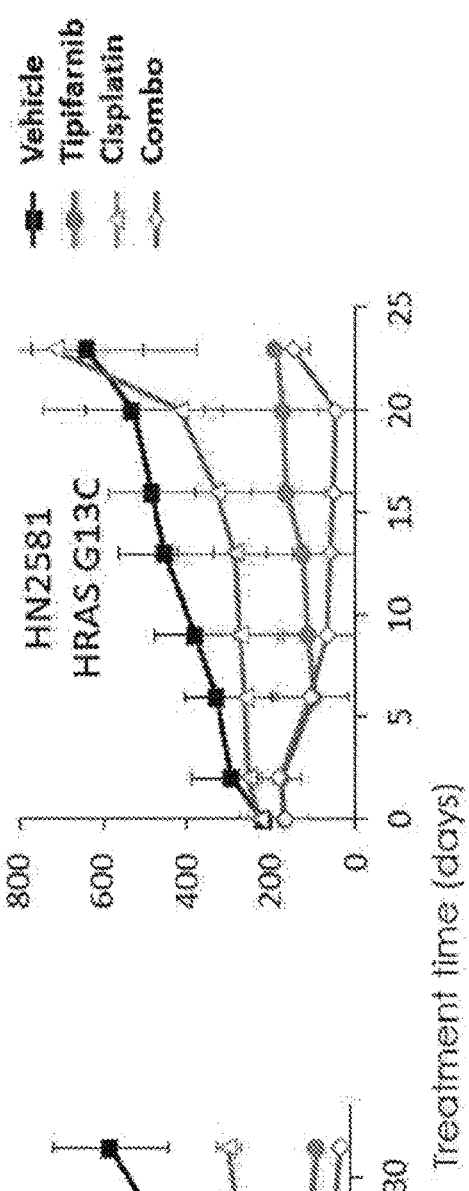
FIG. 7A
FIG. 7B
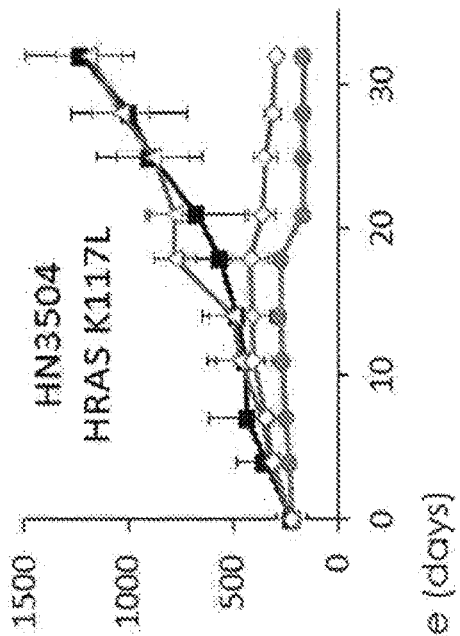
FIG. 7C
FIG. 7D

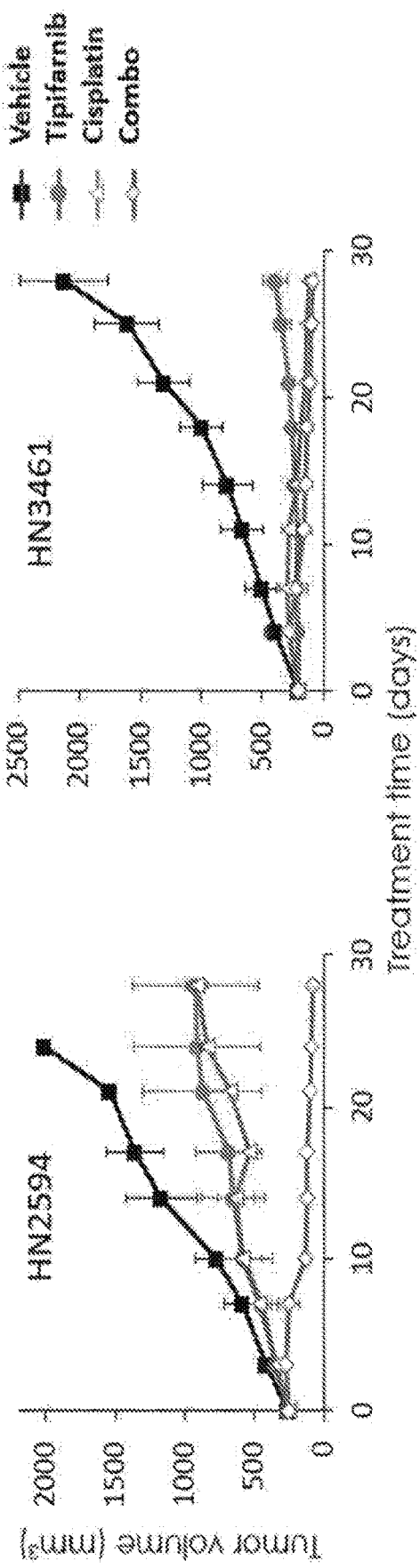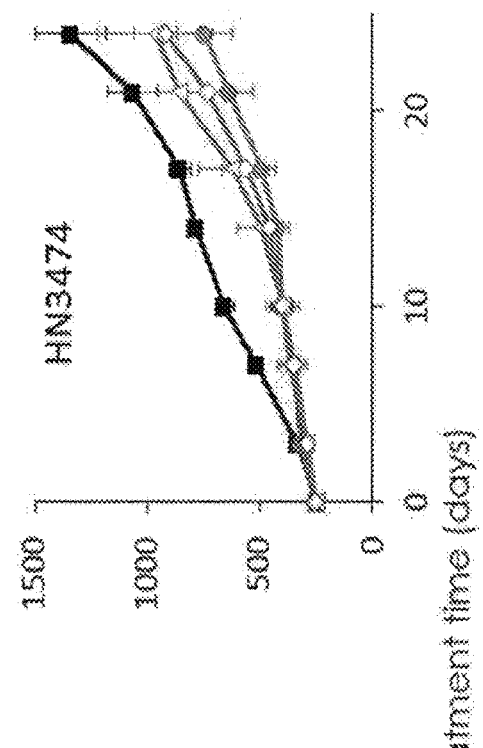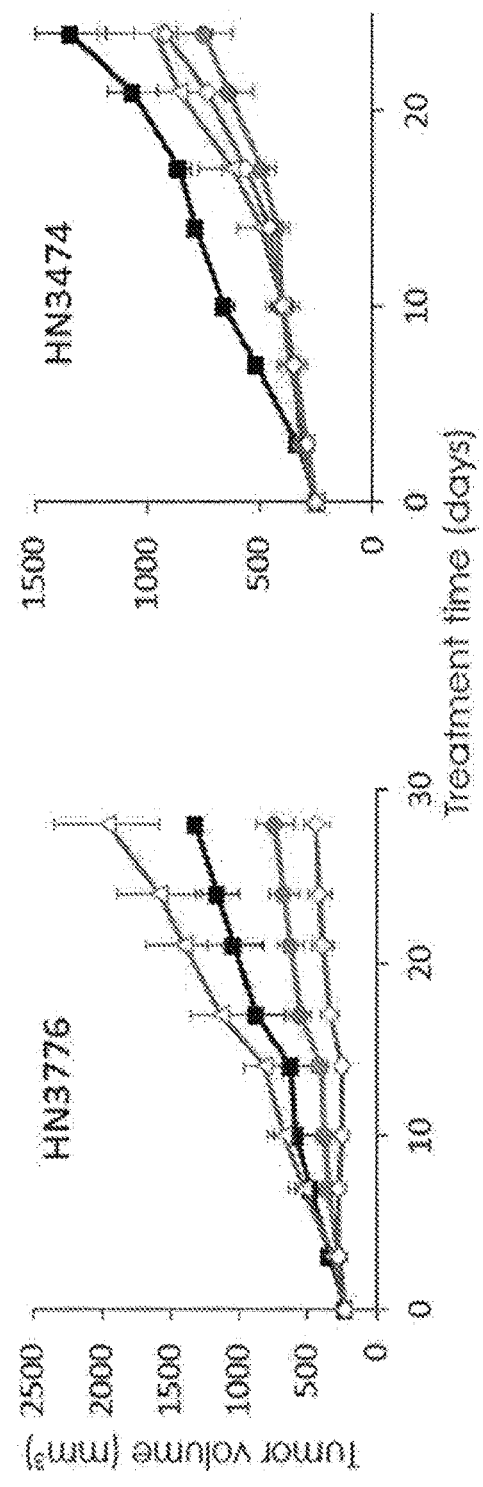

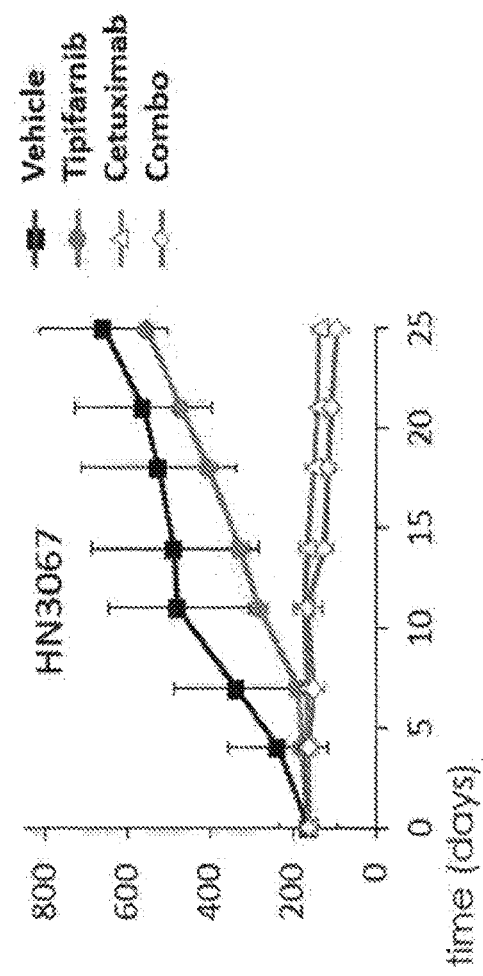
FIG. 11A
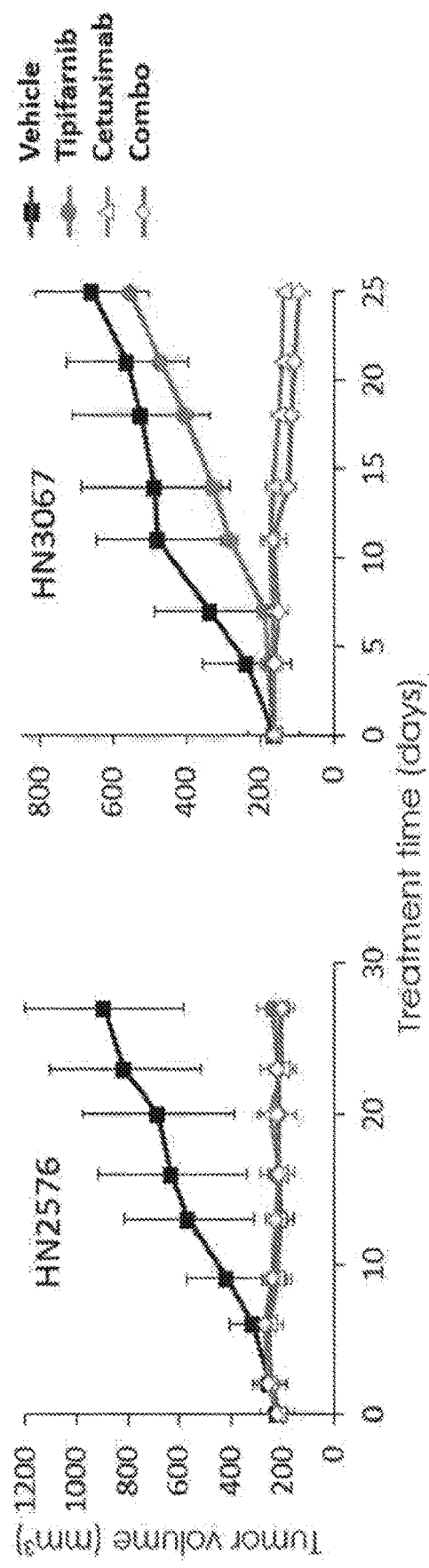
FIG. 11B
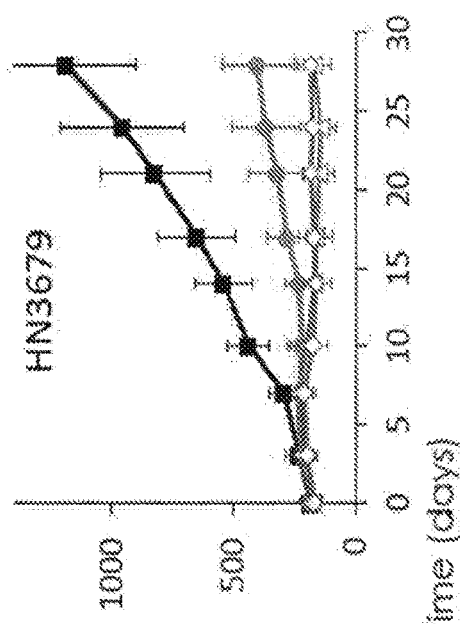
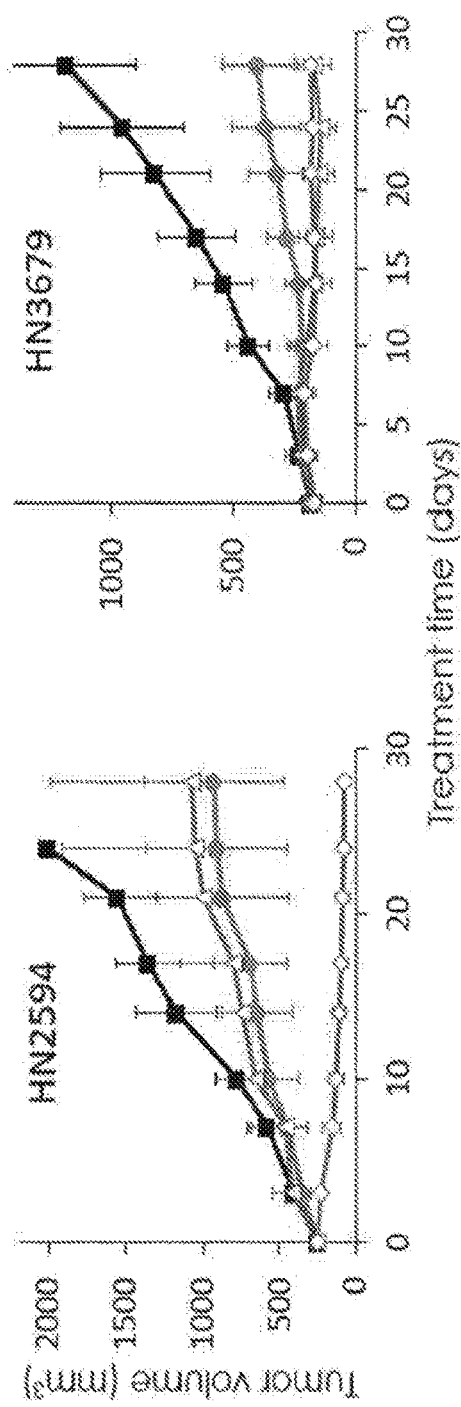
FIG. 11C
FIG. 11D

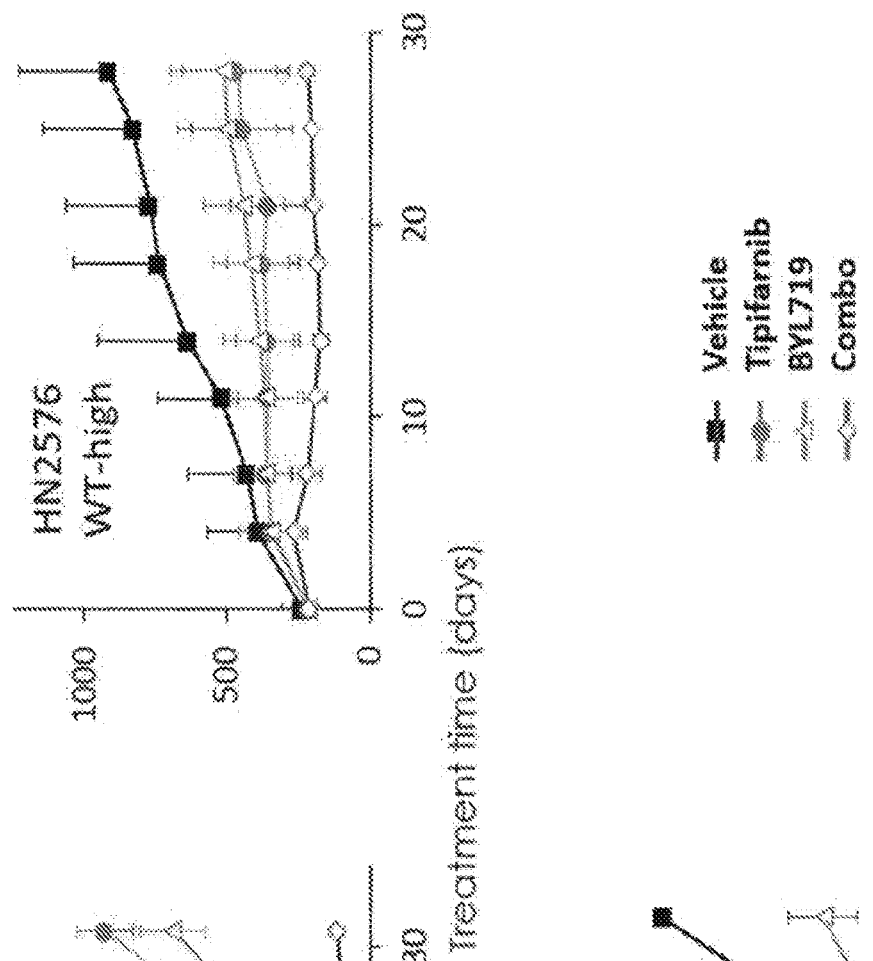
FIG. 12A
FIG. 12B
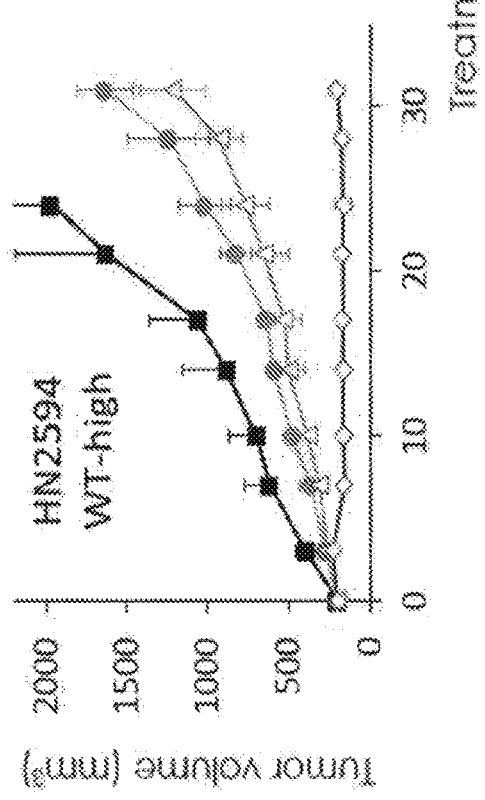
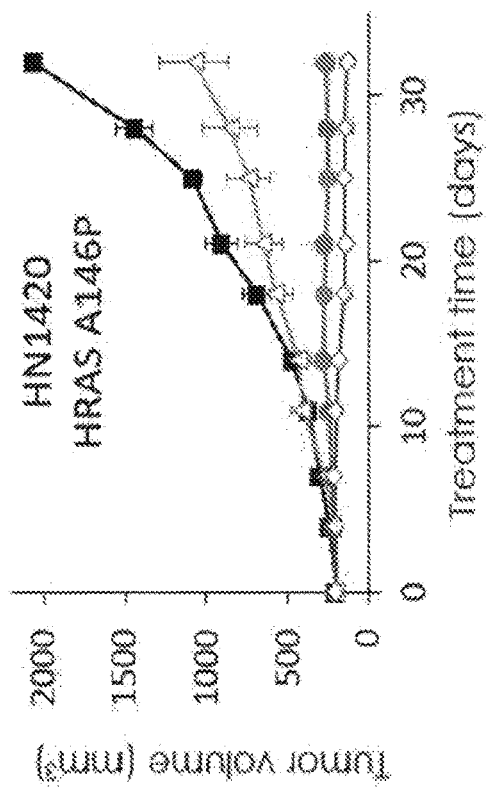
FIG. 12C

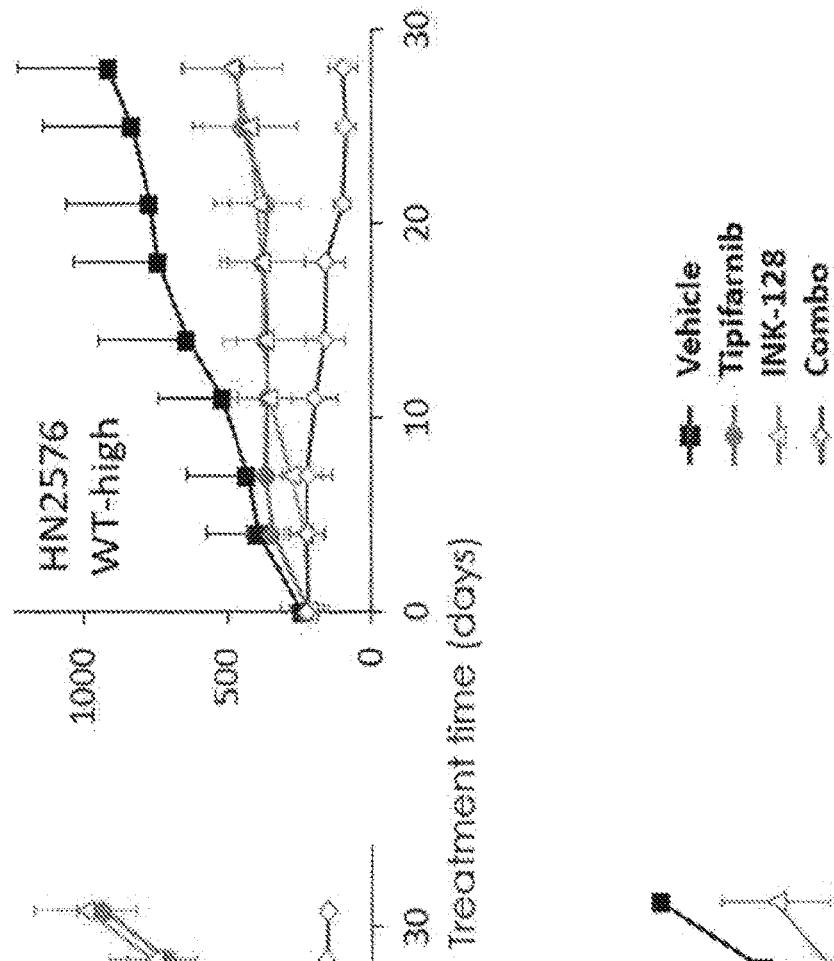
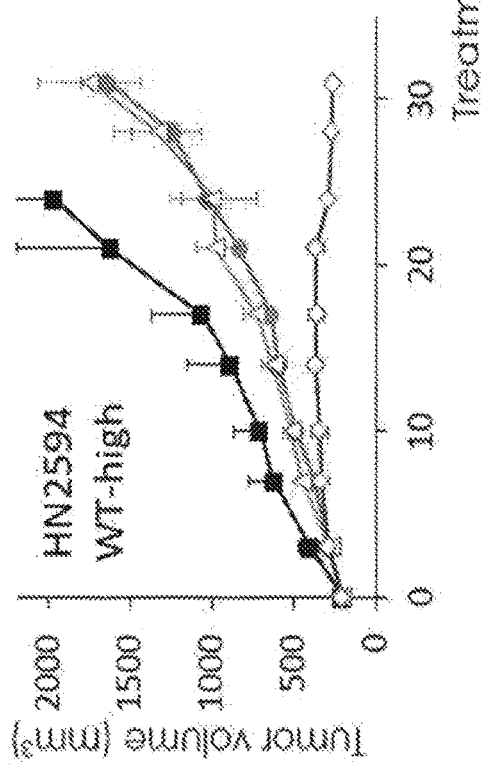
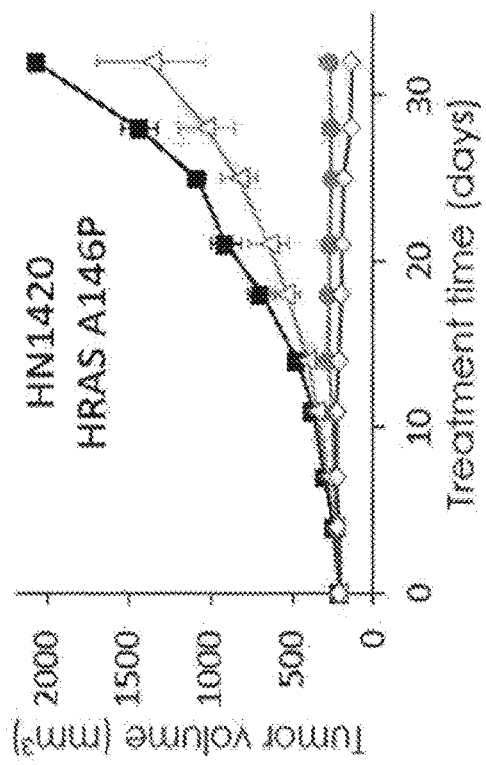
FIG. 14A
FIG. 14B
FIG. 14C

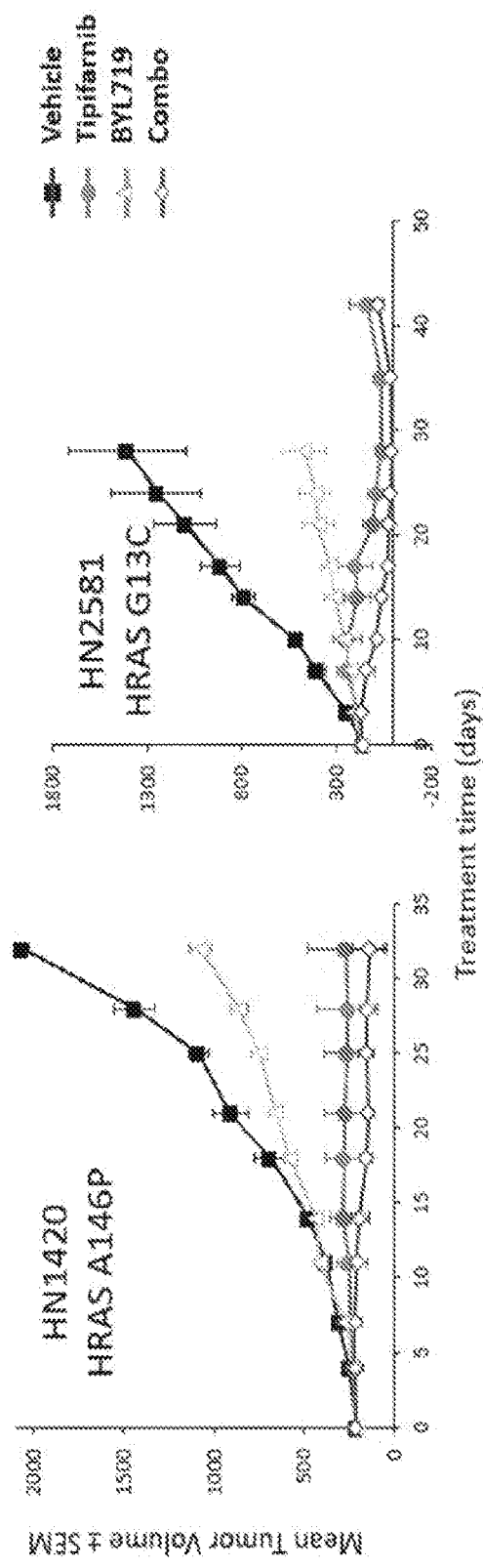
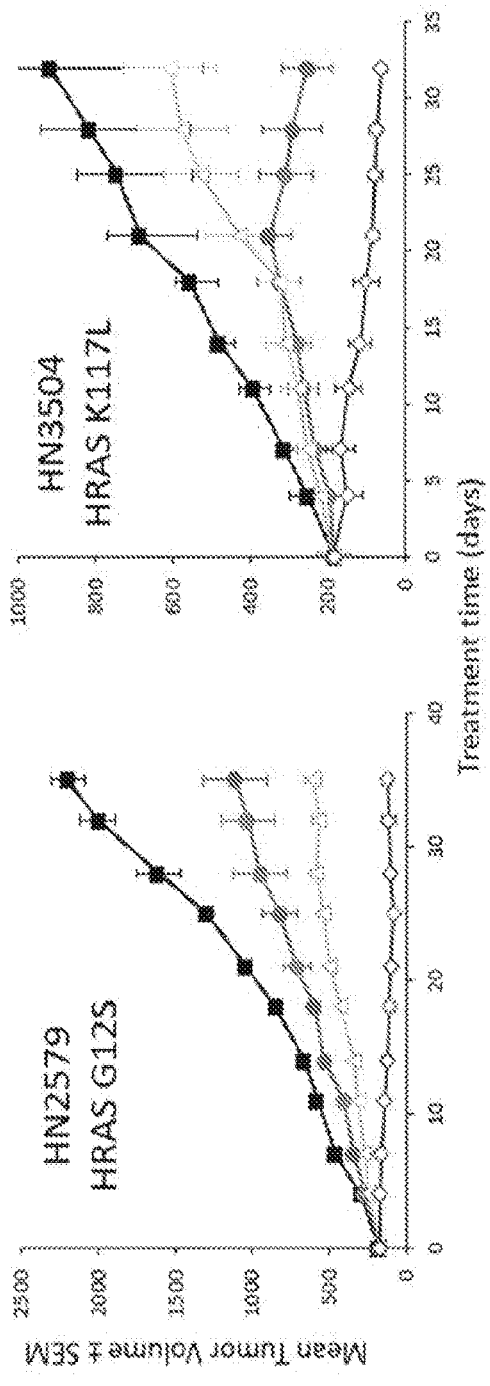
FIG. 15A  FIG. 15B  FIG. 15C  FIG. 15D

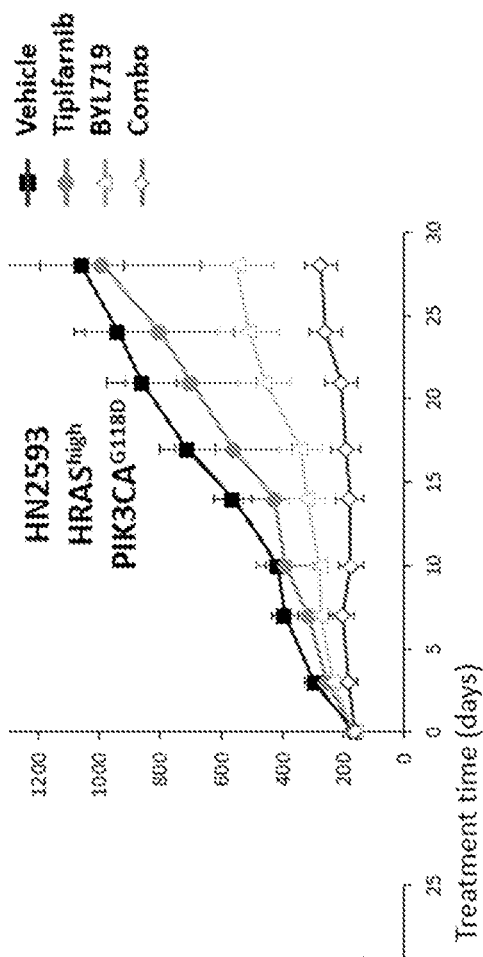
FIG. 16A
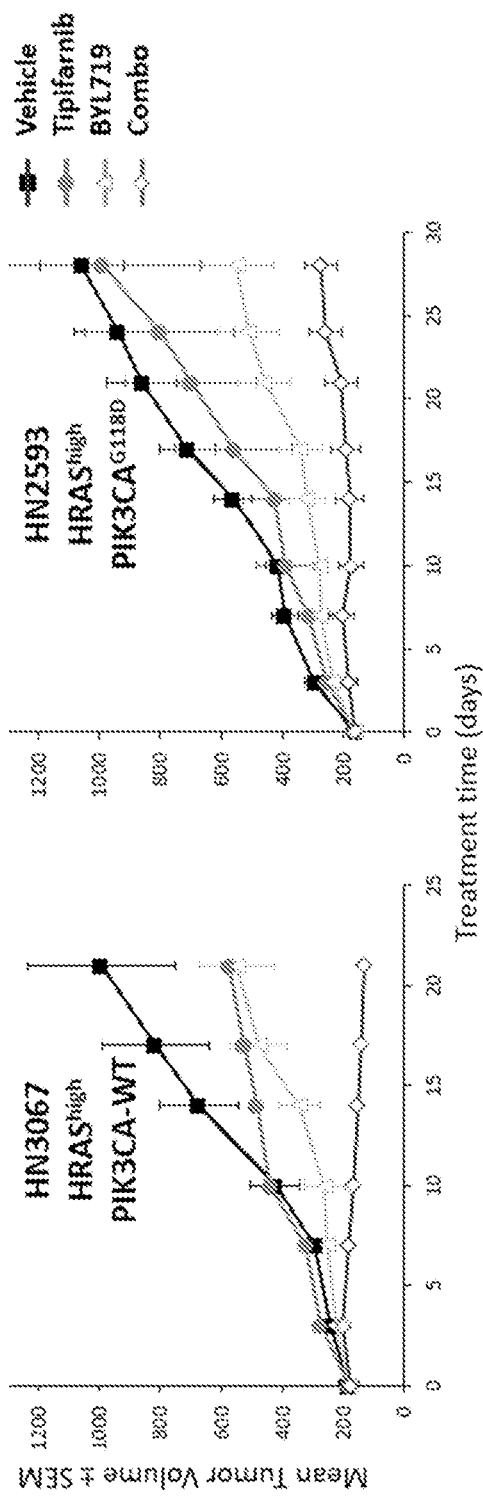
FIG. 16B
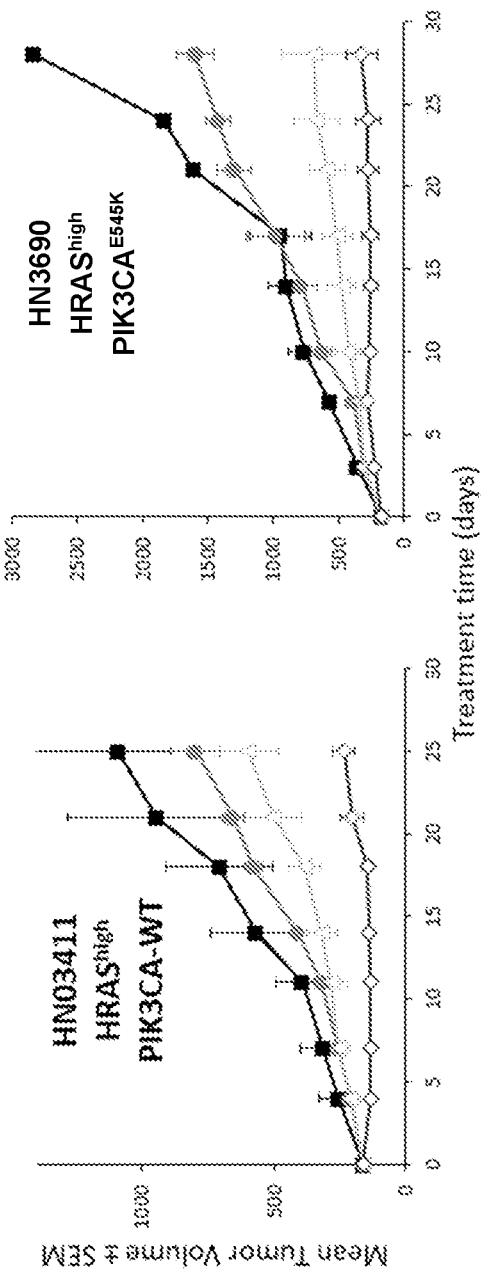
FIG. 16C
FIG. 16D

US 11,672,774 B2

METHODS OF TREATING SQUAMOUS CELL CARCINOMAS WITH FARNESYLTRANSFERASE INHIBITORS

CROSS REFERENCE

This application is a continuation application of International Patent Application No. PCT/US2020/025149, filed Mar. 27, 2020, which claims the benefit of priority from U.S. Provisional Application No. 62/992,749, filed Mar. 20, 2020, and further claims the benefit of priority from U.S. Provisional Application No. 62/826,771, filed Mar. 29, 2019. Each of the foregoing related applications, in its entirety, is incorporated herein by reference.

FIELD

The present invention relates to the field of cancer therapy. In particular, provided herein are methods of treating squamous cell carcinomas with farnesyltransferase inhibitors.

BACKGROUND

Stratification of patient populations to improve therapeutic response rate is increasingly valuable in the clinical management of cancer patients. Farnesyltransferase inhibitors (FTI) are therapeutic agents that have utility in the treatment of cancers, such as Squamous Cell Carcinomas ("SCC"). However, patients respond differently to an FTI treatment. Therefore, methods to predict the responsiveness of a subject having cancer to an FTI treatment, or methods to select cancer patients for an FTI treatment, represent unmet needs. The methods and compositions provided herein meet these needs and provide other related advantages.

SUMMARY

Provided herein are methods of treating an SCC in a subject by administering a therapeutically effective amount of a farnesyltransferase inhibitor (FTI) to the subject that has H-Ras overexpressing SCC. In some embodiments, the subject has an H-Ras expression that is at least 2 fold, at least 3 fold, at least 4 fold, at least 5 fold, at least 10 fold, at least 15 fold, or at least 20 fold greater than a reference level. In some embodiments, the reference level is the median expression level of H-Ras in a population of healthy subjects. In some embodiments, the reference level is the median expression level of H-Ras in a population of subjects having SCC.

In some embodiments, provided herein are methods of treating an SCC in a subject by administering a therapeutically effective amount of a FTI to the subject, wherein the subject has a higher ratio of H-Ras expression to K-Ras expression than a reference ratio. In some embodiments, provided herein are methods of treating an SCC in a subject by administering a therapeutically effective amount of a FTI to the subject, wherein the subject has a higher ratio of H-Ras expression to N-Ras expression than a reference ratio. In some embodiments, provided herein are methods of treating an SCC in a subject by administering a therapeutically effective amount of an FTI to the subject, wherein the subject has a higher ratio of H-Ras expression to the combined expression of K-Ras and N-Ras than a reference ratio. In some embodiments, the reference ratio is 1/10, 1/9, 1/8, 1/7, 1/6, 1/5, 1/4, 1/3, 1/2, 1, 2, 3, 4, 5, 6, 7, 8, 9, or 10. In some embodiments, the reference ratio is the median ratio in a population of healthy subjects. In some embodiments, the reference ratio is the median ratio in a population of subjects having SCC.

In some embodiments, the SCC also has an H-Ras mutation. In some embodiments, the H-Ras mutation includes an amino acid substitution at a codon selected from a group consisting of G12, G13, Q61, Q22, K117, A146, and any combination thereof.

In some embodiments, the mutant HRAS gene encodes a mutant H-Ras protein, wherein the HRAS gene mutation is or comprises a modification in a codon that encodes an amino acid substitution at a specific position selected from a group consisting of G12, G13, Q61, Q22, K117, A146, and any combination thereof, in the corresponding mutant H-Ras protein.

In some embodiments, the SCC is head and neck SCC (HNSCC), lung SCC (LSCC), thyroid SCC (TSCC), esophagus SCC (ESCC), bladder SCC (BSCC) or urothelial carcinoma (UC).

In some embodiments, the SCC is HNSCC. The HNSCC can be HNSCC of the trachea. The HNSCC can be HNSCC of the maxilla. The HNSCC can be HNSCC of the oral cavity.

In some embodiments, the SCC is human papillomavirus (HPV)-negative. In some embodiments, the SCC is at an advanced stage or metastatic. In some embodiments, the SCC is relapsed. In some embodiments, the SCC is refractory.

In some embodiments, the methods provided herein include analyzing the H-Ras expression level in a sample from the subject. In some embodiments, the methods provided herein further include analyzing the K-Ras expression, N-Ras expression, or both in the sample.

In some embodiments, the methods provided herein include measuring the protein level of H-Ras, K-Ras, N-Ras, or any combination thereof. The protein level can be determined using a immunohistochemistry (IHC) approach, an immunoblotting assay, flow cytometry (FACS), or ELISA.

In some embodiments, the methods provided herein include measuring the mRNA level of H-Ras, K-Ras, N-Ras, or any combination thereof. The mRNA level can be measured using qPCR, RT-PCR, RNA-seq, microarray analysis, SAGE, MassARRAY technique, or FISH.

In some embodiments, the methods provided herein include determining the mutation status of H-Ras in the sample.

In some embodiments, the sample is a tissue biopsy. In some embodiments, the sample is a tumor biopsy. In some embodiments, the sample is isolated cells.

In some embodiments, the FTI used in methods provided herein is selected from the group consisting of tipifarnib, lonafarnib, arglabin, perrilyl alcohol, L778123, L739749, FTI-277, L744832, CP-609,754, R208176, AZD3409, and BMS-214662.

In some embodiments, the FTI is tipifarnib. In some embodiments, the FTI is lonafarnib. In some embodiments, the FTI is BMS-214662.

In some embodiments, the tipifarnib is administered at a dose of 0.05-500 mg/kg body weight. In some embodiments, the tipifarnib is administered twice a day.

In some embodiments, the tipifarnib is administered at a dose of 100-1200 mg twice a day. In some embodiments, the tipifarnib is administered at a dose of 100 mg, 200 mg, 300 mg, 400 mg, 600 mg, 900 mg or 1200 mg twice a day.

In some embodiments, the tipifarnib is administered on days 1-7 and 15-21 of a 28-day treatment cycle. In some embodiments, the tipifarnib is administered on days 1-21 of a 28-day treatment cycle. In some embodiments, the tipifarnib is administered on days 1-7 of a 28-day treatment cycle.

In some embodiments, the tipifarnib is administered for at least 1 cycle. In some embodiments, the tipifarnib is administered for at least 3 cycles, 6 cycles, 9 cycles, or 12 cycles.

In some embodiments, the tipifarnib is administered before, during, or after radiation.

In some embodiments, the methods provided herein further include administering a therapeutically effective amount of a second active agent. The tipifarnib can be administered before, during, or after the administration of the second active agent. In some embodiments, the amount of tipifarnib administered in combination with the second active agent is less than the amount of tipifarnib administered in a monotherapy treatment.

In some embodiments, the second active agent is selected from the group consisting of a DNA-hypomethylating agent, an alkylating agent, a topoisomerase inhibitor, a therapeutic antibody that specifically binds to a cancer antigen, a hematopoietic growth factor, a cytokine, an antibiotic, a cox-2 inhibitor, a CDK inhibitor, a PI3K-α inhibitor, an AKT inhibitor an MTOR 1/2 inhibitor, an immunomodulatory agent, an anti-thymocyte globulin, an immunosuppressive agent, and a corticosteroid or a pharmacological derivative thereof.

In some embodiments, the second active agent is an EGFR inhibitor. In some embodiments, the EGFR inhibitor is cetuximab. In some embodiments, the second active agent is an alkylating agent. In some embodiments, the alkylating agent is cisplatin. In some embodiments, the second active agent is a CDK inhibitor. In some embodiments, the CDK inhibitor is palbociclib. In some embodiments, the second active agent is an anti-PD1 antibody, an anti-PDL1 antibody, or an anti-CTLA-4 antibody. In some embodiments, the second active agent is a PI3K-α inhibitor. In some embodiments, the PI3K-α inhibitor is BYL719. In some embodiments, the second active agent is an AKT inhibitor. In some embodiments, the AKT inhibitor is GSK2141795. In some embodiments, the second active agent is an MTOR 1/2 inhibitor. In some embodiments, the MTOR 1/2 inhibitor is INK-128.

In some embodiments, the methods provided herein further include administering a support care therapy.

BRIEF DESCRIPTION OF THE DRAWINGS

FIGS. 1A-1D depict tumor growth curves of mice inoculated with primary human HNSCC tissues and treated with either tipifamib or vehicle. Four HNSCC PDX models with varying H-Ras expression levels and H/K+N ratios were tested. FIG. 1A. Tipifarnib treatment resulted in tumor regression in HNSCC PDX Model HN2576 (H/K+N=4.6; H-Ras=3.0×median). FIG. 1B. Tipifarnib treatment inhibited tumor growth in HNSCC PDX Model HN2594 (H/K+N=3.6; H-Ras=2.8× median). FIG. 1C. Tipifarnib treatment resulted in modest inhibition in tumor growth in HNSCC PDX Model FIN 5111 (H/K+N=2.2; H-Ras=1.3×median). FIG. 1D. Tipifarnib treatment resulted in modest inhibition in tumor growth in HNSCC PDX Model HN5123 (H/K+N=2.1; H-Ras=1.6× median).

FIGS. 2A and 2B depict tumor growth curves of mice inoculated with primary human ESCC tissues and treated with either tipifarnib or vehicle. FIG. 2A. Tipifarnib treatment resulted in tumor regression in ESCC PDX Model ES0204 (H/K+N=6.3). FIG. 2B. Tipifarnib treatment inhibited tumor growth in ESCC PDX Model ES0172 (H/K+ N=6.3). FIGS. 2C and 2D depict tumor growth curves of mice inoculated with primary human breast cancer tissues and treated with either tipifamib or vehicle. FIG. 2C. Tipifarnib treatment did not inhibit tumor growth in breast cancer PDX Model BR1282 (H/K+N=22.6). FIG. 2D. Tipifarnib treatment resulted in modest inhibition of tumor growth in breast cancer PDX Model BR1458 (H/K+ N=10.4).

FIG. 3A. Tumor growth curves of mice treated with vehicle, tipifarnib, cetuximab, or both agents. FIG. 3B. Tumor growth curves of mice treated with vehicle, tipifamib, cisplatin, or both agents. FIG. 3C. Tumor growth curves of mice treated with vehicle, tipifarnib, palbociclib, or both agents.

FIG. 4A. Tumor growth curves of mice treated with vehicle, tipifarnib, cetuximab, or both agents. FIG. 4B. Tumor growth curves of mice treated with vehicle, tipifarnib, cisplatin, or both agents. FIG. 4C. Tumor growth curves of mice treated with vehicle, tipifarnib, palbociclib, or both agents.

FIGS. 5A-5D depict tumor growth curves of mice inoculated with primary human HNSCC tissues and treated with either tipifarnib or vehicle. Four HNSCC PDX models with high H-Ras expression levels and/or H/K+N ratios were tested. FIG. 5A. Tipifarnib treatment resulted in tumor regression in HNSCC PDX Model HN2576. FIG. 5B. Tipifarnib treatment inhibited tumor growth in HNSCC PDX Model HN2594. FIG. 5C. Tipifarnib treatment inhibited tumor growth in HNSCC PDX Model HN3461. FIG. 5D. Tipifarnib treatment inhibited tumor growth in HNSCC PDX Model HN3679.

FIGS. 6A-6D. Modest efficacy of tipifarnib in HNSCC PDX models with low H-Ras expression levels or low H-Ras/K-Ras+N-Ras ("H/K+N") ratios. FIGS. 6A-6D depict tumor growth curves of mice inoculated with primary human HNSCC tissues and treated with either tipifarnib or vehicle. Four HNSCC PDX models with low H-Ras expression levels and/or H/K+N ratios were tested. FIG. 6A. Tipifarnib treatment resulted in partial to no inhibition (inactivity) in tumor growth in HNSCC PDX Model HN2222. Tipifarnib treatment resulted in partial inhibition in tumor growth in HNSCC PDX Model HN5111 (FIG. 6B), in HNSCC PDX Model HN5115 (FIG. 6C), and in HNSCC PDX Model HN5123 (FIG. 6D).

FIGS. 7A-7D. Combination treatment of tipifarnib and a second agent (cisplatin) synergistically inhibited tumor growth in mutated H-Ras HNSCC PDX Models HN2579 (FIG. 7A), HN2581 (FIG. 7B), HN1420 (FIG. 7C), and HN3504 (FIG. 7D), each figure showing tumor growth curves of mice treated with vehicle, tipifarnib, cisplatin, or combination therapy with both agents in the respective models.

FIGS. 9A-9D. Combination treatment of tipifarnib and a second agent (cisplatin) inhibited tumor growth in HNSCC PDX Models HN2594 (FIG. 9A), HN3461 (FIG. 9B), HN3776 (FIG. 9C), and HN3474 (FIG. 9D), wherein the models have high H-Ras expression and/or high H/N+K Ratios, and figure showing tumor growth curves of mice treated with vehicle, tipifarnib, cisplatin, or combination therapy with both agents in the respective models.

FIGS. 11A-11D. Combination treatment of tipifarnib and a second agent (cetuximab) inhibited tumor growth in HNSCC PDX Models HN2576 (FIG. 11A), HN3067 (FIG. 11B), HN2594 (FIG. 11C), and HN3679 (FIG. 11D), wherein the models have high H-Ras expression and/or high H/N+K Ratios, and figure showing tumor growth curves of mice treated with vehicle, tipifarnib, cetuximab, or combination therapy with both agents in the respective models.

FIGS. 12A-12C. Combination treatment of tipifarnib and a second agent (PI3K-α inhibitor BYL719) inhibited tumor growth in HNSCC PDX Models HN2594 (FIG. 12A) and HN2576 (FIG. 12B) (wherein both models have high H-Ras expression and/or high H/N+K Ratios), and in PDX HNSCC model HN1420 (FIG. 12C) having mutated H-Ras gene expression (at codon for HRAS A146P), wherein the FIGS. 12A-12C show tumor growth curves of mice treated with vehicle, tipifarnib, BYL719, or combination therapy with both agents in the respective models.

FIGS. 14A-14C. Combination treatment of tipifarnib and a second agent (MTORC 1/2 inhibitor INK-128) inhibited tumor growth in HNSCC PDX Models HN2594 (FIG. 14A) and HN2576 (FIG. 14B) (wherein both models have high H-Ras expression and/or high H/N+K Ratios), and in PDX HNSCC model HN1420 (FIG. 14C) having mutated H-Ras gene expression (at codon for HRAS A146P), wherein the FIGS. 14A-14C show tumor growth curves of mice treated with vehicle, tipifarnib, INK-128, or combination therapy with both agents in the respective models.

FIGS. 15A-15D. Combination treatment of tipifarnib and a second agent (PI3K-α inhibitor BYL719) inhibited tumor growth in HNSCC PDX Models HN1420 (FIG. 15A), HN2581 (FIG. 15B), HN2579 (FIG. 15C), and HN3504 (FIG. 15D), having mutated H-Ras gene expressions (at codons for HRAS A146P, HRAS G13C, HRAS G12S, and HRAS K117L, respectively), wherein the FIGS. 15A-15D show tumor growth curves of mice treated with vehicle, tipifarnib, BYL719, or combination therapy with both agents in the respective models.

FIGS. 16A-16D. Combination treatment of tipifarnib and a second agent (PI3K-α inhibitor BYL719) inhibited tumor growth in HNSCC PDX Models HN3067 (FIG. 16A) and HN3411 (FIG. 16C) having high H-Ras expression levels and wild type PIK3CA expression, and in PDX HNSCC models HN2593 (FIG. 16B) and HN3690 (FIG. 16D) having high H-Ras expression levels and having mutated PIK3CA expression (at codons for PI3K-α G118D and PI3K-α E545K, respectively), wherein the FIGS. 16A-16D show tumor growth curves of mice treated with vehicle, tipifarnib, BYL719, or combination therapy with both agents in the respective models.

DETAILED DESCRIPTION

Figure 1A:
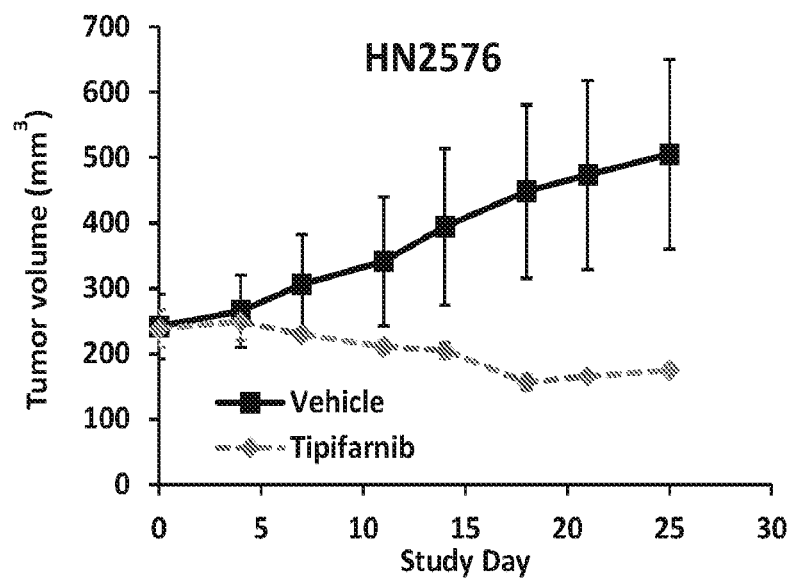
FIGS. 1A-1D. Increased efficacy of tipifarnib in HNSCC PDX models with high H-Ras expression levels or high H-Ras/K-Ras+N-Ras ("H/K+N") ratios.

As used herein, the articles "a," "an," and "the" refer to one or to more than one of the grammatical object of the article. By way of example, a sample refers to one sample or two or more samples.

As used herein, the term "subject" refers to a mammal. A subject can be a human or a non-human mammal such as a dog, cat, bovid, equine, mouse, rat, rabbit, or transgenic species thereof. A subject can be a human.

As used herein, the term "sample" refers to a material or mixture of materials containing one or more components of interest. A sample from a subject refers to a sample obtained from the subject, including samples of biological tissue or fluid origin, obtained, reached, or collected in vivo or in situ. A sample can be obtained from a region of a subject containing precancerous or cancer cells or tissues. Such samples can be, but are not limited to, organs, tissues, fractions and cells isolated from a mammal. Exemplary samples include lymph node, whole blood, partially purified blood, serum, plasma, bone marrow, and peripheral blood mononuclear cells ("PBMC"). A sample also can be a tissue biopsy. Exemplary samples also include cell lysate, a cell culture, a cell line, a tissue, oral tissue, gastrointestinal tissue, an organ, an organelle, a biological fluid, a blood sample, a urine sample, a skin sample, and the like.

As used herein, the term "analyzing" a sample refers to carrying that an art-recognized assay to make an assessment regarding a particular property or characteristic of the sample. The property or characteristic of the sample can be, for example, the type of the cells in the sample, or the expression level of a gene in the sample.

As used herein, the terms "treat," "treating," and "treatment," when used in reference to a cancer patient, can refer to an action that reduces the severity of the cancer, or retards or slows the progression of the cancer, including (a) inhibiting the cancer growth, or arresting development of the cancer, and (b) causing regression of the cancer, or delaying or minimizing one or more symptoms associated with the presence of the cancer. For example, "treating" a cancer, such as a H-Ras overexpressing SCC in a subject refers to an action inhibiting the cancer growth in the subject.

As used herein, the term "administer," "administering," or "administration" refers to the act of delivering, or causing to be delivered, a compound or a pharmaceutical composition to the body of a subject by a method described herein or otherwise known in the art. Administering a compound or a pharmaceutical composition includes prescribing a compound or a pharmaceutical composition to be delivered into the body of a patient. Exemplary forms of administration include oral dosage forms, such as tablets, capsules, syrups, suspensions; injectable dosage forms, such as intravenous (IV), intramuscular (IM), or intraperitoneal (IP); transdermal dosage forms, including creams, jellies, powders, or patches; buccal dosage forms; inhalation powders, sprays, suspensions, and rectal suppositories.

As used herein, the term "selecting" and "selected" in reference to a subject is used to mean that a particular subject is specifically chosen from a larger group of subjects on the basis of (due to) the particular subject meeting a predetermined criterion or a set of predetermined criteria, e.g., having a higher H-Ras expression than a reference level. Similarly, "selectively treating" a subject refers to providing treatment to a subject meeting a predetermined criterion or a set of predetermined criteria. Similarly, "selectively administering" refers to administering a drug to a subject meeting a predetermined criterion or a set of predetermined criteria. By selecting, selectively treating and selectively administering, it is meant that a subject having SCC is delivered a personalized therapy based on the subject's biology, rather than being delivered a standard treatment regimen based solely on having SCC.

As used herein, the term "therapeutically effective amount" of a compound when used in connection with a disease or disorder refers to an amount sufficient to provide a therapeutic benefit in the treatment of the disease or disorder or to delay or minimize one or more symptoms associated with the disease or disorder. The disease or disorder refers can be SCC. A therapeutically effective amount of a compound means an amount of the compound that when used alone or in combination with other therapies, would provide a therapeutic benefit in the treatment or management of the disease or disorder. The term encompasses an amount that improves overall therapy, reduces or avoids symptoms, or enhances the therapeutic efficacy of another therapeutic agent. The term also refers to the amount of a compound that sufficiently elicits the biological or medical response of a biological molecule (e.g., a protein, enzyme, RNA, or DNA), cell, tissue, system, animal, or human, which is being sought by a researcher, veterinarian, medical doctor, or clinician.

As used herein, the term "express" or "expression" when used in connection with a gene refers to the process by which the information carried by the gene becomes manifest as the phenotype, including transcription of the gene to a messenger RNA (mRNA), the subsequent translation of the mRNA molecule to a polypeptide chain and its assembly into the ultimate protein.

As used herein, the term "expression level" of a gene refers to the amount or accumulation of the expression product of the gene, such as, for example, the amount of a RNA product of the gene (the mRNA level of the gene) or the amount of a protein product of the gene (the protein level of the gene). If the gene has more than one allele, the expression level of a gene refers to the total amount of accumulation of the expression product of all existing alleles for this gene, unless otherwise specified.

As used herein, the term "reference" when used in connection with a quantifiable value refers to a predetermined value that one can use to determine the significance of the value as measured in a sample.

As used herein, the term "reference expression level" refers to a predetermined expression level of a gene that one can use to determine the significance of the expression level of the gene in a sample. The sample can be a cell, a group of cells, or a tissue. For example, a reference expression level of a gene can also be a cut-off value determined by a person of ordinary skill in the art through statistical analysis of the expression levels of the gene in various sample cell populations. In some embodiments, the reference expression level of H-Ras can be the median expression level of H-Ras in a population of healthy subjects. In some embodiments, the reference expression level of H-Ras can be the median expression level of H-Ras in a population of subjects having the same type of tumor. For example, the reference expression level for HNSCC patients can be the median expression level of H-Ras in a population of HNSCC patients. For another example, the reference expression level for LSCC patients can be the median expression level of H-Ras in a population of LSCC patients. For another example, the reference expression level for BSCC patients can be the median expression level of H-Ras in a population of BSCC patients. For another example, the reference expression level for UC patients can be the median expression level of H-Ras in a population of UC patients. In some embodiments, the reference expression level of H-Ras can be a cutoff percentile of H-Ras expression in a population of subjects having the same type of tumor. The cutoff percentile can be the top 10%, 15%, 20%, 25%, 30%, 35%, 40%, 45%, or 50% cutoff. The cutoff percentile can be the top 10% cutoff. The cutoff percentile can be the top 15% expression cutoff. The cutoff percentile can be the top 20% cutoff. The cutoff percentile can be the top 25% cutoff. The cutoff percentile can be the top 30% cutoff. The cutoff percentile can be the top 35% cutoff. The cutoff percentile can be the top 40% cutoff. The cutoff percentile can be the top 45% cutoff. The cutoff percentile can be the top 50% cutoff. For example, the reference expression level for HNSCC patients can be the top 30% cutoff of H-Ras expression in a population of HNSCC patients. For example, the reference expression level for LSCC patients can be the top 30% cutoff of H-Ras expression in a population of LSCC patients. For example, the reference expression level for BSCC patients can be the top 30% cutoff of H-Ras expression in a population of BSCC patients. For example, the reference expression level for UC patients can be the top 30% cutoff of H-Ras expression in a population of UC patients. The reference expression level can be determined by a person of ordinary skill in the art through, for example, statistic analysis of the H-Ras expression levels in samples from a clinical cohort.

As used herein, the term "overexpress" or "overexpression" when used in connection with a gene means that the expression level of the gene in a tissue of a subject is higher than a reference level, wherein the reference level is at least the median expression level of the gene in the same tissue in a healthy population. The tissue can also be a tumor. In some embodiments, a gene that is "overexpressed" in a subject can be expressed at a level that is at least 2 fold, at least 3 fold, at least 4 fold, at least 5 fold, at least 10 fold, at least 15 fold, or at least 20 fold greater than a reference level. A gene that is overexpressed in a particular tumor in a subject means that the expression level of the gene in the tumor in the subject is higher than a reference level, wherein the reference level is at least the median expression level of the gene in the corresponding tissue in a healthy population.

In some embodiments, a gene that is overexpressed in a particular SCC in a subject can mean that the expression level of the gene in the SCC of the subject is higher than the median expression level of the gene in the tumor samples in a population of subjects having the same tumor. For example, a subject having H-Ras overexpressing HNSCC can mean that the H-Ras expression level in the HNSCC of the subject is higher than at least the median expression level of H-Ras in the corresponding head and neck tissue in a heathy population, or, in some embodiments, higher than the median expression level of H-Ras in tumor samples from a population of HNSCC patients. The reference level can also be a cutoff percentile of expression level of H-Ras in a population of subjects having the same type of tumor, and thus a subject having H-Ras overexpressing HNSCC can mean that the H-Ras expression level in the HNSCC of the subject is higher than a cutoff percentile of H-Ras expression in a population of HNSCC patients. For another example, a subject having H-Ras overexpressing LSCC can mean that the H-Ras expression level in the LSCC of the subject is higher than at least the median expression level of H-Ras in the corresponding lung tissue in a heathy population, or, in some embodiments, higher than the median expression level of H-Ras in tumor samples from a population of LSCC patients. The reference level can also be a cutoff percentile of expression level of H-Ras in a population of subjects having the same type of tumor, and thus a subject having H-Ras overexpressing LSCC can mean that the H-Ras expression level in the LSCC of the subject is higher than a cutoff percentile of H-Ras expression in a population of LSCC patients. For another example, a subject having H-Ras overexpressing UC can mean that the H-Ras expression level in the UC of the subject is higher than at least the median expression level of H-Ras in the corresponding urothelial tissue in a heathy population, or, in some embodiments, higher than the median expression level of H-Ras in tumor samples from a population of UC patients. The reference level can also be a cutoff percentile of expression level of H-Ras in a population of subjects having the same type of tumor, and thus a subject having H-Ras overexpressing UC can mean that the H-Ras expression level in the UC of the subject is higher than a cutoff percentile of H-Ras expression in a population of UC patients.

The cutoff percentile can be the top 10%, 15%, 20%, 25%, 30%, 35%, 40%, 45%, or 50% cutoff. For example, the cutoff percentile can be the top 25% cutoff. In some embodiments, the subjects having H-Ras overexpressing HNSCC can be the 25% patients of a HNSCC patient population having the highest H-Ras expression in the population. In some embodiments, the subjects having H-Ras overexpressing LSCC can be the 25% patients of a LSCC patient population having the highest H-Ras expression in the population. In some embodiments, the subjects having H-Ras overexpressing BSCC can be the 25% patients of a BSCC patient population having the highest H-Ras expression in the population. In some embodiments, the subjects having H-Ras overexpressing UC can be the 25% patients of a UC patient population having the highest H-Ras expression in the population. In some embodiments, the expression level of a gene that is overexpressed in a tumor of a subject can be at least 2 fold, at least 3 fold, at least 4 fold, at least 5 fold, at least 10 fold, at least 15 fold, or at least 20 fold greater than a reference level.

The term "reference ratio" as used herein in connection with the expression levels of two or more genes refers to a ratio predetermined by a person of ordinary skill in the art that can be used to determine the significance of the ratio of the levels of these genes in a sample. The sample can be a cell, a group of cells, or a tissue. For example, a reference ratio of H-Ras expression to the combined expression of K-Ras and N-Ras can be a predetermined ratio of H-Ras expression to the combined expression of K-Ras and N-Ras. The reference ratio of the expression levels of two or more genes can be the median ratio of expression levels of these genes in a population of subjects. For example, a reference ratio of H-Ras expression to the combined expression of K-Ras and N-Ras can be the median ratio in a heathy population. For another example, a reference ratio of H-Ras expression to the combined expression of K-Ras and N-Ras can be the median ratio in a population of patients having the same type of tumor. The reference ratio can also be a cutoff percentile of the expression ratio in a population of subjects having the same type of tumor. The cutoff percentile can be the top 10%, 15%, 20%, 25%, 30%, 35%, 40%, 45%, or 50% cutoff. The cutoff percentile can be the top 10% cutoff. The cutoff percentile can be the top 15% expression cutoff. The cutoff percentile can be the top 20% cutoff. The cutoff percentile can be the top 25% cutoff. The cutoff percentile can be the top 30% cutoff. The cutoff percentile can be the top 35% cutoff. The cutoff percentile can be the top 40% cutoff. The cutoff percentile can be the top 45% cutoff. The cutoff percentile can be the top 50% cutoff. For example, the reference expression ratio for HNSCC patients can be the top 30% cutoff of the ratio of H-Ras expression to the combined expression of K-Ras and N-Ras in a population of HNSCC patient. A reference ratio can also be a cut-off value determined by a person of ordinary skill in the art through, for example, statistical analysis of ratios of expression levels of the two genes in various sample cell populations. In certain embodiments, the reference ratio is 1/10, 1/9, 1/8, 1/7, 1/6, 1/5, 1/4, 1/3, 1/2, 1, 2, 3, 4, 5, 6, 7, 8, 9, 10, 15 or 20. In some embodiments, the reference ratio is 1/10. In some embodiments, the reference ratio is 1/9. In some embodiments, the reference ratio is 1/8. In some embodiments, the reference ratio is 1/7. In some embodiments, the reference ratio is 1/6. In some embodiments, the reference ratio is 1/5. In some embodiments, the reference ratio is 1/4. In some embodiments, the reference ratio is 1/3. In some embodiments, the reference ratio is 1/2. In some embodiments, the reference ratio is 1. In some embodiments, the reference ratio is 2. In some embodiments, the reference ratio is 3. In some embodiments, the reference ratio is 4. In some embodiments, the reference ratio is 5. In some embodiments, the reference ratio is 6. In some embodiments, the reference ratio is 7. In some embodiments, the reference ratio is 8. In some embodiments, the reference ratio is 9. In some embodiments, the reference ratio is 10. In some embodiments, the reference ratio is 15. In some embodiments, the reference ratio is 20.

As used herein, the term "responsiveness" or "responsive" when used in connection with a treatment refers to the effectiveness of the treatment in lessening or decreasing the symptoms of the disease being treated. In connection with a SCC patient, the patient is responsive to an FTI treatment if the FTI treatment effectively inhibits the growth, or arrests development of SCC, causes regression of SCC, or delays or minimizes one or more symptoms associated with the presence of SCC in this patient.

As used herein, the term "likelihood" refers to the probability of an event. A subject is "likely" to be responsive to a particular treatment when a condition is met means that the probability of the subject to be responsive to a particular treatment is higher when the condition is met than when the condition is not met. The probability to be responsive to a particular treatment can be higher by, for example, 5%, 10%, 25%, 50%, 100%, 200%, or more in a subject who meets a particular condition compared to a subject who does not meet the condition. For example, a subject having SCC is "likely" responsive to an FTI treatment when the subject has a high H-Ras expression or high H-Ras/N+K-Ras expression ratio means that the probability of a subject to be responsive to FTI treatment is 5%, 10%, 25%, 50%, 100%, 200%, or more higher in a subject who has H-Ras overexpression or a higher H-Ras/N+K-Ras expression ratio than a reference ratio compared to a subject who does not have H-Ras overexpression or has a lower H-Ras/N+K-Ras expression ratio than a reference ratio.

A. Methods

Provided herein are methods for selecting a subject having SCC for treatment with an FTI. The methods provided herein are based, in part, on the discovery that SCC patients with different gene expression respond differently to an FTI treatment, and that the clinical benefits of FTI treatment are associated with the expression levels of certain genes. For example, the methods provided herein are based on the discovery that patients having H-Ras overexpressing SCC are likely responsive to an FTI treatment, and selection of a patient population having H-Ras overexpressing SCC for an FTI treatment can increase the overall response rate of the FTI treatment for SCC.

Additionally, the methods provided herein are also based, in part, on the discovery that SCC patients having high ratios of H-Ras expression to the K-Ras expression ("H/K ratio"), high ratios of H-Ras expression to the N-Ras expression ("H/N ratio"), or high ratios of H-Ras expression to the combined expression of K-Ras and N-Ras ("H/K+N ratio"), are likely responsive to an FTI treatment, and selection of SCC patient population having high H/K ratios, high H/N ratios, or high H/N+K ratios for an FTI treatment can increase the overall response rate of the FTI treatment for SCC.

Accordingly, provided herein are methods for treating SCC in a subject by administering a therapeutically effective amount of an FTI to the subject that has H-Ras overexpressing SCC. Provided herein are also methods for increasing the responsiveness of an FTI treatment for SCC by selectively treating SCC patients having H-Ras overexpression. Provided herein are also methods of predicting responsiveness of a subject having SCC to an FTI treatment based on the expression level of H-Ras, wherein a subject is predicted to be likely responsive if the subject has H-Ras overexpression.

In some embodiments, provided herein are methods for treating SCC in a subject, including administering a therapeutically effective amount of an FTI to the subject, wherein the subject has H-Ras expression higher than a reference level. In some embodiments, the methods include analyzing a sample from the subject to measure the expression level of H-Ras in the sample, and determining that the subject has H-Ras overexpressing SCC, if the H-Ras expression level in the sample is higher than a reference level.

The FTI can be any FTI, including those described herein. For example, the FTI can be tipifarnib, lonafarnib, arglabin, perrilyl alcohol, L778123, L739749, FTI-277, L744832, CP-609,754, R208176, AZD3409, or BMS-214662. In some embodiments, the FTI is tipifarnib. Accordingly, provided herein are methods for treating SCC in a subject by administering a therapeutically effective amount of tipifarnib to the subject that has H-Ras overexpressing SCC. Provided herein are also methods for increasing the responsiveness of tipifarnib treatment for SCC by selectively treating SCC patients having H-Ras overexpression. Provided herein are also methods of predicting responsiveness of a subject having SCC to tipifarnib treatment based on the expression level of H-Ras, wherein a subject is predicted to be likely responsive if the subject has H-Ras overexpression.

In some embodiments, provided herein are methods to treat SCC in a subject, including administering a therapeutically effective amount of tipifarnib to the subject, wherein the subject has H-Ras expression higher than a reference level. In some embodiments, the methods include analyzing a sample from the subject to measure the expression level of H-Ras in the sample, and determining that the subject has H-Ras overexpressing SCC if the H-Ras expression level in the sample is higher than a reference level.

In some embodiments, the subject has a H-Ras expression that is at least 2 fold, at least 2.5 fold, at least 3 fold, at least 3.5 fold, at least 4 fold, at least 4.5 fold, at least 5 fold, at least 6 fold, at least 7 fold, at least 8 fold, at least 9 fold, at least 10 fold, at least 12 fold, at least 15 fold, or at least 20 fold greater than a reference level. In some embodiments, the subject has a H-Ras expression that is at least 2 fold greater than a reference level. In some embodiments, the subject has a H-Ras expression that is at least 2.5 fold greater than a reference level. In some embodiments, the subject has a H-Ras expression that is at least 3 fold greater than a reference level. In some embodiments, the subject has a H-Ras expression that is at least 3.5 fold greater than a reference level. In some embodiments, the subject has a H-Ras expression that is at least 4 fold greater than a reference level. In some embodiments, the subject has a H-Ras expression that is at least 4.5 fold greater than a reference level. In some embodiments, the subject has a H-Ras expression that is at least 5 fold greater than a reference level. In some embodiments, the subject has a H-Ras expression that is at least 6 fold greater than a reference level. In some embodiments, the subject has a H-Ras expression that is at least 7 fold greater than a reference level. In some embodiments, the subject has a H-Ras expression that is at least 8 fold greater than a reference level. In some embodiments, the subject has a H-Ras expression that is at least 9 fold greater than a reference level. In some embodiments, the subject has a H-Ras expression that is at least 10 fold greater than a reference level. In some embodiments, the subject has a H-Ras expression that is at least 12 fold greater than a reference level. In some embodiments, the subject has a H-Ras expression that is at least 15 fold greater than a reference level. In some embodiments, the subject has a H-Ras expression that is at least 20 fold greater than a reference level. In some embodiments, the reference level is the median expression level of H-Ras in a population of healthy subjects. In some embodiments, the reference level is the median expression level of H-Ras in a population of subjects having SCC.

Squamous cell carcinoma (SCC) is an uncontrolled growth of abnormal cells arising from the squamous cells in the epidermis. Common types include head and neck SCC (HNSCC), lung SCC (LSCC), thyroid SCC, esophagus SCC, bladder SCC, or urothelial carcinoma (UC). Human papillomavirus infection (HPV) has been associated with SCC development.

HNSCC is the $6^{th}$ most common cancer worldwide, with about 650,000 cases and 200,000 deaths per year worldwide, and about 54,000 new cases per year in the US. It is also the most common cancer in central Asia. HNSCC has 2 different etiologies and corresponding tumor types. The first subtype is associated with tobacco smoking and alcohol consumption, and unrelated to Human papillomavirus (HPV− or HPV negative). The second subtype is associated with infection with high-risk HPV (HPV+ or HPV positive). The second subtype is largely limited to oropharyngeal cancers. HPV+ tumors are distinct entity with better prognosis and may require differential treatments. A significant proportion of HNSCC, particularly oropharyngeal cancers, are caused by HPV infection. High-risk HPV subtype 16 accounts for 85% of all HPV+ tumors in HNSCC. P16 can be used as surrogate marker of HPV infection in HNSCC, particularly in the oropharynx. More accurate HPV testing is available and based on E6/E7 detection (Liang C, et al. Cancer Res. 2012; 72:5004-5013).

HPV+ HNSCC show significantly lower EGFR expression levels than HPV− HNSCC. EGFR amplification only occurs in HPV− HNSCC. High EGFR gene copy number and protein expression are associated with poor clinical outcome in advanced HNSCC.

Currently, first-line therapy for recurrent/metastatic HNSCC include platinum-based doublet (e.g., cisplatin/5-FU or carboplatin/paclitaxel), optionally in combination with anti-EGFR antibody therapy (e.g. cetuximab, panitumumab, afatinib). Second-line therapy includes taxanes, methotrexate, and/or cetuximab. Anti-EGFR antibody therapy, such as cetuximab (a chimeric IgG1) or panitumumab can be used as a single agent, with chemotherapy (e.g. platinum/5-FU, cisplatin), or with radiation therapy. Despite high EGFR expression levels in HNSCC, single-agent response rate for cetuximab is only 13% with SD rate of 33%, and there is currently no predictive biomarker available.

Drugs in development for HNSCC include those targeting PI3K pathway: BKM120 (buparlisib)+cetuximab, BYL719+cetuximab, Temsirolimus+cetuximab, Rigosertib+cetuximab; those targeting MET pathway: Tivantinib+cetuximab, Ficlatuzumab+cetuximab; those targeting EGFR/HER3 pathway Afatinib+cetuximab f paclitaxel, Patritumab; those targeting FGFR pathway: BGJ398; those targeting CDK4/6-cell cycle pathway: Palbociclib, LEE011, abemaciclib, and ribociclib; RTK inhibitor: Anlotinib; PI3K-α inhibitors: BYL719; AKT inhibitors: MK2206, GSK2110183, and GSK2141795; MTOR 1/2 inhibitors: INK-128; and chemotherapy: Oral Azacitidine. More recent therapeutic options for HNSCC include immunotherapy, such as anti-PD1 or anti-PDL1 antibodies. While high cure rates have been achieved for localized and loco-regional disease using surgery, radiation, chemoradiation, and induction chemotherapy, survival rates for recurrent/metastatic diseases remain very poor, and better treatment options are necessary.

SCC of the lung ("LSCC") accounts for about 30% of all lung cancers. This type of lung cancer tends to be found in the middle of the lungs. Approved treatment options for LSCC include surgery, radiation therapy, chemotherapy, angiogenesis inhibitor, and immunotherapy. Lung cancer that is only in one lung and that has not spread to other organs is often treated with surgery, if the patient can tolerate it. Radiation therapy can be given as the main treatment in early-stage squamous cell lung cancer if surgery is not possible. In that case, it can be given either with or without chemotherapy. In some cases, radiation therapy is used before or after surgery.

Patients whose lung cancer has spread beyond the lung to local lymph nodes are often given chemotherapy and radiation therapy. Patients with LSCC are often given two chemotherapy agents as first-line therapy. The platinum-based drugs cisplatin or carboplatin are combined with another chemotherapy drug. An example is cisplatin in combination with gemcitabine. The drug, necitumumab (Portrazza™), is also approved by the FDA as first-line treatment of people with metastatic LSCC to be used in combination with cisplatin and gemcitabine. If the LSCC has not been shown to have EGFR mutations, necitumumab seems to work by blocking EGFR protein expression. There are a number of other post-first-line therapy options for LSCC, such as chemotherapy with or without an angiogenesis inhibitor, or immunotherapy, such as nivolumab. The kinase inhibitor afatinib (Gilotrif®), is FDA-approved for the treatment of patients with metastatic LSCC that has progressed after platinum-based chemotherapy. Additional treatment options include ramucirumab (Cyramza®), Nivolumab (Opdivo®), Pembrolizumab (Keytruda) or Atezolizumab (Tecentriq®).

SCC of the thyroid gland ("thyroid SCC" or "TSCC") can either be a primary or secondary disease, in which it could be due to a direct extension of adjacent lesions or metastasis from other primary foci. The latter are 10-times more common. Primary SCC of the thyroid gland is an unusual type of thyroid malignancy. It is more common in females, with a mean age of occurrence in the sixth decade. Currently, surgical resection of the tumor with adjuvant radiotherapy and chemotherapy is the recommended option. The extent of the surgical resection is poorly defined. However, in advanced stage diseases, the extensive and invasive nature of the thyroid SCC can be the main factor of surgical failure. Moreover, primary thyroid SCC is also relatively resistant to radiotherapy, while standard chemotherapy has shown minimal to absent response towards the disease. General prognosis of primary SCC of the thyroid is very unfavorable regardless of the treatment, due to its aggressive nature. Better treatment options are needed.

Esophageal squamous cell carcinoma ("Esophageal SCC" or "ESCC") is one of the most aggressive squamous cell carcinomas and is highly prevalent in Asia. Patients with ESCC are treated endoscopically or with surgery, chemotherapy, or radiotherapy, based on tumor stage. Minimally invasive treatments help improve the quality of life of patients who undergo such treatments. Early-stage ESCC, with negligible risk of metastasis to the lymph node, can be cured by endoscopic local treatment, such as ER and/or an ablative method (e.g., radiofrequency ablation or photodynamic therapy). Surgery is also used widely to obtain locoregional control and has an important role in the treatment of esophageal cancer. Neoadjuvant or neoadjuvant chemoradiation is performed as standard treatment for locally advanced ESCC. Combinations of cisplatin and 5-FU are commonly used in chemotherapy for patients with unresectable locally advanced or metastatic ESCC, which is believed to be better than the best supportive care. Target therapies such as anti-EGFR antibodies (e.g. cetuximab), anti-PD1/PD-L1 antibodies are also under investigation.

Bladder squamous cell carcinoma ("Bladder SCC" or "BSCC") usually presents at a late stage and portends poor prognosis. Bladder SCC represent 2-5% of bladder malignancies in the U.S. BSCC is divided into two subtypes, BSCC associated with bilharzia infection (schistosomiasis), i.e. bilharzial-associated BSCC (B-BSCC) and BSCC not associated with bilharziasis, i.e. non-bilharzial-associated SCC (NB-BSCC). B-BSCC and NB-BSCC differ in their epidemiology, natural history, and clinicopathological features. B-BSCC is predominantly found in regions where schistosomiasis is endemic, such as in the Middle East, Southeast Asia, and South America. In the USA, NB-BSCC has been reported in patients with spinal cord injury (SCI), particularly following long-term use of an indwelling catheter. Patients with NB-BSCC are generally diagnosed at a late stage and present with poor prognosis. Both B-BSCC and NB-BSCC are treated with radical cystectomy (RC); the use of other treatments, including neoadjuvant and adjuvant therapies in conjunction with RC, is not well established. Additional studies incorporating multimodal approaches, contemporary radiation techniques, immunotherapies and systemic therapies are also needed.

Urothelial carcinoma (UC) is an indication with a 5-year survival rate of 77%. Cells of UC commonly exhibit squamous differentiation and characteristics, defined by the presence of intercellular bridges, keratinization, or both. Liu et al., *Cancer Control* 24(1):78-82 (2017).

In some embodiments of the methods provided herein, the SCC is human papillomavirus (HPV)-negative SCC. In some embodiments, the SCC is at an advanced stage. In some embodiments, the SCC is metastatic SCC. In some embodiments, the SCC is relapsed SCC. In some embodiments, the SCC is refractory. The SCC can be a specific type of SCC. For example, the SCC can head and neck SCC (HNSCC), lung SCC (LSCC), thyroid SCC, esophagus SCC, bladder SCC, or urothelial carcinoma (UC).

In some embodiments, the SCC is HNSCC, and provided herein are methods for treating HNSCC in a subject by administering a therapeutically effective amount of an FTI to the subject that has H-Ras overexpressing HNSCC. Provided herein are also methods for increasing the responsiveness of an FTI treatment for HNSCC by selectively treating HNSCC subjects having H-Ras overexpression. Provided herein are also methods of predicting responsiveness of a subject having HNSCC to an FTI treatment based on the expression level of H-Ras, wherein a subject is predicted to be likely responsive if the subject has H-Ras overexpression.

In some embodiments, provided herein are methods for treating HNSCC in a subject, including administering a therapeutically effective amount of an FTI to the subject, wherein the subject has H-Ras expression higher than a reference level. In some embodiments, the methods include analyzing a sample from the subject to measure the expression level of H-Ras in the sample, and determining that the subject has H-Ras overexpressing HNSCC, if the H-Ras expression level in the sample is higher than a reference level.

The FTI can be any FTI, including those described herein. For example, the FTI can be tipifarnib, lonafarnib, arglabin, perrilyl alcohol, L778123, L739749, FTI-277, L744832, CP-609,754, R208176, AZD3409, or BMS-214662. In some embodiments, the FTI is tipifarnib. Accordingly, provided herein are methods for treating HNSCC in a subject by administering a therapeutically effective amount of tipifarnib to the subject that has H-Ras overexpressing HNSCC. Provided herein are also methods for increasing the responsiveness of tipifarnib treatment for HNSCC by selectively treating HNSCC subjects having H-Ras overexpression. Provided herein are also methods of predicting responsiveness of a subject having HNSCC to tipifarnib treatment based on the expression level of H-Ras, wherein a subject is predicted to be likely responsive if the subject has H-Ras overexpression.

In some embodiments, provided herein are methods to treat HNSCC in a subject, including administering a therapeutically effective amount of tipifarnib to the subject, wherein the subject has H-Ras expression higher than a reference level. In some embodiments, the methods include analyzing a sample from the subject to measure the expression level of H-Ras in the sample, and determining that the subject has H-Ras overexpressing HNSCC if the H-Ras expression level in the sample is higher than a reference level.

In some embodiments, the subject has a H-Ras expression that is at least 2 fold, at least 2.5 fold, at least 3 fold, at least 3.5 fold, at least 4 fold, at least 4.5 fold, at least 5 fold, at least 6 fold, at least 7 fold, at least 8 fold, at least 9 fold, at least 10 fold, at least 12 fold, at least 15 fold, or at least 20 fold greater than a reference level. In some embodiments, the reference level is the median expression level of H-Ras in a population of healthy subjects. In some embodiments, the reference level is the median expression level of H-Ras in a population of subjects having HNSCC.

In some embodiments, the HNSCC is HNSCC of the trachea. In some embodiments, the HNSCC is HNSCC of the maxilla. In some embodiments, the HNSCC is HNSCC of the oral cavity. In some embodiments, the HNSCC is human papillomavirus (HPV)-negative HNSCC. In some embodiments, the HNSCC is at an advanced stage. In some embodiments, the HNSCC is metastatic HNSCC. In some embodiments, the HNSCC is relapsed HNSCC. In some embodiments, the HNSCC is refractory HNSCC.

In some embodiments, the SCC is LSCC, and provided herein are methods for treating LSCC in a subject by administering a therapeutically effective amount of an FTI to the subject that has H-Ras overexpressing LSCC. Provided herein are also methods for increasing the responsiveness of an FTI treatment for LSCC by selectively treating LSCC patients having H-Ras overexpression. Provided herein are also methods of predicting responsiveness of a subject having LSCC to an FTI treatment based on the expression level of H-Ras, wherein a subject is predicted to be likely responsive if the subject has H-Ras overexpression.

In some embodiments, provided herein are methods for treating LSCC in a subject, including administering a therapeutically effective amount of an FTI to the subject, wherein the subject has H-Ras expression higher than a reference level. In some embodiments, the methods include analyzing a sample from the subject to measure the expression level of H-Ras in the sample, and determining that the subject has H-Ras overexpressing LSCC, if the H-Ras expression level in the sample is higher than a reference level.

The FTI can be any FTI, including those described herein. For example, the FTI can be tipifarnib, lonafarnib, arglabin, perrilyl alcohol, L778123, L739749, FTI-277, L744832, CP-609,754, R208176, AZD3409, or BMS-214662. In some embodiments, the FTI is tipifarnib. Accordingly, provided herein are methods for treating LSCC in a subject by administering a therapeutically effective amount of tipifarnib to the subject that has H-Ras overexpressing LSCC. Provided herein are also methods for increasing the responsiveness of tipifarnib treatment for LSCC by selectively treating LSCC patients having H-Ras overexpression. Provided herein are also methods of predicting responsiveness of a subject having LSCC to tipifarnib treatment based on the expression level of H-Ras, wherein a subject is predicted to be likely responsive if the subject has H-Ras overexpression.

In some embodiments, provided herein are methods to treat LSCC in a subject, including administering a therapeutically effective amount of tipifarnib to the subject, wherein the subject has H-Ras expression higher than a reference level. In some embodiments, the methods include analyzing a sample from the subject to measure the expression level of H-Ras in the sample, and determining that the subject has H-Ras overexpressing LSCC if the H-Ras expression level in the sample is higher than a reference level.

In some embodiments, the subject has a H-Ras expression that is at least 2 fold, at least 2.5 fold, at least 3 fold, at least 3.5 fold, at least 4 fold, at least 4.5 fold, at least 5 fold, at least 6 fold, at least 7 fold, at least 8 fold, at least 9 fold, at least 10 fold, at least 12 fold, at least 15 fold, or at least 20 fold greater than a reference level. In some embodiments, the reference level is the median expression level of H-Ras in a population of healthy subjects. In some embodiments, the reference level is the median expression level of H-Ras in a population of subjects having LSCC.

In some embodiments, the LSCC is human papillomavirus (HPV)-negative LSCC. In some embodiments, the LSCC is at an advanced stage. In some embodiments, the LSCC is metastatic LSCC. In some embodiments, the LSCC is relapsed LSCC. In some embodiments, the LSCC is refractory LSCC.

In some embodiments, the SCC is thyroid SCC, and provided herein are methods for treating thyroid SCC in a subject by administering a therapeutically effective amount of an FTI to the subject that has H-Ras overexpressing thyroid SCC. Provided herein are also methods for increasing the responsiveness of an FTI treatment for thyroid SCC by selectively treating thyroid SCC patients having H-Ras overexpression. Provided herein are also methods of predicting responsiveness of a subject having thyroid SCC to an FTI treatment based on the expression level of H-Ras, wherein a subject is predicted to be likely responsive if the subject has H-Ras overexpression.

In some embodiments, provided herein are methods for treating thyroid SCC in a subject, including administering a therapeutically effective amount of an FTI to the subject, wherein the subject has H-Ras expression higher than a reference level. In some embodiments, the methods include analyzing a sample from the subject to measure the expression level of H-Ras in the sample, and determining that the subject has H-Ras overexpressing thyroid SCC, if the H-Ras expression level in the sample is higher than a reference level.

The FTI can be any FTI, including those described herein. For example, the FTI can be tipifarnib, lonafarnib, arglabin, perrilyl alcohol, L778123, L739749, FTI-277, L744832, CP-609,754, R208176, AZD3409, or BMS-214662. In some embodiments, the FTI is tipifarnib. Accordingly, provided herein are methods for treating thyroid SCC in a subject by administering a therapeutically effective amount of tipifarnib to the subject that has H-Ras overexpressing thyroid SCC. Provided herein are also methods for increasing the responsiveness of tipifarnib treatment for thyroid SCC by selectively treating thyroid SCC patients having H-Ras overexpression. Provided herein are also methods of predicting responsiveness of a subject having thyroid SCC to tipifarnib treatment based on the expression level of H-Ras, wherein a subject is predicted to be likely responsive if the subject has H-Ras overexpression.

In some embodiments, provided herein are methods to treat thyroid SCC in a subject, including administering a therapeutically effective amount of tipifarnib to the subject, wherein the subject has H-Ras expression higher than a reference level. In some embodiments, the methods include analyzing a sample from the subject to measure the expression level of H-Ras in the sample, and determining that the subject has H-Ras overexpressing thyroid SCC if the H-Ras expression level in the sample is higher than a reference level.

In some embodiments, the subject has a H-Ras expression that is at least 2 fold, at least 2.5 fold, at least 3 fold, at least 3.5 fold, at least 4 fold, at least 4.5 fold, at least 5 fold, at least 6 fold, at least 7 fold, at least 8 fold, at least 9 fold, at least 10 fold, at least 12 fold, at least 15 fold, or at least 20 fold greater than a reference level. In some embodiments, the reference level is the median expression level of H-Ras in a population of healthy subjects. In some embodiments, the reference level is the median expression level of H-Ras in a population of subjects having thyroid SCC.

In some embodiments, the thyroid SCC is human papillomavirus (HPV)-negative thyroid SCC. In some embodiments, the thyroid SCC is at an advanced stage. In some embodiments, the thyroid SCC is metastatic thyroid SCC. In some embodiments, the thyroid SCC is relapsed thyroid SCC. In some embodiments, the thyroid SCC is refractory thyroid SCC.

In some embodiments, the SCC is esophagus SCC, and provided herein are methods for treating esophagus SCC in a subject by administering a therapeutically effective amount of an FTI to the subject that has H-Ras overexpressing esophagus SCC. Provided herein are also methods for increasing the responsiveness of an FTI treatment for esophagus SCC by selectively treating esophagus SCC patients having H-Ras overexpression. Provided herein are also methods of predicting responsiveness of a subject having esophagus SCC to an FTI treatment based on the expression level of H-Ras, wherein a subject is predicted to be likely responsive if the subject has H-Ras overexpression.

In some embodiments, provided herein are methods for treating esophagus SCC in a subject, including administering a therapeutically effective amount of an FTI to the subject, wherein the subject has H-Ras expression higher than a reference level. In some embodiments, the methods include analyzing a sample from the subject to measure the expression level of H-Ras in the sample, and determining that the subject has H-Ras overexpressing esophagus SCC, if the H-Ras expression level in the sample is higher than a reference level.

The FTI can be any FTI, including those described herein. For example, the FTI can be tipifarnib, lonafarnib, arglabin, perrilyl alcohol, L778123, L739749, FTI-277, L744832, CP-609,754, R208176, AZD3409, or BMS-214662. In some embodiments, the FTI is tipifarnib. Accordingly, provided herein are methods for treating esophagus SCC in a subject by administering a therapeutically effective amount of tipifarnib to the subject that has H-Ras overexpressing esophagus SCC. Provided herein are also methods for increasing the responsiveness of tipifarnib treatment for esophagus SCC by selectively treating esophagus SCC patients having H-Ras overexpression. Provided herein are also methods of predicting responsiveness of a subject having esophagus SCC to tipifarnib treatment based on the expression level of H-Ras, wherein a subject is predicted to be likely responsive if the subject has H-Ras overexpression.

In some embodiments, provided herein are methods to treat esophagus SCC in a subject, including administering a therapeutically effective amount of tipifarnib to the subject, wherein the subject has H-Ras expression higher than a reference level. In some embodiments, the methods include analyzing a sample from the subject to measure the expression level of H-Ras in the sample, and determining that the subject has H-Ras overexpressing esophagus SCC if the H-Ras expression level in the sample is higher than a reference level.

In some embodiments, the subject has a H-Ras expression that is at least 2 fold, at least 2.5 fold, at least 3 fold, at least 3.5 fold, at least 4 fold, at least 4.5 fold, at least 5 fold, at least 6 fold, at least 7 fold, at least 8 fold, at least 9 fold, at least 10 fold, at least 12 fold, at least 15 fold, or at least 20 fold greater than a reference level. In some embodiments, the reference level is the median expression level of H-Ras in a population of healthy subjects. In some embodiments, the reference level is the median expression level of H-Ras in a population of subjects having esophagus SCC.

In some embodiments, the esophagus SCC is human papillomavirus (HPV)-negative esophagus SCC. In some embodiments, the esophagus SCC is at an advanced stage. In some embodiments, the esophagus SCC is metastatic esophagus SCC. In some embodiments, the esophagus SCC is relapsed esophagus SCC. In some embodiments, the esophagus SCC is refractory esophagus SCC.

In some embodiments, the SCC is bladder SCC, and provided herein are methods for treating bladder SCC in a subject by administering a therapeutically effective amount of an FTI to the subject that has H-Ras overexpressing bladder SCC. Provided herein are also methods for increasing the responsiveness of an FTI treatment for bladder SCC by selectively treating bladder SCC patients having H-Ras overexpression. Provided herein are also methods of predicting responsiveness of a subject having bladder SCC to an FTI treatment based on the expression level of H-Ras, wherein a subject is predicted to be likely responsive if the subject has H-Ras overexpression.

In some embodiments, provided herein are methods for treating bladder SCC in a subject, including administering a therapeutically effective amount of an FTI to the subject, wherein the subject has H-Ras expression higher than a reference level. In some embodiments, the methods include analyzing a sample from the subject to measure the expression level of H-Ras in the sample, and determining that the subject has H-Ras overexpressing bladder SCC, if the H-Ras expression level in the sample is higher than a reference level.

The FTI can be any FTI, including those described herein. For example, the FTI can be tipifamib, lonafarnib, arglabin, perrilyl alcohol, L778123, L739749, FTI-277, L744832, CP-609,754, R208176, AZD3409, or BMS-214662. In some embodiments, the FTI is tipifarnib. Accordingly, provided herein are methods for treating bladder SCC in a subject by administering a therapeutically effective amount of tipifarnib to the subject that has H-Ras overexpressing bladder SCC. Provided herein are also methods for increasing the responsiveness of tipifamib treatment for bladder SCC by selectively treating bladder SCC patients having H-Ras overexpression. Provided herein are also methods of predicting responsiveness of a subject having bladder SCC to tipifarnib treatment based on the expression level of H-Ras, wherein a subject is predicted to be likely responsive if the subject has H-Ras overexpression.

In some embodiments, provided herein are methods to treat bladder SCC in a subject, including administering a therapeutically effective amount of tipifarnib to the subject, wherein the subject has H-Ras expression higher than a reference level. In some embodiments, the methods include analyzing a sample from the subject to measure the expression level of H-Ras in the sample, and determining that the subject has H-Ras overexpressing bladder SCC if the H-Ras expression level in the sample is higher than a reference level.

In some embodiments, the subject has a H-Ras expression that is at least 2 fold, at least 2.5 fold, at least 3 fold, at least 3.5 fold, at least 4 fold, at least 4.5 fold, at least 5 fold, at least 6 fold, at least 7 fold, at least 8 fold, at least 9 fold, at least 10 fold, at least 12 fold, at least 15 fold, or at least 20 fold greater than a reference level. In some embodiments, the reference level is the median expression level of H-Ras in a population of healthy subjects. In some embodiments, the reference level is the median expression level of H-Ras in a population of subjects having bladder SCC.

In some embodiments, the bladder SCC is human papillomavirus (HPV)-negative bladder SCC. In some embodiments, the bladder SCC is at an advanced stage. In some embodiments, the bladder SCC is metastatic bladder SCC. In some embodiments, the bladder SCC is relapsed bladder SCC. In some embodiments, the bladder SCC is refractory bladder SCC.

In some embodiments, the SCC is UC, and provided herein are methods for treating UC in a subject by administering a therapeutically effective amount of an FTI to the subject that has H-Ras overexpressing UC. Provided herein are also methods for increasing the responsiveness of an FTI treatment for UC by selectively treating UC patients having H-Ras overexpression. Provided herein are also methods of predicting responsiveness of a subject having UC to an FTI treatment based on the expression level of H-Ras, wherein a subject is predicted to be likely responsive if the subject has H-Ras overexpression.

In some embodiments, provided herein are methods for treating UC in a subject, including administering a therapeutically effective amount of an FTI to the subject, wherein the subject has H-Ras expression higher than a reference level. In some embodiments, the methods include analyzing a sample from the subject to measure the expression level of H-Ras in the sample, and determining that the subject has H-Ras overexpressing UC, if the H-Ras expression level in the sample is higher than a reference level.

The FTI can be any FTI, including those described herein. For example, the FTI can be tipifarnib, lonafarnib, arglabin, perrilyl alcohol, L778123, L739749, FTI-277, L744832, CP-609,754, R208176, AZD3409, or BMS-214662. In some embodiments, the FTI is tipifarnib. Accordingly, provided herein are methods for treating UC in a subject by administering a therapeutically effective amount of tipifarnib to the subject that has H-Ras overexpressing UC. Provided herein are also methods for increasing the responsiveness of tipifarnib treatment for UC by selectively treating UC patients having H-Ras overexpression. Provided herein are also methods of predicting responsiveness of a subject having UC to tipifarnib treatment based on the expression level of H-Ras, wherein a subject is predicted to be likely responsive if the subject has H-Ras overexpression.

In some embodiments, provided herein are methods to treat UC in a subject, including administering a therapeutically effective amount of tipifarnib to the subject, wherein the subject has H-Ras expression higher than a reference level. In some embodiments, the methods include analyzing a sample from the subject to measure the expression level of H-Ras in the sample, and determining that the subject has H-Ras overexpressing UC if the H-Ras expression level in the sample is higher than a reference level.

In some embodiments, the subject has a H-Ras expression that is at least 2 fold, at least 2.5 fold, at least 3 fold, at least 3.5 fold, at least 4 fold, at least 4.5 fold, at least 5 fold, at least 6 fold, at least 7 fold, at least 8 fold, at least 9 fold, at least 10 fold, at least 12 fold, at least 15 fold, or at least 20 fold greater than a reference level. In some embodiments, the reference level is the median expression level of H-Ras in a population of healthy subjects. In some embodiments, the reference level is the median expression level of H-Ras in a population of subjects having UC.

In some embodiments, the UC is human papillomavirus (HPV)-negative UC. In some embodiments, the UC is at an advanced stage. In some embodiments, the UC is metastatic UC. In some embodiments, the UC is relapsed UC. In some embodiments, the UC is refractory UC.

Provided herein are also methods for treating SCC in a subject by administering a therapeutically effective amount of an FTI to the subject that has a higher H/K ratio than a reference ratio. Provided herein are also methods for increasing the responsiveness of an FTI treatment for SCC by selectively treating SCC patients having a higher H/K ratio than a reference ratio. Provided herein are also methods of predicting responsiveness of a subject having SCC to an FTI treatment based on the H/K ratio, wherein a subject is predicted to be likely responsive if the subject has a higher H/K ratio than a reference ratio. In some embodiments, the methods include analyzing a sample from the subject to measure the expression levels of H-Ras and K-Ras in the sample, and selecting the subject for an FTI treatment if the subject has a higher H/K ratio than a reference ratio. The reference ratio can be determined by a person of ordinary skill in the art through statistical analysis. In some embodiments, the reference ratio is the median H/K ratio in a population of healthy subjects. In some embodiments, the reference ratio is the median H/K ratio in a population of subjects having SCC.

Provided herein are also methods for treating SCC in a subject by administering a therapeutically effective amount of an FTI to the subject that has a higher H/N ratio than a reference ratio. Provided herein are also methods for increasing the responsiveness of an FTI treatment for SCC by selectively treating SCC patients having a higher H/N ratio than a reference ratio. Provided herein are also methods of predicting responsiveness of a subject having SCC to an FTI treatment based on the H/N ratio, wherein a subject is predicted to be likely responsive if the subject has a higher H/N ratio than a reference ratio. In some embodiments, the methods include analyzing a sample from the subject to measure the expression levels of H-Ras and N-Ras in the sample, and selecting the subject for an FTI treatment if the subject has a higher H/N ratio than a reference ratio. The reference ratio can be determined by a person of ordinary skill in the art through statistical analysis. In some embodiments, the reference ratio is the median H/N ratio in a population of healthy subjects. In some embodiments, the reference ratio is the median H/N ratio in a population of subjects having SCC.

Provided herein are also methods for treating SCC in a subject by administering a therapeutically effective amount of an FTI to the subject that has a higher H/K+N ratio than a reference ratio. Provided herein are also methods for increasing the responsiveness of an FTI treatment for SCC by selectively treating SCC patients having a higher H/K+N ratio than a reference ratio. Provided herein are also methods of predicting responsiveness of a subject having SCC to an FTI treatment based on the H/K+N ratio, wherein a subject is predicted to be likely responsive if the subject has a higher H/K+N ratio than a reference ratio. In some embodiments, the methods include analyzing a sample from the subject to measure the expression levels of H-Ras, K-Ras and N-Ras in the sample, and selecting the subject for an FTI treatment if the subject has a higher H/K+N ratio than a reference ratio. The reference ratio can be determined by a person of ordinary skill in the art through statistical analysis. In some embodiments, the reference ratio is the median H/K+N ratio in a population of healthy subjects. In some embodiments, the reference ratio is the median H/K+N ratio in a population of subjects having SCC.

In some embodiments, the reference ratio is 1/10, 1/9, 1/8, 1/7, 1/6, 1/5, 1/4, 1/3, 1/2, 1, 2, 3, 4, 5, 6, 7, 8, 9, 10, or any numeric value between 1/10 and 10. In some embodiments, the reference ratio is 1/10. In some embodiments, the reference ratio is 1/9. In some embodiments, the reference ratio is 1/8. In some embodiments, the reference ratio is 1/7. In some embodiments, the reference ratio is 1/6. In some embodiments, the reference ratio is 1/5. In some embodiments, the reference ratio is 1/4. In some embodiments, the reference ratio is 1/3. In some embodiments, the reference ratio is 1/2. In some embodiments, the reference ratio is 1. In some embodiments, the reference ratio is 2. In some embodiments, the reference ratio is 3. In some embodiments, the reference ratio is 4. In some embodiments, the reference ratio is 5. In some embodiments, the reference ratio is 6. In some embodiments, the reference ratio is 7. In some embodiments, the reference ratio is 8. In some embodiments, the reference ratio is 9. In some embodiments, the reference ratio is 10.

The FTI can be any FTI, including those described herein. For example, the FTI can be tipifarnib, lonafarnib, arglabin, perrilyl alcohol, L778123, L739749, FTI-277, L744832, CP-609,754, R208176, AZD3409, or BMS-214662. In some embodiments, the FTI is tipifarnib. Accordingly, provided herein are also methods for treating SCC in a subject by administering a therapeutically effective amount of tipifarnib to the subject that has a higher H/K ratio than a reference ratio. Provided herein are also methods for increasing the responsiveness of tipifarnib treatment for SCC by selectively treating SCC patients having a higher H/K ratio than a reference ratio. Provided herein are also methods of predicting responsiveness of a subject having SCC to tipifarnib treatment based on the H/K ratio, wherein a subject is predicted to be likely responsive if the subject has a higher H/K ratio than a reference ratio. In some embodiments, the methods include analyzing a sample from the subject to measure the expression levels of H-Ras and K-Ras in the sample, and selecting the subject for tipifarnib treatment if the subject has a higher H/K ratio than a reference ratio. The reference ratio can be determined by a person of ordinary skill in the art through statistical analysis. In some embodiments, the reference ratio is the median H/K ratio in a population of healthy subjects. In some embodiments, the reference ratio is the median H/K ratio in a population of subjects having SCC.

Provided herein are also methods for treating SCC in a subject by administering a therapeutically effective amount of tipifarnib to the subject that has a higher H/N ratio than a reference ratio. Provided herein are also methods for increasing the responsiveness of tipifarnib treatment for SCC by selectively treating SCC patients having a higher H/N ratio than a reference ratio. Provided herein are also methods of predicting responsiveness of a subject having SCC to tipifarnib treatment based on the H/N ratio, wherein a subject is predicted to be likely responsive if the subject has a higher H/N ratio than a reference ratio. In some embodiments, the methods include analyzing a sample from the subject to measure the expression levels of H-Ras and N-Ras in the sample, and selecting the subject for tipifarnib treatment if the subject has a higher H/N ratio than a reference ratio. The reference ratio can be determined by a person of ordinary skill in the art through statistical analysis. In some embodiments, the reference ratio is the median H/N ratio in a population of healthy subjects. In some embodiments, the reference ratio is the median H/N ratio in a population of subjects having SCC.

Provided herein are also methods for treating SCC in a subject by administering a therapeutically effective amount of tipifarnib to the subject that has a higher H/K+N ratio than a reference ratio. Provided herein are also methods for increasing the responsiveness of tipifarnib treatment for SCC by selectively treating SCC patients having a higher H/K+N ratio than a reference ratio. Provided herein are also methods of predicting responsiveness of a subject having SCC to tipifarnib treatment based on the H/K+N ratio, wherein a subject is predicted to be likely responsive if the subject has a higher H/K+N ratio than a reference ratio. In some embodiments, the methods include analyzing a sample from the subject to measure the expression levels of H-Ras, K-Ras and N-Ras in the sample, and selecting the subject for tipifarnib treatment if the subject has a higher H/K+N ratio than a reference ratio. The reference ratio can be determined by a person of ordinary skill in the art through statistical analysis. In some embodiments, the reference ratio is the median H/K+N ratio in a population of healthy subjects. In some embodiments, the reference ratio is the median H/K+N ratio in a population of subjects having SCC.

In some embodiments, the reference ratio is 1/10, 1/9, 1/8, 1/7, 1/6, 1/5, 1/4, 1/3, 1/2, 1, 2, 3, 4, 5, 6, 7, 8, 9, 10, or any numeric value between 1/10 and 10.

In some embodiments, the SCC is human papillomavirus (HPV)-negative. In some embodiments, the SCC is at an advanced stage. In some embodiments, the SCC is metastatic SCC. In some embodiments, the SCC is relapsed SCC. In some embodiments, the SCC is refractory. The SCC can be a specific type of SCC. For example, the SCC can head and neck SCC (HNSCC), lung SCC (LSCC), thyroid SCC, esophagus SCC, bladder SCC or urothelial carinoma (UC).

Provided herein are also methods for treating HNSCC in a subject by administering a therapeutically effective amount of an FTI to the subject that has a higher H/K ratio than a reference ratio. Provided herein are also methods for increasing the responsiveness of an FTI treatment for HNSCC by selectively treating HNSCC patients having a higher H/K ratio than a reference ratio. Provided herein are also methods of predicting responsiveness of a subject having HNSCC to an FTI treatment based on the H/K ratio, wherein a subject is predicted to be likely responsive if the subject has a higher H/K ratio than a reference ratio. In some embodiments, the methods include analyzing a sample from the subject to measure the expression levels of H-Ras and K-Ras in the sample, and selecting the subject for an FTI treatment if the subject has a higher H/K ratio than a reference ratio. The reference ratio can be determined by a person of ordinary skill in the art through statistical analysis. In some embodiments, the reference ratio is the median H/K ratio in a population of healthy subjects. In some embodiments, the reference ratio is the median H/K ratio in a population of subjects having HNSCC.

Provided herein are also methods for treating HNSCC in a subject by administering a therapeutically effective amount of an FTI to the subject that has a higher H/N ratio than a reference ratio. Provided herein are also methods for increasing the responsiveness of an FTI treatment for HNSCC by selectively treating HNSCC patients having a higher H/N ratio than a reference ratio. Provided herein are also methods of predicting responsiveness of a subject having HNSCC to an FTI treatment based on the H/N ratio, wherein a subject is predicted to be likely responsive if the subject has a higher H/N ratio than a reference ratio. In some embodiments, the methods include analyzing a sample from the subject to measure the expression levels of H-Ras and N-Ras in the sample, and selecting the subject for an FTI treatment if the subject has a higher H/N ratio than a reference ratio. The reference ratio can be determined by a person of ordinary skill in the art through statistical analysis. In some embodiments, the reference ratio is the median H/N ratio in a population of healthy subjects. In some embodiments, the reference ratio is the median H/N ratio in a population of subjects having HNSCC.

Provided herein are also methods for treating HNSCC in a subject by administering a therapeutically effective amount of an FTI to the subject that has a higher H/K+N ratio than a reference ratio. Provided herein are also methods for increasing the responsiveness of an FTI treatment for HNSCC by selectively treating HNSCC patients having a higher H/K+N ratio than a reference ratio. Provided herein are also methods of predicting responsiveness of a subject having HNSCC to an FTI treatment based on the H/K+N ratio, wherein a subject is predicted to be likely responsive if the subject has a higher H/K+N ratio than a reference ratio. In some embodiments, the methods include analyzing a sample from the subject to measure the expression levels of H-Ras, K-Ras and N-Ras in the sample, and selecting the subject for an FTI treatment if the subject has a higher H/K+N ratio than a reference ratio. The reference ratio can be determined by a person of ordinary skill in the art through statistical analysis. In some embodiments, the reference ratio is the median H/K+N ratio in a population of healthy subjects. In some embodiments, the reference ratio is the median H/K+N ratio in a population of subjects having HNSCC.

In some embodiments, the reference ratio is 1/10, 1/9, 1/8, 1/7, 1/6, 1/5, 1/4, 1/3, 1/2, 1, 2, 3, 4, 5, 6, 7, 8, 9, 10, or any numeric value between 1/10 and 10. In some embodiments, the reference ratio is 1/10.

The FTI can be any FTI, including those described herein. For example, the FTI can be tipifarnib, lonafarnib, arglabin, perrilyl alcohol, L778123, L739749, FTI-277, L744832, CP-609,754, R208176, AZD3409, or BMS-214662. In some embodiments, the FTI is tipifarnib. Accordingly, provided herein are also methods for treating HNSCC in a subject by administering a therapeutically effective amount of tipifarnib to the subject that has a higher H/K ratio than a reference ratio. Provided herein are also methods for increasing the responsiveness of tipifarnib treatment for HNSCC by selectively treating HNSCC patients having a higher H/K ratio than a reference ratio. Provided herein are also methods of predicting responsiveness of a subject having HNSCC to tipifarnib treatment based on the H/K ratio, wherein a subject is predicted to be likely responsive if the subject has a higher H/K ratio than a reference ratio. In some embodiments, the methods include analyzing a sample from the subject to measure the expression levels of H-Ras and K-Ras in the sample, and selecting the subject for tipifarnib treatment if the subject has a higher H/K ratio than a reference ratio. In some embodiments, the reference ratio is the median H/K ratio in a population of healthy subjects. In some embodiments, the reference ratio is the median H/K ratio in a population of subjects having HNSCC.

Provided herein are also methods for treating HNSCC in a subject by administering a therapeutically effective amount of tipifarnib to the subject that has a higher H/N ratio than a reference ratio. Provided herein are also methods for increasing the responsiveness of tipifarnib treatment for HNSCC by selectively treating HNSCC patients having a higher H/N ratio than a reference ratio. Provided herein are also methods of predicting responsiveness of a subject having HNSCC to tipifarnib treatment based on the H/N ratio, wherein a subject is predicted to be likely responsive if the subject has a higher H/N ratio than a reference ratio. In some embodiments, the methods include analyzing a sample from the subject to measure the expression levels of H-Ras and N-Ras in the sample, and selecting the subject for tipifarnib treatment if the subject has a higher H/N ratio than a reference ratio. In some embodiments, the reference ratio is the median H/N ratio in a population of healthy subjects. In some embodiments, the reference ratio is the median H/N ratio in a population of subjects having HNSCC.

Provided herein are also methods for treating HNSCC in a subject by administering a therapeutically effective amount of tipifarnib to the subject that has a higher H/K+N ratio than a reference ratio. Provided herein are also methods for increasing the responsiveness of tipifarnib treatment for HNSCC by selectively treating HNSCC patients having a higher H/K+N ratio than a reference ratio. Provided herein are also methods of predicting responsiveness of a subject having HNSCC to tipifarnib treatment based on the H/K+N ratio, wherein a subject is predicted to be likely responsive if the subject has a higher H/K+N ratio than a reference ratio. In some embodiments, the methods include analyzing a sample from the subject to measure the expression levels of H-Ras, K-Ras and N-Ras in the sample, and selecting the subject for tipifarnib treatment if the subject has a higher H/K+N ratio than a reference ratio. The reference ratio can be determined by a person of ordinary skill in the art through statistical analysis. In some embodiments, the reference ratio is the median H/K+N ratio in a population of healthy subjects. In some embodiments, the reference ratio is the median H/K+N ratio in a population of subjects having HNSCC.

In some embodiments, the reference ratio is 1/10, 1/9, 1/8, 1/7, 1/6, 1/5, 1/4, 1/3, 1/2, 1, 2, 3, 4, 5, 6, 7, 8, 9, 10, or any numeric value between 1/10 and 10.

In some embodiments, the HNSCC is HNSCC of the trachea. In some embodiments, the HNSCC is HNSCC of the maxilla. In some embodiments, the HNSCC is HNSCC of the oral cavity. In some embodiments, the HNSCC is human papillomavirus (HPV)-negative HNSCC. In some embodiments, the HNSCC is at an advanced stage. In some embodiments, the HNSCC is metastatic HNSCC. In some embodiments, the HNSCC is relapsed HNSCC. In some embodiments, the HNSCC is refractory HNSCC.

Provided herein are also methods for treating LSCC in a subject by administering a therapeutically effective amount of an FTI to the subject that has a higher H/K ratio than a reference ratio. Provided herein are also methods for increasing the responsiveness of an FTI treatment for LSCC by selectively treating LSCC patients having a higher H/K ratio than a reference ratio. Provided herein are also methods of predicting responsiveness of a subject having LSCC to an FTI treatment based on the H/K ratio, wherein a subject is predicted to be likely responsive if the subject has a higher H/K ratio than a reference ratio. In some embodiments, the methods include analyzing a sample from the subject to measure the expression levels of H-Ras and K-Ras in the sample, and selecting the subject for an FTI treatment if the subject has a higher H/K ratio than a reference ratio. The reference ratio can be determined by a person of ordinary skill in the art through statistical analysis. In some embodiments, the reference ratio is the median H/K ratio in a population of healthy subjects. In some embodiments, the reference ratio is the median H/K ratio in a population of subjects having LSCC.

Provided herein are also methods for treating LSCC in a subject by administering a therapeutically effective amount of an FTI to the subject that has a higher H/N ratio than a reference ratio. Provided herein are also methods for increasing the responsiveness of an FTI treatment for LSCC by selectively treating LSCC patients having a higher H/N ratio than a reference ratio. Provided herein are also methods of predicting responsiveness of a subject having LSCC to an FTI treatment based on the H/N ratio, wherein a subject is predicted to be likely responsive if the subject has a higher H/N ratio than a reference ratio. In some embodiments, the methods include analyzing a sample from the subject to measure the expression levels of H-Ras and N-Ras in the sample, and selecting the subject for an FTI treatment if the subject has a higher H/N ratio than a reference ratio. The reference ratio can be determined by a person of ordinary skill in the art through statistical analysis. In some embodiments, the reference ratio is the median H/N ratio in a population of healthy subjects. In some embodiments, the reference ratio is the median H/N ratio in a population of subjects having LSCC.

Provided herein are also methods for treating LSCC in a subject by administering a therapeutically effective amount of an FTI to the subject that has a higher H/K+N ratio than a reference ratio. Provided herein are also methods for increasing the responsiveness of an FTI treatment for LSCC by selectively treating LSCC patients having a higher H/K+N ratio than a reference ratio. Provided herein are also methods of predicting responsiveness of a subject having LSCC to an FTI treatment based on the H/K+N ratio, wherein a subject is predicted to be likely responsive if the subject has a higher H/K+N ratio than a reference ratio. In some embodiments, the methods include analyzing a sample from the subject to measure the expression levels of H-Ras, K-Ras and N-Ras in the sample, and selecting the subject for an FTI treatment if the subject has a higher H/K+N ratio than a reference ratio. The reference ratio can be determined by a person of ordinary skill in the art through statistical analysis. In some embodiments, the reference ratio is the median H/K+N ratio in a population of healthy subjects. In some embodiments, the reference ratio is the median H/K+N ratio in a population of subjects having LSCC.

In some embodiments, the reference ratio is 1/10, 1/9, 1/8, 1/7, 1/6, 1/5, 1/4, 1/3, 1/2, 1, 2, 3, 4, 5, 6, 7, 8, 9, 10, or any numeric value between 1/10 and 10.

In some embodiments, the LSCC is human papillomavirus (HPV)-negative LSCC. In some embodiments, the LSCC is at an advanced stage. In some embodiments, the LSCC is metastatic LSCC. In some embodiments, the LSCC is relapsed LSCC. In some embodiments, the LSCC is refractory LSCC.

The FTI can be any FTI, including those described herein. For example, the FTI can be tipifarnib, lonafarnib, arglabin, perrilyl alcohol, L778123, L739749, FTI-277, L744832, CP-609,754, R208176, AZD3409, or BMS-214662. In some embodiments, the FTI is tipifarnib. Accordingly, provided herein are also methods for treating LSCC in a subject by administering a therapeutically effective amount of tipifarnib to the subject that has a higher H/K ratio than a reference ratio. Provided herein are also methods for increasing the responsiveness of tipifarnib treatment for LSCC by selectively treating LSCC patients having a higher H/K ratio than a reference ratio. Provided herein are also methods of predicting responsiveness of a subject having LSCC to tipifarnib treatment based on the H/K ratio, wherein a subject is predicted to be likely responsive if the subject has a higher H/K ratio than a reference ratio. In some embodiments, the methods include analyzing a sample from the subject to measure the expression levels of H-Ras and K-Ras in the sample, and selecting the subject for tipifarnib treatment if the subject has a higher H/K ratio than a reference ratio. In some embodiments, the reference ratio is the median H/K ratio in a population of healthy subjects. In some embodiments, the reference ratio is the median H/K ratio in a population of subjects having LSCC.

Provided herein are also methods for treating LSCC in a subject by administering a therapeutically effective amount of tipifarnib to the subject that has a higher H/N ratio than a reference ratio. Provided herein are also methods for increasing the responsiveness of tipifarnib treatment for LSCC by selectively treating LSCC patients having a higher H/N ratio than a reference ratio. Provided herein are also methods of predicting responsiveness of a subject having LSCC to tipifarnib treatment based on the H/N ratio, wherein a subject is predicted to be likely responsive if the subject has a higher H/N ratio than a reference ratio. In some embodiments, the methods include analyzing a sample from the subject to measure the expression levels of H-Ras and N-Ras in the sample, and selecting the subject for tipifarnib treatment if the subject has a higher H/N ratio than a reference ratio. In some embodiments, the reference ratio is the median H/N ratio in a population of healthy subjects. In some embodiments, the reference ratio is the median H/N ratio in a population of subjects having LSCC.

Provided herein are also methods for treating LSCC in a subject by administering a therapeutically effective amount of tipifarnib to the subject that has a higher H/K+N ratio than a reference ratio. Provided herein are also methods for increasing the responsiveness of tipifarnib treatment for LSCC by selectively treating LSCC patients having a higher H/K+N ratio than a reference ratio. Provided herein are also methods of predicting responsiveness of a subject having LSCC to tipifarnib treatment based on the H/K+N ratio, wherein a subject is predicted to be likely responsive if the subject has a higher H/K+N ratio than a reference ratio. In some embodiments, the methods include analyzing a sample from the subject to measure the expression levels of H-Ras, K-Ras and N-Ras in the sample, and selecting the subject for tipifarnib treatment if the subject has a higher H/K+N ratio than a reference ratio. The reference ratio can be determined by a person of ordinary skill in the art through statistical analysis. In some embodiments, the reference ratio is the median H/K+N ratio in a population of healthy subjects. In some embodiments, the reference ratio is the median H/K+N ratio in a population of subjects having LSCC.

In some embodiments, the reference ratio is 1/10, 1/9, 1/8, 1/7, 1/6, 1/5, 1/4, 1/3, 1/2, 1, 2, 3, 4, 5, 6, 7, 8, 9, 10, or any numeric value between 1/10 and 10.

In some embodiments, the LSCC is human papillomavirus (HPV)-negative LSCC. In some embodiments, the LSCC is at an advanced stage. In some embodiments, the LSCC is metastatic LSCC. In some embodiments, the LSCC is relapsed LSCC. In some embodiments, the LSCC is refractory LSCC.

Provided herein are also methods for treating thyroid SCC in a subject by administering a therapeutically effective amount of an FTI to the subject that has a higher H/K ratio than a reference ratio. Provided herein are also methods for increasing the responsiveness of an FTI treatment for thyroid SCC by selectively treating thyroid SCC patients having a higher H/K ratio than a reference ratio. Provided herein are also methods of predicting responsiveness of a subject having thyroid SCC to an FTI treatment based on the H/K ratio, wherein a subject is predicted to be likely responsive if the subject has a higher H/K ratio than a reference ratio. In some embodiments, the methods include analyzing a sample from the subject to measure the expression levels of H-Ras and K-Ras in the sample, and selecting the subject for an FTI treatment if the subject has a higher H/K ratio than a reference ratio. The reference ratio can be determined by a person of ordinary skill in the art through statistical analysis. In some embodiments, the reference ratio is the median H/K ratio in a population of healthy subjects. In some embodiments, the reference ratio is the median H/K ratio in a population of subjects having thyroid SCC.

Provided herein are also methods for treating thyroid SCC in a subject by administering a therapeutically effective amount of an FTI to the subject that has a higher H/N ratio than a reference ratio. Provided herein are also methods for increasing the responsiveness of an FTI treatment for thyroid SCC by selectively treating thyroid SCC patients having a higher H/N ratio than a reference ratio. Provided herein are also methods of predicting responsiveness of a subject having thyroid SCC to an FTI treatment based on the H/N ratio, wherein a subject is predicted to be likely responsive if the subject has a higher H/N ratio than a reference ratio. In some embodiments, the methods include analyzing a sample from the subject to measure the expression levels of H-Ras and N-Ras in the sample, and selecting the subject for an FTI treatment if the subject has a higher H/N ratio than a reference ratio. The reference ratio can be determined by a person of ordinary skill in the art through statistical analysis. In some embodiments, the reference ratio is the median H/N ratio in a population of healthy subjects. In some embodiments, the reference ratio is the median H/N ratio in a population of subjects having thyroid SCC.

Provided herein are also methods for treating thyroid SCC in a subject by administering a therapeutically effective amount of an FTI to the subject that has a higher H/K+N ratio than a reference ratio. Provided herein are also methods for increasing the responsiveness of an FTI treatment for thyroid SCC by selectively treating thyroid SCC patients having a higher H/K+N ratio than a reference ratio. Provided herein are also methods of predicting responsiveness of a subject having thyroid SCC to an FTI treatment based on the H/K+N ratio, wherein a subject is predicted to be likely responsive if the subject has a higher H/K+N ratio than a reference ratio. In some embodiments, the methods include analyzing a sample from the subject to measure the expression levels of H-Ras, K-Ras and N-Ras in the sample, and selecting the subject for an FTI treatment if the subject has a higher H/K+N ratio than a reference ratio. The reference ratio can be determined by a person of ordinary skill in the art through statistical analysis. In some embodiments, the reference ratio is the median H/K+N ratio in a population of healthy subjects. In some embodiments, the reference ratio is the median H/K+N ratio in a population of subjects having thyroid SCC.

In some embodiments, the reference ratio is 1/10, 1/9, 1/8, 1/7, 1/6, 1/5, 1/4, 1/3, 1/2, 1, 2, 3, 4, 5, 6, 7, 8, 9, 10, or any numeric value between 1/10 and 10.

In some embodiments, the thyroid SCC is human papillomavirus (HPV)-negative thyroid SCC. In some embodiments, the thyroid SCC is at an advanced stage. In some embodiments, the thyroid SCC is metastatic thyroid SCC. In some embodiments, the thyroid SCC is relapsed thyroid SCC. In some embodiments, the thyroid SCC is refractory thyroid SCC.

The FTI can be any FTI, including those described herein. For example, the FTI can be tipifarnib, lonafarnib, arglabin, perrilyl alcohol, L778123, L739749, FTI-277, L744832, CP-609,754, R208176, AZD3409, or BMS-214662. In some embodiments, the FTI is tipifarnib. Accordingly, provided herein are also methods for treating thyroid SCC in a subject by administering a therapeutically effective amount of tipifarnib to the subject that has a higher H/K ratio than a reference ratio. Provided herein are also methods for increasing the responsiveness of tipifarnib treatment for thyroid SCC by selectively treating thyroid SCC patients having a higher H/K ratio than a reference ratio. Provided herein are also methods of predicting responsiveness of a subject having thyroid SCC to tipifarnib treatment based on the H/K ratio, wherein a subject is predicted to be likely responsive if the subject has a higher H/K ratio than a reference ratio. In some embodiments, the methods include analyzing a sample from the subject to measure the expression levels of H-Ras and K-Ras in the sample, and selecting the subject for tipifarnib treatment if the subject has a higher H/K ratio than a reference ratio. In some embodiments, the reference ratio is the median H/K ratio in a population of healthy subjects. In some embodiments, the reference ratio is the median H/K ratio in a population of subjects having thyroid SCC.

Provided herein are also methods for treating thyroid SCC in a subject by administering a therapeutically effective amount of tipifarnib to the subject that has a higher H/N ratio than a reference ratio. Provided herein are also methods for increasing the responsiveness of tipifarnib treatment for thyroid SCC by selectively treating thyroid SCC patients having a higher H/N ratio than a reference ratio. Provided herein are also methods of predicting responsiveness of a subject having thyroid SCC to tipifarnib treatment based on the H/N ratio, wherein a subject is predicted to be likely responsive if the subject has a higher H/N ratio than a reference ratio. In some embodiments, the methods include analyzing a sample from the subject to measure the expression levels of H-Ras and N-Ras in the sample, and selecting the subject for tipifarnib treatment if the subject has a higher H/N ratio than a reference ratio. In some embodiments, the reference ratio is the median H/N ratio in a population of healthy subjects. In some embodiments, the reference ratio is the median H/N ratio in a population of subjects having thyroid SCC.

Provided herein are also methods for treating thyroid SCC in a subject by administering a therapeutically effective amount of tipifarnib to the subject that has a higher H/K+N ratio than a reference ratio. Provided herein are also methods for increasing the responsiveness of tipifarnib treatment for thyroid SCC by selectively treating thyroid SCC patients having a higher H/K+N ratio than a reference ratio. Provided herein are also methods of predicting responsiveness of a subject having thyroid SCC to tipifarnib treatment based on the H/K+N ratio, wherein a subject is predicted to be likely responsive if the subject has a higher H/K+N ratio than a reference ratio. In some embodiments, the methods include analyzing a sample from the subject to measure the expression levels of H-Ras, K-Ras and N-Ras in the sample, and selecting the subject for tipifarnib treatment if the subject has a higher H/K+N ratio than a reference ratio. The reference ratio can be determined by a person of ordinary skill in the art through statistical analysis. In some embodiments, the reference ratio is the median H/K+N ratio in a population of healthy subjects. In some embodiments, the reference ratio is the median H/K+N ratio in a population of subjects having thyroid SCC.

In some embodiments, the reference ratio is 1/10, 1/9, 1/8, 1/7, 1/6, 1/5, 1/4, 1/3, 1/2, 1, 2, 3, 4, 5, 6, 7, 8, 9, 10, or any numeric value between 1/10 and 10.

In some embodiments, the thyroid SCC is human papillomavirus (HPV)-negative thyroid SCC. In some embodiments, the thyroid SCC is at an advanced stage. In some embodiments, the thyroid SCC is metastatic thyroid SCC. In some embodiments, the thyroid SCC is relapsed thyroid SCC. In some embodiments, the thyroid SCC is refractory thyroid SCC.

Provided herein are also methods for treating esophagus SCC in a subject by administering a therapeutically effective amount of an FTI to the subject that has a higher H/K ratio than a reference ratio. Provided herein are also methods for increasing the responsiveness of an FTI treatment for esophagus SCC by selectively treating esophagus SCC patients having a higher H/K ratio than a reference ratio. Provided herein are also methods of predicting responsiveness of a subject having esophagus SCC to an FTI treatment based on the H/K ratio, wherein a subject is predicted to be likely responsive if the subject has a higher H/K ratio than a reference ratio. In some embodiments, the methods include analyzing a sample from the subject to measure the expression levels of H-Ras and K-Ras in the sample, and selecting the subject for an FTI treatment if the subject has a higher H/K ratio than a reference ratio. The reference ratio can be determined by a person of ordinary skill in the art through statistical analysis. In some embodiments, the reference ratio is the median H/K ratio in a population of healthy subjects. In some embodiments, the reference ratio is the median H/K ratio in a population of subjects having esophagus SCC.

Provided herein are also methods for treating esophagus SCC in a subject by administering a therapeutically effective amount of an FTI to the subject that has a higher H/N ratio than a reference ratio. Provided herein are also methods for increasing the responsiveness of an FTI treatment for esophagus SCC by selectively treating esophagus SCC patients having a higher H/N ratio than a reference ratio. Provided herein are also methods of predicting responsiveness of a subject having esophagus SCC to an FTI treatment based on the H/N ratio, wherein a subject is predicted to be likely responsive if the subject has a higher H/N ratio than a reference ratio. In some embodiments, the methods include analyzing a sample from the subject to measure the expression levels of H-Ras and N-Ras in the sample, and selecting the subject for an FTI treatment if the subject has a higher H/N ratio than a reference ratio. The reference ratio can be determined by a person of ordinary skill in the art through statistical analysis. In some embodiments, the reference ratio is the median H/N ratio in a population of healthy subjects. In some embodiments, the reference ratio is the median H/N ratio in a population of subjects having esophagus SCC.

Provided herein are also methods for treating esophagus SCC in a subject by administering a therapeutically effective amount of an FTI to the subject that has a higher H/K+N ratio than a reference ratio. Provided herein are also methods for increasing the responsiveness of an FTI treatment for esophagus SCC by selectively treating esophagus SCC patients having a higher H/K+N ratio than a reference ratio. Provided herein are also methods of predicting responsiveness of a subject having esophagus SCC to an FTI treatment based on the H/K+N ratio, wherein a subject is predicted to be likely responsive if the subject has a higher H/K+N ratio than a reference ratio. In some embodiments, the methods include analyzing a sample from the subject to measure the expression levels of H-Ras, K-Ras and N-Ras in the sample, and selecting the subject for an FTI treatment if the subject has a higher H/K+N ratio than a reference ratio. The reference ratio can be determined by a person of ordinary skill in the art through statistical analysis. In some embodiments, the reference ratio is the median H/K+N ratio in a population of healthy subjects. In some embodiments, the reference ratio is the median H/K+N ratio in a population of subjects having esophagus SCC.

In some embodiments, the reference ratio is 1/10, 1/9, 1/8, 1/7, 1/6, 1/5, 1/4, 1/3, 1/2, 1, 2, 3, 4, 5, 6, 7, 8, 9, 10, or any numeric value between 1/10 and 10.

In some embodiments, the esophagus SCC is human papillomavirus (HPV)-negative esophagus SCC. In some embodiments, the esophagus SCC is at an advanced stage. In some embodiments, the esophagus SCC is metastatic esophagus SCC. In some embodiments, the esophagus SCC is relapsed esophagus SCC. In some embodiments, the esophagus SCC is refractory esophagus SCC.

The FTI can be any FTI, including those described herein. For example, the FTI can be tipifarnib, lonafarnib, arglabin, perrilyl alcohol, L778123, L739749, FTI-277, L744832, CP-609,754, R208176, AZD3409, or BMS-214662. In some embodiments, the FTI is tipifarnib. Accordingly, provided herein are also methods for treating esophagus SCC in a subject by administering a therapeutically effective amount of tipifarnib to the subject that has a higher H/K ratio than a reference ratio. Provided herein are also methods for increasing the responsiveness of tipifarnib treatment for esophagus SCC by selectively treating esophagus SCC patients having a higher H/K ratio than a reference ratio. Provided herein are also methods of predicting responsiveness of a subject having esophagus SCC to tipifarnib treatment based on the H/K ratio, wherein a subject is predicted to be likely responsive if the subject has a higher H/K ratio than a reference ratio. In some embodiments, the methods include analyzing a sample from the subject to measure the expression levels of H-Ras and K-Ras in the sample, and selecting the subject for tipifarnib treatment if the subject has a higher H/K ratio than a reference ratio. In some embodiments, the reference ratio is the median H/K ratio in a population of healthy subjects. In some embodiments, the reference ratio is the median H/K ratio in a population of subjects having esophagus SCC.

Provided herein are also methods for treating esophagus SCC in a subject by administering a therapeutically effective amount of tipifarnib to the subject that has a higher H/N ratio than a reference ratio. Provided herein are also methods for increasing the responsiveness of tipifarnib treatment for esophagus SCC by selectively treating esophagus SCC patients having a higher H/N ratio than a reference ratio. Provided herein are also methods of predicting responsiveness of a subject having esophagus SCC to tipifarnib treatment based on the H/N ratio, wherein a subject is predicted to be likely responsive if the subject has a higher H/N ratio than a reference ratio. In some embodiments, the methods include analyzing a sample from the subject to measure the expression levels of H-Ras and N-Ras in the sample, and selecting the subject for tipifarnib treatment if the subject has a higher H/N ratio than a reference ratio. In some embodiments, the reference ratio is the median H/N ratio in a population of healthy subjects. In some embodiments, the reference ratio is the median H/N ratio in a population of subjects having esophagus SCC.

Provided herein are also methods for treating esophagus SCC in a subject by administering a therapeutically effective amount of tipifarnib to the subject that has a higher H/K+N ratio than a reference ratio. Provided herein are also methods for increasing the responsiveness of tipifarnib treatment for esophagus SCC by selectively treating esophagus SCC patients having a higher H/K+N ratio than a reference ratio. Provided herein are also methods of predicting responsiveness of a subject having esophagus SCC to tipifarnib treatment based on the H/K+N ratio, wherein a subject is predicted to be likely responsive if the subject has a higher H/K+N ratio than a reference ratio. In some embodiments, the methods include analyzing a sample from the subject to measure the expression levels of H-Ras, K-Ras and N-Ras in the sample, and selecting the subject for tipifarnib treatment if the subject has a higher H/K+N ratio than a reference ratio. The reference ratio can be determined by a person of ordinary skill in the art through statistical analysis. In some embodiments, the reference ratio is the median H/K+N ratio in a population of healthy subjects. In some embodiments, the reference ratio is the median H/K+N ratio in a population of subjects having esophagus SCC.

In some embodiments, the reference ratio is 1/10, 1/9, 1/8, 1/7, 1/6, 1/5, 1/4, 1/3, 1/2, 1, 2, 3, 4, 5, 6, 7, 8, 9, 10, or any numeric value between 1/10 and 10.

In some embodiments, the esophagus SCC is human papillomavirus (HPV)-negative esophagus SCC. In some embodiments, the esophagus SCC is at an advanced stage. In some embodiments, the esophagus SCC is metastatic esophagus SCC. In some embodiments, the esophagus SCC is relapsed esophagus SCC. In some embodiments, the esophagus SCC is refractory esophagus SCC.

Provided herein are also methods for treating bladder SCC in a subject by administering a therapeutically effective amount of an FTI to the subject that has a higher H/K ratio than a reference ratio. Provided herein are also methods for increasing the responsiveness of an FTI treatment for bladder SCC by selectively treating bladder SCC patients having a higher H/K ratio than a reference ratio. Provided herein are also methods of predicting responsiveness of a subject having bladder SCC to an FTI treatment based on the H/K ratio, wherein a subject is predicted to be likely responsive if the subject has a higher H/K ratio than a reference ratio. In some embodiments, the methods include analyzing a sample from the subject to measure the expression levels of H-Ras and K-Ras in the sample, and selecting the subject for an FTI treatment if the subject has a higher H/K ratio than a reference ratio. The reference ratio can be determined by a person of ordinary skill in the art through statistical analysis. In some embodiments, the reference ratio is the median H/K ratio in a population of healthy subjects. In some embodiments, the reference ratio is the median H/K ratio in a population of subjects having bladder SCC.

Provided herein are also methods for treating bladder SCC in a subject by administering a therapeutically effective amount of an FTI to the subject that has a higher H/N ratio than a reference ratio. Provided herein are also methods for increasing the responsiveness of an FTI treatment for bladder SCC by selectively treating bladder SCC patients having a higher H/N ratio than a reference ratio. Provided herein are also methods of predicting responsiveness of a subject having bladder SCC to an FTI treatment based on the H/N ratio, wherein a subject is predicted to be likely responsive if the subject has a higher H/N ratio than a reference ratio. In some embodiments, the methods include analyzing a sample from the subject to measure the expression levels of H-Ras and N-Ras in the sample, and selecting the subject for an FTI treatment if the subject has a higher H/N ratio than a reference ratio. The reference ratio can be determined by a person of ordinary skill in the art through statistical analysis. In some embodiments, the reference ratio is the median H/N ratio in a population of healthy subjects. In some embodiments, the reference ratio is the median H/N ratio in a population of subjects having bladder SCC.

Provided herein are also methods for treating bladder SCC in a subject by administering a therapeutically effective amount of an FTI to the subject that has a higher H/K+N ratio than a reference ratio. Provided herein are also methods for increasing the responsiveness of an FTI treatment for bladder SCC by selectively treating bladder SCC patients having a higher H/K+N ratio than a reference ratio. Provided herein are also methods of predicting responsiveness of a subject having bladder SCC to an FTI treatment based on the H/K+N ratio, wherein a subject is predicted to be likely responsive if the subject has a higher H/K+N ratio than a reference ratio. In some embodiments, the methods include analyzing a sample from the subject to measure the expression levels of H-Ras, K-Ras and N-Ras in the sample, and selecting the subject for an FTI treatment if the subject has a higher H/K+N ratio than a reference ratio. The reference ratio can be determined by a person of ordinary skill in the art through statistical analysis. In some embodiments, the reference ratio is the median H/K+N ratio in a population of healthy subjects. In some embodiments, the reference ratio is the median H/K+N ratio in a population of subjects having bladder SCC.

In some embodiments, the reference ratio is 1/10, 1/9, 1/8, 1/7, 1/6, 1/5, 1/4, 1/3, 1/2, 1, 2, 3, 4, 5, 6, 7, 8, 9, 10, or any numeric value between 1/10 and 10.

In some embodiments, the bladder SCC is human papillomavirus (HPV)-negative bladder SCC. In some embodiments, the bladder SCC is at an advanced stage. In some embodiments, the bladder SCC is metastatic bladder SCC. In some embodiments, the bladder SCC is relapsed bladder SCC. In some embodiments, the bladder SCC is refractory bladder SCC.

The FTI can be any FTI, including those described herein. For example, the FTI can be tipifarnib, lonafarnib, arglabin, perrilyl alcohol, L778123, L739749, FTI-277, L744832, CP-609,754, R208176, AZD3409, or BMS-214662. In some embodiments, the FTI is tipifarnib. Accordingly, provided herein are also methods for treating bladder SCC in a subject by administering a therapeutically effective amount of tipifarnib to the subject that has a higher H/K ratio than a reference ratio. Provided herein are also methods for increasing the responsiveness of tipifarnib treatment for bladder SCC by selectively treating bladder SCC patients having a higher H/K ratio than a reference ratio. Provided herein are also methods of predicting responsiveness of a subject having bladder SCC to tipifarnib treatment based on the H/K ratio, wherein a subject is predicted to be likely responsive if the subject has a higher H/K ratio than a reference ratio. In some embodiments, the methods include analyzing a sample from the subject to measure the expression levels of H-Ras and K-Ras in the sample, and selecting the subject for tipifarnib treatment if the subject has a higher H/K ratio than a reference ratio. In some embodiments, the reference ratio is the median H/K ratio in a population of healthy subjects. In some embodiments, the reference ratio is the median H/K ratio in a population of subjects having bladder SCC.

Provided herein are also methods for treating bladder SCC in a subject by administering a therapeutically effective amount of tipifarnib to the subject that has a higher H/N ratio than a reference ratio. Provided herein are also methods for increasing the responsiveness of tipifarnib treatment for bladder SCC by selectively treating bladder SCC patients having a higher H/N ratio than a reference ratio. Provided herein are also methods of predicting responsiveness of a subject having bladder SCC to tipifarnib treatment based on the H/N ratio, wherein a subject is predicted to be likely responsive if the subject has a higher H/N ratio than a reference ratio. In some embodiments, the methods include analyzing a sample from the subject to measure the expression levels of H-Ras and N-Ras in the sample, and selecting the subject for tipifarnib treatment if the subject has a higher H/N ratio than a reference ratio. In some embodiments, the reference ratio is the median H/N ratio in a population of healthy subjects. In some embodiments, the reference ratio is the median H/N ratio in a population of subjects having bladder SCC.

Provided herein are also methods for treating bladder SCC in a subject by administering a therapeutically effective amount of tipifarnib to the subject that has a higher H/K+N ratio than a reference ratio. Provided herein are also methods for increasing the responsiveness of tipifarnib treatment for bladder SCC by selectively treating bladder SCC patients having a higher H/K+N ratio than a reference ratio. Provided herein are also methods of predicting responsiveness of a subject having bladder SCC to tipifarnib treatment based on the H/K+N ratio, wherein a subject is predicted to be likely responsive if the subject has a higher H/K+N ratio than a reference ratio. In some embodiments, the methods include analyzing a sample from the subject to measure the expression levels of H-Ras, K-Ras and N-Ras in the sample, and selecting the subject for tipifarnib treatment if the subject has a higher H/K+N ratio than a reference ratio. The reference ratio can be determined by a person of ordinary skill in the art through statistical analysis. In some embodiments, the reference ratio is the median H/K+N ratio in a population of healthy subjects. In some embodiments, the reference ratio is the median H/K+N ratio in a population of subjects having bladder SCC.

In some embodiments, the reference ratio is 1/10, 1/9, 1/8, 1/7, 1/6, 1/5, 1/4, 1/3, 1/2, 1, 2, 3, 4, 5, 6, 7, 8, 9, 10, or any numeric value between 1/10 and 10.

In some embodiments, the bladder SCC is human papillomavirus (HPV)-negative bladder SCC. In some embodiments, the bladder SCC is at an advanced stage. In some embodiments, the bladder SCC is metastatic bladder SCC. In some embodiments, the bladder SCC is relapsed bladder SCC. In some embodiments, the bladder SCC is refractory bladder SCC.

Provided herein are also methods for treating urothelial carcinoma (UC) in a subject by administering a therapeutically effective amount of an FTI to the subject that has a higher H/K ratio than a reference ratio. Provided herein are also methods for increasing the responsiveness of an FTI treatment for UC by selectively treating UC patients having a higher H/K ratio than a reference ratio. Provided herein are also methods of predicting responsiveness of a subject having UC to an FTI treatment based on the H/K ratio, wherein a subject is predicted to be likely responsive if the subject has a higher H/K ratio than a reference ratio. In some embodiments, the methods include analyzing a sample from the subject to measure the expression levels of H-Ras and K-Ras in the sample, and selecting the subject for an FTI treatment if the subject has a higher H/K ratio than a reference ratio. The reference ratio can be determined by a person of ordinary skill in the art through statistical analysis. In some embodiments, the reference ratio is the median H/K ratio in a population of healthy subjects. In some embodiments, the reference ratio is the median H/K ratio in a population of subjects having UC.

Provided herein are also methods for treating UC in a subject by administering a therapeutically effective amount of an FTI to the subject that has a higher H/N ratio than a reference ratio. Provided herein are also methods for increasing the responsiveness of an FTI treatment for UC by selectively treating UC patients having a higher H/N ratio than a reference ratio. Provided herein are also methods of predicting responsiveness of a subject having UC to an FTI treatment based on the H/N ratio, wherein a subject is predicted to be likely responsive if the subject has a higher H/N ratio than a reference ratio. In some embodiments, the methods include analyzing a sample from the subject to measure the expression levels of H-Ras and N-Ras in the sample, and selecting the subject for an FTI treatment if the subject has a higher H/N ratio than a reference ratio. The reference ratio can be determined by a person of ordinary skill in the art through statistical analysis. In some embodiments, the reference ratio is the median H/N ratio in a population of healthy subjects. In some embodiments, the reference ratio is the median H/N ratio in a population of subjects having UC.

Provided herein are also methods for treating UC in a subject by administering a therapeutically effective amount of an FTI to the subject that has a higher H/K+N ratio than a reference ratio. Provided herein are also methods for increasing the responsiveness of an FTI treatment for UC by selectively treating UC patients having a higher H/K+N ratio than a reference ratio. Provided herein are also methods of predicting responsiveness of a subject having UC to an FTI treatment based on the H/K+N ratio, wherein a subject is predicted to be likely responsive if the subject has a higher H/K+N ratio than a reference ratio. In some embodiments, the methods include analyzing a sample from the subject to measure the expression levels of H-Ras, K-Ras and N-Ras in the sample, and selecting the subject for an FTI treatment if the subject has a higher H/K+N ratio than a reference ratio. The reference ratio can be determined by a person of ordinary skill in the art through statistical analysis. In some embodiments, the reference ratio is the median H/K+N ratio in a population of healthy subjects. In some embodiments, the reference ratio is the median H/K+N ratio in a population of subjects having UC.

In some embodiments, the reference ratio is 1/10, 1/9, 1/8, 1/7, 1/6, 1/5, 1/4, 1/3, 1/2, 1, 2, 3, 4, 5, 6, 7, 8, 9, 10, or any numeric value between 1/10 and 10.

In some embodiments, the UC is human papillomavirus (HPV)-negative UC. In some embodiments, the UC is at an advanced stage. In some embodiments, the UC is metastatic UC. In some embodiments, the UC is relapsed UC. In some embodiments, the UC is refractory UC.

The FTI can be any FTI, including those described herein. For example, the FTI can be tipifarnib, lonafarnib, arglabin, perrilyl alcohol, L778123, L739749, FTI-277, L744832, CP-609,754, R208176, AZD3409, or BMS-214662. In some embodiments, the FTI is tipifarnib. Accordingly, provided herein are also methods for treating UC in a subject by administering a therapeutically effective amount of tipifarnib to the subject that has a higher H/K ratio than a reference ratio. Provided herein are also methods for increasing the responsiveness of tipifarnib treatment for UC by selectively treating UC patients having a higher H/K ratio than a reference ratio. Provided herein are also methods of predicting responsiveness of a subject having UC to tipifarnib treatment based on the H/K ratio, wherein a subject is predicted to be likely responsive if the subject has a higher H/K ratio than a reference ratio. In some embodiments, the methods include analyzing a sample from the subject to measure the expression levels of H-Ras and K-Ras in the sample, and selecting the subject for tipifarnib treatment if the subject has a higher H/K ratio than a reference ratio. In some embodiments, the reference ratio is the median H/K ratio in a population of healthy subjects. In some embodiments, the reference ratio is the median H/K ratio in a population of subjects having UC.

Provided herein are also methods for treating UC in a subject by administering a therapeutically effective amount of tipifarnib to the subject that has a higher H/N ratio than a reference ratio. Provided herein are also methods for increasing the responsiveness of tipifarnib treatment for UC by selectively treating UC patients having a higher H/N ratio than a reference ratio. Provided herein are also methods of predicting responsiveness of a subject having UC to tipifarnib treatment based on the H/N ratio, wherein a subject is predicted to be likely responsive if the subject has a higher H/N ratio than a reference ratio. In some embodiments, the methods include analyzing a sample from the subject to measure the expression levels of H-Ras and N-Ras in the sample, and selecting the subject for tipifarnib treatment if the subject has a higher H/N ratio than a reference ratio. In some embodiments, the reference ratio is the median H/N ratio in a population of healthy subjects. In some embodiments, the reference ratio is the median H/N ratio in a population of subjects having UC.

Provided herein are also methods for treating UC in a subject by administering a therapeutically effective amount of tipifarnib to the subject that has a higher H/K+N ratio than a reference ratio. Provided herein are also methods for increasing the responsiveness of tipifarnib treatment for UC by selectively treating UC patients having a higher H/K+N ratio than a reference ratio. Provided herein are also methods of predicting responsiveness of a subject having UC to tipifarnib treatment based on the H/K+N ratio, wherein a subject is predicted to be likely responsive if the subject has a higher H/K+N ratio than a reference ratio. In some embodiments, the methods include analyzing a sample from the subject to measure the expression levels of H-Ras, K-Ras and N-Ras in the sample, and selecting the subject for tipifarnib treatment if the subject has a higher H/K+N ratio than a reference ratio. The reference ratio can be determined by a person of ordinary skill in the art through statistical analysis. In some embodiments, the reference ratio is the median H/K+N ratio in a population of healthy subjects. In some embodiments, the reference ratio is the median H/K+N ratio in a population of subjects having UC.

In some embodiments, the reference ratio is 1/10, 1/9, 1/8, 1/7, 1/6, 1/5, 1/4, 1/3, 1/2, 1, 2, 3, 4, 5, 6, 7, 8, 9, 10, or any numeric value between 1/10 and 10.

In some embodiments, the UC is human papillomavirus (HPV)-negative UC. In some embodiments, the UC is at an advanced stage. In some embodiments, the UC is metastatic UC. In some embodiments, the UC is relapsed UC. In some embodiments, the UC is refractory UC.

As a person of ordinary skill in the art would understand, the reference expression level of a gene or the reference ratio between expression levels of two genes can also be determined based on statistical analysis of data from previous clinical trials, including outcome of a group of patients, namely, the patients' responsiveness to an FTI treatment, as well as the expression levels of the gene or ratio of expression levels between genes of the group of patients. A number of statistical methods are well known in the art to determine the reference level (or referred to as the "cut-off value") of one or more genes when used to predict the responsiveness of a patient to a particular treatment, or to stratify patients for a particular treatment.

One method of the invention includes analyzing expression profiles for genes identified herein that distinguish responder from non-responder to determine the reference expression level for one or more genes. Comparisons between responders and non-responders can be performed using the Mann Whitney U-test, Chi-square test, or Fisher's Exact test. Analysis of descriptive statistics and comparisons can be performed using SigmaStat Software (Systat Software, Inc., San Jose, Calif., USA).

In some embodiments, a classification and regression tree (CART) analysis can be adopted to determine the reference level. CART analysis is based on a binary recursive partitioning algorithm and allows for the discovery of complex predictor variable interactions that may not be apparent with more traditional methods, such as multiple linear regression. Binary recursive partitioning refers to the analysis that is: 1) binary, meaning there were two possible outcome variables, namely "responders" and "non-responders," with the effect of splitting patients into 2 groups; 2) recursive, meaning the analysis can be performed multiple times; and 3) partitioned, meaning the entire data set can be split into sections. This analysis also has the ability to eliminate predictor variables with poor performance. The classification tree can be built using Salford Predictive Modeler v6.6 (Salford Systems, San Diego, Calif., USA).

Receiver Operator Characteristic (ROC) analysis can be utilized to determine the reference expression level, or reference expression ratio, or test the overall predictive value of individual genes and/or multiple genes. A review of the ROC analysis can be found in Soreide, J Clin Pathol 10.1136 (2008), which is hereby incorporated by reference in its entirety.

The reference level can be determined from the ROC curve of the training set to ensure both high sensitivity and high specificity. The performances of the predictors with different numbers of genes can be assessed based on misclassification error rate, sensitivity, specificity, p values measuring the separation of Kaplan-Meier curves of the two predicted groups.

The Top Scoring Pair (TSP) algorithm first introduced by Geman et al. (2004) can be used. In essence, the algorithm ranks all the gene pairs (genes i and j) based on the absolute difference (Dij) in the frequency of event where gene i has higher expression value than gene j in samples among class C1 to C2. In the cases of there are multiple top scoring pairs (all sharing the same Dij), the top pair by a secondary rank score that measures the magnitude to which inversions of gene expression levels occur from one class to the other within a pair of genes is selected. The top pair with highest frequency of absolute Dij>2 fold in all samples will be selected as candidate pair. The candidate pair can then be assessed in an independent testing data set. Leave-one-out cross validation (LOOCV) can be carried out in the training data set to evaluate how the algorithm perform. The performances of the predictors can be assessed based on maximum misclassification error rate. All the statistical analyses can be done using R (R Development Core Team, 2006).

Clinically reportable range (CRR) is the range of analyte values that a method can measure, allowing for specimen dilution, concentration, or other pretreatment used to extend the direct analytical measurement range. As provided in the Basic Methods Validation by Dr. Westgard, the experiment to be performed is often called a "linearity experiment," though there technically is no requirement that a method provide a linear response unless two-point calibration is being used. This range can also be referred as the "linear range," "analytical range," or "working range" for a method.

The reportable range is assessed by inspection of the linearity graph. That inspection can involve manually drawing the best straight line through the linear portion of the points, drawing a point-to-point line through all the points then comparing with the best straight line, or fitting a regression line through the points in the linear range. There are more complicated statistical calculations that are recommended in some guidelines, such as Clinical Laboratory Standards Institute (CLSI)'s EP-6 protocol for evaluating the linearity of analytical methods. But it is commonly accepted that the reportable range can be adequately determined from a "visual" assessment, i.e., by manually drawing the best straight line that fits the lowest points in the series. The Clinical Laboratory Standards Institute (CLSI) recommends a minimum of at least 4—preferably 5—different levels of concentrations. More than 5 can be used, particularly if the upper limit of reportable range needs to be maximized, but 5 levels are convenient and almost always sufficient.

A reference interval is typically established by assaying specimens that are obtained from individuals that meet carefully defined criteria (reference sample group). Protocols such as those of the International Federation of Clinical Chemistry (IFCC) Expert Panel on Theory of Reference Values and the CLSI delineate comprehensive systematic processes that use carefully selected reference sample groups to establish reference intervals. These protocols typically need a minimum of 120 reference individuals for each group (or subgroup) that needs to be characterized.

The CLSI Approved Guideline C28-A2 describes different ways for a laboratory to validate the transference of established reference intervals to the individual laboratory that includes 1. Divine judgment, wherein the laboratory simply reviews the information submitted and subjectively verifies that the reference intervals are applicable to the adopting laboratory's patient population and test methods; 2. Verification with 20 samples, wherein experimental validation is performed by collecting and analyzing specimens from 20 individuals who represent the reference sample population; 3. Estimation with 60 samples, wherein an experimental validation is performed by collecting and analyzing specimens from 60 individuals who represent the reference sample population, and the actual reference interval is estimated and compared to the claimed or reported interval using a statistical formula comparing the means and standard deviations of the two populations; and 4. Calculation from comparative method, wherein one can adjust or correct the claimed or reported reference intervals on the basis of the observed methodological bias and the mathematical relationship demonstrated between the analytical methods being used.

A person of ordinary skill in the art would understand that the reference expression level of the genes disclosed herein as well as the reference ratios between two or more genes can be determined by one or more methods as provided herein or other methods known in the art.

In some embodiments, the methods provided herein also include obtaining a sample from the subject. The sample used in the methods provided herein includes body fluids from a subject or a tumour biopsy from the subject.

In some embodiments, the sample used in the present methods includes a biopsy (e.g., a tumor biopsy). The biopsy can be from any organ or tissue, for example, skin, liver, lung, heart, colon, kidney, bone marrow, teeth, lymph node, hair, spleen, brain, breast, or other organs. Any biopsy technique known by those skilled in the art can be used for isolating a sample from a subject, for instance, open biopsy, close biopsy, core biopsy, incisional biopsy, excisional biopsy, or fine needle aspiration biopsy. In some embodiments, the sample used in the present methods includes an aspirate (e.g., bone marrow aspirate). In some embodiments, the sample is a lymph node biopsy. In some embodiments, the sample can be a frozen tissue sample. In some embodiments, the sample can be a formalin-fixed paraffin-embedded ("FFPE") tissue sample. In some embodiments, the sample can be a deparaffinised tissue section. In some embodiments, the sample can be a liver sample. In some embodiments, the sample can be a testicle sample. In some embodiments, the sample can be a spleen sample. In some embodiments, the sample can be a lymph node sample.

In some embodiments, the sample is a body fluid sample. Non-limiting examples of body fluids include blood (e.g., peripheral whole blood, peripheral blood), blood plasma, bone marrow, amniotic fluid, aqueous humor, bile, lymph, menses, serum, urine, cerebrospinal fluid surrounding the brain and the spinal cord, synovial fluid surrounding bone joints. In some embodiments, the sample can be a spinal fluid sample.

In some embodiments, the sample is a blood sample. The blood sample can be a whole blood sample, a partially purified blood sample, or a peripheral blood sample. The blood sample can be obtained using conventional techniques as described in, e.g. Innis et al, editors, PCR Protocols (Academic Press, 1990). White blood cells can be separated from blood samples using convention techniques or commercially available kits, e.g. RosetteSep kit (Stein Cell Technologies, Vancouver, Canada). Sub-populations of white blood cells, e.g. mononuclear cells, NK cells, B cells, T cells, monocytes, granulocytes or lymphocytes, can be further isolated using conventional techniques, e.g. magnetically activated cell sorting (MACS) (Miltenyi Biotec, Auburn, Calif.) or fluorescently activated cell sorting (FACS) (Becton Dickinson, San Jose, Calif.). In some embodiments, the sample is serum. In some embodiments, the sample is plasma. In one embodiment, the sample is a bone marrow sample.

In certain embodiments, the sample used in the methods provided herein includes a plurality of cells. Such cells can include any type of cells, e.g., stem cells, blood cells (e.g., PBMCs), lymphocytes, NK cells, B cells, T cells, monocytes, granulocytes, immune cells, or tumor or cancer cells. Specific cell populations can be obtained using a combination of commercially available antibodies (e.g., Quest Diagnostic (San Juan Capistrano, Calif.); Dako (Denmark)). In some embodiments, the sample is isolated cells.

In certain embodiments, the sample used in the methods provided herein includes a plurality of cells from the diseased tissue, e.g., a tumor sample from the subject having SCC. In some embodiments, the cells can be obtained from the tumor tissue, such as a tumor biopsy or a tumor explants. In certain embodiments, the number of cells used in the methods provided herein can range from a single cell to about $10^9$ cells. In some embodiments, the number of cells used in the methods provided herein is about $1 \times 10^4$, $5 \times 10^4$, $1 \times 10^5$, $5 \times 10^5$, $1 \times 10^6$, $5 \times 10^6$, $1 \times 10^7$, $5 \times 10^7$, $1 \times 10^8$, or $5 \times 10^8$. Different types of procedures are available to obtain a tumor biopsy from a patient, including skin biopsy, shave (tangential) biopsy, punch biopsy, incisional biopsy (which removes a portion of the tumor) and excisional biopsy (which removes the entire tumor). Lymph node biopsies are usually performed to examiner whether cancer has spread. Both fine needle aspiration (FNA) biopsy and surgical (excisional) lymph node biopsy are available options. The FNA biopsy allows the patient to use a thin needle to obtain a small fragment of the lymph node, which is less invasive than the surgical option, but may not always provide a large enough sample to find cancer cells.

The number and type of cells collected from a subject can be monitored, for example, by measuring changes in morphology and cell surface markers using standard cell detection techniques such as flow cytometry, cell sorting, immunocytochemistry (e.g., staining with tissue specific or cell-marker specific antibodies) fluorescence activated cell sorting (FACS), magnetic activated cell sorting (MACS), by examination of the morphology of cells using light or confocal microscopy, and/or by measuring changes in gene expression using techniques well known in the art, such as PCR and gene expression profiling. These techniques can be used, too, to identify cells that are positive for one or more particular markers. Fluorescence activated cell sorting (FACS) is a well-known method for separating particles, including cells, based on the fluorescent properties of the particles (Kamarch, 1987, Methods Enzymol, 151:150-165). Laser excitation of fluorescent moieties in the individual particles results in a small electrical charge allowing electromagnetic separation of positive and negative particles from a mixture. In one embodiment, cell surface marker-specific antibodies or ligands are labeled with distinct fluorescent labels. Cells are processed through the cell sorter, allowing separation of cells based on their ability to bind to the antibodies used. FACS sorted particles may be directly deposited into individual wells of 96-well or 384-well plates to facilitate separation and cloning.

In certain embodiments, subsets of cells are used in the methods provided herein. Methods to sort and isolate specific populations of cells are well-known in the art and can be based on cell size, morphology, or intracellular or extracellular markers. Such methods include, but are not limited to, flow cytometry, flow sorting, FACS, bead based separation such as magnetic cell sorting, size-based separation (e.g., a sieve, an array of obstacles, or a filter), sorting in a microfluidics device, antibody-based separation, sedimentation, affinity adsorption, affinity extraction, density gradient centrifugation, laser capture microdissection, etc.

The expression level of a gene can refer to the protein level or the mRNA level of the gene. In some embodiments, the expression level of a gene refers to the mRNA level of the gene, and methods provided herein include determining the mRNA level of the gene. In some embodiments, the expression level of a gene refers to the protein level of the gene, and methods provided herein include determining the protein level of the gene.

In some embodiments, the expression level of a gene can refer to the mRNA level of the gene. As such, the H-Ras expression level can refer to the mRNA level of H-Ras in a sample. N-Ras expression, or K-Ras expression can refer to their respective mRNA level. PIK3CA expression can refer to the mRNA level of PIK3CA in a sample. The H/K ratio can refer to the ratio of the mRNA level of H-Ras to the mRNA level of K-Ras. The H/N ratio can refer to the ratio of the mRNA level of H-Ras to the mRNA level of N-Ras. The H/K+N ratio can refer to the ratio of the mRNA level of H-Ras to the combined mRNA level of K-Ras and N-Ras.

Accordingly, in some embodiments, provided herein are methods for treating SCC in a subject, including administering a therapeutically effective amount of an FTI to the subject, wherein the subject has H-Ras mRNA level higher than a reference level. In some embodiments, the methods include analyzing a sample from the subject to measure the mRNA level of H-Ras in the sample, and determining that the subject has H-Ras overexpressing SCC, if the H-Ras mRNA level in the sample is higher than a reference level.

The FTI can be any FTI, including those described herein. For example, the FTI can be tipifarnib, lonafarnib, arglabin, perrilyl alcohol, L778123, L739749, FTI-277, L744832, CP-609,754, R208176, AZD3409, or BMS-214662. In some embodiments, the FTI is tipifarnib, and provided herein are methods to treat SCC in a subject, including administering a therapeutically effective amount of tipifarnib to the subject, wherein the subject has H-Ras mRNA level higher than a reference level. In some embodiments, the methods include analyzing a sample from the subject to measure the mRNA level of H-Ras in the sample, and determining that the subject has H-Ras overexpressing SCC if the H-Ras mRNA level in the sample is higher than a reference level.

In some embodiments, the subject has a H-Ras mRNA level that is at least 2 fold, at least 2.5 fold, at least 3 fold, at least 3.5 fold, at least 4 fold, at least 4.5 fold, at least 5 fold, at least 6 fold, at least 7 fold, at least 8 fold, at least 9 fold, at least 10 fold, at least 12 fold, at least 15 fold, or at least 20 fold greater than a reference level. In some embodiments, the subject has a H-Ras mRNA level that is at least 2 fold greater than a reference level. In some embodiments, the subject has a H-Ras mRNA level that is at least 2.5 fold greater than a reference level. In some embodiments, the subject has a H-Ras mRNA level that is at least 3 fold greater than a reference level. In some embodiments, the subject has a H-Ras mRNA level that is at least 3.5 fold greater than a reference level. In some embodiments, the subject has a H-Ras mRNA level that is at least 4 fold greater than a reference level. In some embodiments, the subject has a H-Ras mRNA level that is at least 4.5 fold greater than a reference level. In some embodiments, the subject has a H-Ras mRNA level that is at least 5 fold greater than a reference level. In some embodiments, the subject has a H-Ras mRNA level that is at least 6 fold greater than a reference level. In some embodiments, the subject has a H-Ras mRNA level that is at least 7 fold greater than a reference level. In some embodiments, the subject has a H-Ras mRNA level that is at least 8 fold greater than a reference level. In some embodiments, the subject has a H-Ras mRNA level that is at least 9 fold greater than a reference level. In some embodiments, the subject has a H-Ras mRNA level that is at least 10 fold greater than a reference level. In some embodiments, the subject has a H-Ras mRNA level that is at least 12 fold greater than a reference level. In some embodiments, the subject has a H-Ras mRNA level that is at least 15 fold greater than a reference level. In some embodiments, the subject has a H-Ras mRNA level that is at least 20 fold greater than a reference level. In some embodiments, the reference level is the median mRNA level of H-Ras in a population of healthy subjects. In some embodiments, the reference level is the median mRNA level of H-Ras in a population of subjects having SCC.

In some embodiments of the methods provided herein, wherein the expression level of a gene is determined by its mRNA level, the SCC is human papillomavirus (HPV)-negative SCC. In some embodiments, the SCC is at an advanced stage. In some embodiments, the SCC is metastatic SCC. In some embodiments, the SCC is relapsed SCC. In some embodiments, the SCC is refractory. The SCC can be a specific type of SCC. In some embodiments, the SCC is head and neck SCC (HNSCC). In some embodiments, the SCC is lung SCC (LSCC). In some embodiments, the SCC is thyroid SCC. In some embodiments, the SCC is esophagus SCC. In some embodiments, the SCC is bladder SCC. In some embodiments, the SCC is urothelial carcinoma (UC).

In some embodiments, methods provided herein include determining the mRNA level of a gene. Methods to determine the mRNA level of a gene in a sample are well known in the art. For example, in some embodiments, the mRNA level can be determined by Polymerase Chain Reaction (PCR), qPCR, qRT-PCR, RNA-seq, microarray analysis, SAGE, MassARRAY technique, next-generation sequencing, or FISH.

Exemplary methods of detecting or quantitating mRNA levels include but are not limited to PCR-based methods, northern blots, ribonuclease protection assays, and the like. The mRNA sequence can be used to prepare a probe that is at least partially complementary. The probe can then be used to detect the mRNA sequence in a sample, using any suitable assay, such as PCR-based methods, Northern blotting, a dipstick assay, and the like.

The commonly used methods known in the art for the quantification of mRNA expression in a sample include northern blotting and in situ hybridization (Parker &Barnes, Methods in Molecular Biology 106:247-283 (1999)); RNAse protection assays (Hod, Biotechniques 13:852-854 (1992)); and polymerase chain reaction (PCR) (Weis et ah, Trends in Genetics 8:263-264 (1992)). Alternatively, antibodies may be employed that can recognize specific duplexes, including DNA duplexes, RNA duplexes, and DNA-RNA hybrid duplexes or DNA-protein duplexes. Representative methods for sequencing-based gene expression analysis include Serial Analysis of Gene Expression (SAGE), and gene expression analysis by massively parallel signature sequencing (MPSS).

A sensitive and flexible quantitative method is PCR. Examples of PCR methods can be found in the literature. Examples of PCR assays can be found in U.S. Pat. No. 6,927,024, which is incorporated by reference herein in its entirety. Examples of RT-PCR methods can be found in U.S. Pat. No. 7,122,799, which is incorporated by reference herein in its entirety. A method of fluorescent in situ PCR is described in U.S. Pat. No. 7,186,507, which is incorporated by reference herein in its entirety.

It is noted, however, that other nucleic acid amplification protocols (i.e., other than PCR) may also be used in the nucleic acid analytical methods described herein. For example, suitable amplification methods include ligase chain reaction (see, e.g., Wu & Wallace, Genomics 4:560-569, 1988); strand displacement assay (see, e.g., Walker et al., Proc. Natl. Acad. Sci. USA 89:392-396, 1992; U.S. Pat. No. 5,455,166); and several transcription-based amplification systems, including the methods described in U.S. Pat. Nos. 5,437,990; 5,409,818; and 5,399,491; the transcription amplification system (TAS) (Kwoh et al., Proc. Natl. Acad. Sci. USA 86: 1173-1177, 1989); and self-sustained sequence replication (3SR) (Guatelli et al., Proc. Natl. Acad. Sci. USA 87: 1874-1878, 1990; WO 92/08800). Alternatively, methods that amplify the probe to detectable levels can be used, such as Q-replicase amplification (Kramer & Lizardi, Nature 339:401-402, 1989; Lomeli et al., Clin. Chem. 35: 1826-1831, 1989). A review of known amplification methods is provided, for example, by Abramson and Myers in Current Opinion in Biotechnology 4:41-47 (1993).

mRNA can be isolated from the sample. The sample can be a tissue sample. The tissue sample can be a tumour biopsy, such as a lymph node biopsy. General methods for mRNA extraction are well known in the art and are disclosed in standard textbooks of molecular biology, including Ausubel et al., Current Protocols of Molecular Biology, John Wiley and Sons (1997). In particular, RNA isolation can be performed using purification kit, buffer set and protease from commercial manufacturers, such as Qiagen, according to the manufacturer's instructions. For example, total RNA from cells in culture can be isolated using Qiagen RNeasy mini-columns. Other commercially available RNA isolation kits include MASTERPURE® Complete DNA and RNA Purification Kit (EPICENTRE®, Madison, Wis.), and Paraffin Block RNA Isolation Kit (Ambion, Inc.). Total RNA from tissue samples can be isolated using RNA Stat-60 (Tel-Test). RNA prepared from tumor can be isolated, for example, by cesium chloride density gradient centrifugation.

In some embodiments, the first step in gene expression profiling by PCR is the reverse transcription of the RNA template into cDNA, followed by its exponential amplification in a PCR reaction. In other embodiments, a combined reverse-transcription-polymerase chain reaction (RT-PCR) reaction may be used, e.g., as described in U.S. Pat. Nos. 5,310,652; 5,322,770; 5,561,058; 5,641,864; and 5,693,517. The two commonly used reverse transcriptases are avilo myeloblastosis virus reverse transcriptase (AMV-RT) and Moloney murine leukemia virus reverse transcriptase (MMLV-RT). The reverse transcription step is typically primed using specific primers, random hexamers, or oligo-dT primers, depending on the circumstances and the goal of expression profiling. For example, extracted RNA can be reverse-transcribed using a GENEAMP™ RNA PCR kit (Perkin Elmer, Calif, USA), following the manufacturer's instructions. The derived cDNA can then be used as a template in the subsequent PCR reaction.

In some embodiments, Real-Time Reverse Transcription-PCR (qRT-PCR) can be used for both the detection and quantification of RNA targets (Bustin, et al., 2005, *Clin. Sci.*, 109:365-379). Examples of qRT-PCR-based methods can be found, for example, in U.S. Pat. No. 7,101,663, which is incorporated by reference herein in its entirety. Instruments for real-time PCR, such as the Applied Biosystems 7500, are available commercially, as are the reagents, such as TaqMan Sequence Detection chemistry.

For example, TaqMan® Gene Expression Assays can be used, following the manufacturer's instructions. These kits are pre-formulated gene expression assays for rapid, reliable detection and quantification of human, mouse and rat mRNA transcripts. TaqMan® or 5'-nuclease assay, as described in U.S. Pat. Nos. 5,210,015; 5,487,972; and 5,804,375; and Holland et al., 1988, Proc. Natl. Acad. Sci. USA 88:7276-7280, can be used. TAQMAN® PCR typically utilizes the 5'-nuclease activity of Taq or Tth polymerase to hydrolyze a hybridization probe bound to its target amplicon, but any enzyme with equivalent 5' nuclease activity can be used. Two oligonucleotide primers are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

Any method suitable for detecting degradation product can be used in a 5' nuclease assay. Often, the detection probe is labeled with two fluorescent dyes, one of which is capable of quenching the fluorescence of the other dye. The dyes are attached to the probe, preferably one attached to the 5' terminus and the other is attached to an internal site, such that quenching occurs when the probe is in an unhybridized state and such that cleavage of the probe by the 5' to 3' exonuclease activity of the DNA polymerase occurs in between the two dyes.

Amplification results in cleavage of the probe between the dyes with a concomitant elimination of quenching and an increase in the fluorescence observable from the initially quenched dye. The accumulation of degradation product is monitored by measuring the increase in reaction fluorescence. U.S. Pat. Nos. 5,491,063 and 5,571,673, both incorporated herein by reference, describe alternative methods for detecting the degradation of probe which occurs concomitant with amplification. 5'-Nuclease assay data may be initially expressed as Ct, or the threshold cycle. As discussed above, fluorescence values are recorded during every cycle and represent the amount of product amplified to that point in the amplification reaction. The point when the fluorescent signal is first recorded as statistically significant is the threshold cycle (Ct).

To minimize errors and the effect of sample-to-sample variation, PCR is usually performed using an internal standard. The ideal internal standard is expressed at a constant level among different tissues, and is unaffected by the experimental treatment. RNAs most frequently used to normalize patterns of gene expression are mRNAs for the housekeeping genes glyceraldehyde-3-phosphate-dehydrogenase (GAPDH) and P-actin.

PCR primers and probes are designed based upon intron sequences present in the gene to be amplified. In this embodiment, the first step in the primer/probe design is the delineation of intron sequences within the genes. This can be done by publicly available software, such as the DNA BLAST software developed by Kent, W., Genome Res. 12(4):656-64 (2002), or by the BLAST software including its variations. Subsequent steps follow well established methods of PCR primer and probe design.

In order to avoid non-specific signals, it can be important to mask repetitive sequences within the introns when designing the primers and probes. This can be easily accomplished by using the Repeat Masker program available on-line through the Baylor College of Medicine, which screens DNA sequences against a library of repetitive elements and returns a query sequence in which the repetitive elements are masked. The masked intron sequences can then be used to design primer and probe sequences using any commercially or otherwise publicly available primer/probe design packages, such as Primer Express (Applied Biosystems); MGB assay-by-design (Applied Biosystems); Primer3 (Rozen and Skaletsky (2000) Primer3 on the WWW for general users and for biologist programmers. In: Krawetz S, Misener S (eds) Bioinformatics Methods and Protocols: Methods in Molecular Biology. Humana Press, Totowa, N.J., pp 365-386).

RNA-Seq, also called Whole Transcriptome Shotgun Sequencing (WTSS) refers to the use of high-throughput sequencing technologies to sequence cDNA in order to get information about a sample's RNA content. Publications describing RNA-Seq include: Wang et al., Nature Reviews Genetics 10 (1): 57-63 (January 2009); Ryan et al. BioTechniques 45 (1): 81-94 (2008); and Maher et al., Nature 458 (7234): 97-101 (January 2009); which are hereby incorporated in their entirety.

Differential gene expression can also be identified, or confirmed using the microarray technique. In this method, polynucleotide sequences of interest (including cDNAs and oligonucleotides) are plated, or arrayed, on a microchip substrate. The arrayed sequences are then hybridized with specific DNA probes from cells or tissues of interest.

In an embodiment of the microarray technique, PCR amplified inserts of cDNA clones are applied to a substrate in a dense array. Preferably at least 10,000 nucleotide sequences are applied to the substrate. The microarrayed genes, immobilized on the microchip at 10,000 elements each, are suitable for hybridization under stringent conditions. Fluorescently labeled cDNA probes may be generated through incorporation of fluorescent nucleotides by reverse transcription of RNA extracted from tissues of interest. Labeled cDNA probes applied to the chip hybridize with specificity to each spot of DNA on the array. After stringent washing to remove non-specifically bound probes, the chip is scanned by confocal laser microscopy or by another detection method, such as a CCD camera. Quantitation of hybridization of each arrayed element allows for assessment of corresponding mRNA abundance. With dual color fluorescence, separately labeled cDNA probes generated from two sources of RNA are hybridized pairwise to the array. The relative abundance of the transcripts from the two sources corresponding to each specified gene is thus determined simultaneously. The miniaturized scale of the hybridization affords a convenient and rapid evaluation of the expression pattern for large numbers of genes. Such methods have been shown to have the sensitivity required to detect rare transcripts, which are expressed at a few copies per cell, and to reproducibly detect at least approximately two-fold differences in the expression levels (Schena et al., Proc. Natl. Acad. Sci. USA 93(2): 106-149 (1996)). Microarray analysis can be performed by commercially available equipment, following manufacturer's protocols, such as by using the Affymetrix GENCHIP™ technology, or Incyte's microarray technology.

Serial analysis of gene expression (SAGE) is a method that allows the simultaneous and quantitative analysis of a large number of gene transcripts, without the need of providing an individual hybridization probe for each transcript. First, a short sequence tag (about 10-14 bp) is generated that contains sufficient information to uniquely identify a transcript, provided that the tag is obtained from a unique position within each transcript. Then, many transcripts are linked together to form long serial molecules, that can be sequenced, revealing the identity of the multiple tags simultaneously. The expression pattern of any population of transcripts can be quantitatively evaluated by determining the abundance of individual tags, and identifying the gene corresponding to each tag. For more details see, e.g. Velculescu et al., Science 270:484-487 (1995); and Velculescu et al., Cell 88:243-51 (1997).

The MassARRAY (Sequenom, San Diego, Calif.) technology is an automated, high-throughput method of gene expression analysis using mass spectrometry (MS) for detection. According to this method, following the isolation of RNA, reverse transcription and PCR amplification, the cDNAs are subjected to primer extension. The cDNA-derived primer extension products are purified, and dispensed on a chip array that is pre-loaded with the components needed for MALTI-TOF MS sample preparation. The various cDNAs present in the reaction are quantitated by analyzing the peak areas in the mass spectrum obtained.

mRNA level can also be measured by an assay based on hybridization. A typical mRNA assay method can contain the steps of 1) obtaining surface-bound subject probes; 2) hybridization of a population of mRNAs to the surface-bound probes under conditions sufficient to provide for specific binding (3) post-hybridization washes to remove nucleic acids not bound in the hybridization; and (4) detection of the hybridized mRNAs. The reagents used in each of these steps and their conditions for use may vary depending on the particular application.

Any suitable assay platform can be used to determine the mRNA level in a sample. For example, an assay can be in the form of a dipstick, a membrane, a chip, a disk, a test strip, a filter, a microsphere, a slide, a multiwell plate, or an optical fiber. An assay system can have a solid support on which a nucleic acid corresponding to the mRNA is attached. The solid support can have, for example, a plastic, silicon, a metal, a resin, glass, a membrane, a particle, a precipitate, a gel, a polymer, a sheet, a sphere, a polysaccharide, a capillary, a film a plate, or a slide. The assay components can be prepared and packaged together as a kit for detecting an mRNA.

The nucleic acid can be labeled, if desired, to make a population of labeled mRNAs. In general, a sample can be labeled using methods that are well known in the art (e.g., using DNA ligase, terminal transferase, or by labeling the RNA backbone, etc.; see, e.g., Ausubel, et al., *Short Protocols in Molecular Biology*, 3rd ed., Wiley & Sons 1995 and Sambrook et al., *Molecular Cloning: A Laboratory Manual*, Third Edition, 2001 Cold Spring Harbor, N.Y.). In some embodiments, the sample is labeled with fluorescent label. Exemplary fluorescent dyes include but are not limited to xanthene dyes, fluorescein dyes, rhodamine dyes, fluorescein isothiocyanate (FITC), 6 carboxyfluorescein (FAM), 6 carboxy-2',4',7',4,7-hexachlorofluorescein (HEX), 6 carboxy 4',5' dichloro 2',7' dimethoxyfluorescein (JOE or J), N,N,N',N' tetramethyl 6 carboxyrhodamine (TAMRA or T), 6 carboxy X rhodamine (ROX or R), 5 carboxyrhodamine 6G (R6G5 or G5), 6 carboxyrhodamine 6G (R6G6 or G6), and rhodamine 110; cyanine dyes, e.g. Cy3, Cy5 and Cy7 dyes; Alexa dyes, e.g. Alexa-fluor-555; coumarin, Diethylaminocoumarin, umbelliferone; benzimide dyes, e.g. Hoechst 33258; phenanthridine dyes, e.g. Texas Red; ethidium dyes; acridine dyes; carbazole dyes; phenoxazine dyes; porphyrin dyes; polymethine dyes, BODIPY dyes, quinoline dyes, Pyrene, Fluorescein Chlorotriazinyl, 8110, Eosin, JOE, R6G, Tetramethylrhodamine, Lissamine, ROX, Napthofluorescein, and the like.

Hybridization can be carried out under suitable hybridization conditions, which may vary in stringency as desired. Typical conditions are sufficient to produce probe/target complexes on a solid surface between complementary binding members, i.e., between surface-bound subject probes and complementary mRNAs in a sample. In certain embodiments, stringent hybridization conditions can be employed.

Hybridization is typically performed under stringent hybridization conditions. Standard hybridization techniques (e.g. under conditions sufficient to provide for specific binding of target mRNAs in the sample to the probes) are described in Kallioniemi et al., *Science* 258:818-821 (1992) and WO 93/18186. Several guides to general techniques are available, e.g., Tijssen, *Hybridization with Nucleic Acid Probes*, Parts I and II (Elsevier, Amsterdam 1993). For descriptions of techniques suitable for in situ hybridizations, see Gall et al. *Meth. Enzymol.*, 21:470-480 (1981); and Angerer et al. in *Genetic Engineering: Principles and Methods* (Setlow and Hollaender, Eds.) Vol 7, pgs 43-65 (Plenum Press, New York 1985). Selection of appropriate conditions, including temperature, salt concentration, polynucleotide concentration, hybridization time, stringency of washing conditions, and the like will depend on experimental design, including source of sample, identity of capture agents, degree of complementarity expected, etc., and may be determined as a matter of routine experimentation for those of ordinary skill in the art. Those of ordinary skill will readily recognize that alternative but comparable hybridization and wash conditions can be utilized to provide conditions of similar stringency.

After the mRNA hybridization procedure, the surface bound polynucleotides are typically washed to remove unbound nucleic acids. Washing may be performed using any convenient washing protocol, where the washing conditions are typically stringent, as described above. The hybridization of the target mRNAs to the probes is then detected using standard techniques.

Any methods as described herein or otherwise known in the art can be used to determine the mRNA level of a gene in a sample from a subject described herein. By way of example, in some embodiments, provided herein are methods to treat AML in a subject that include determining the mRNA level of FLT3LG in a sample from the subject by using qRT-PCR, and administering a therapeutically effective amount of an FTI to the subject if the mRNA level of FLT3LG in the sample is higher than a reference expression level of the FLT3LG.

In some embodiment, the expression level of a gene can refer to the protein level of the gene. As such, the H-Ras expression level can refer to the protein level of H-Ras in a sample. N-Ras expression, or K-Ras expression can refer to their respective protein level. PIK3CA expression can refer to the mRNA level of PIK3CA in a sample. The H/K ratio can refer to the ratio of the H-Ras protein level to the K-Ras protein level. The H/N ratio can refer to the ratio of the H-Ras protein level to N-Ras protein level. The H/K+N ratio can refer to the ratio of the H-Ras protein level to the combined protein level of K-Ras and N-Ras.

Accordingly, in some embodiments, provided herein are methods for treating SCC in a subject, including administering a therapeutically effective amount of an FTI to the subject, wherein the subject has H-Ras protein level higher than a reference level. In some embodiments, the methods include analyzing a sample from the subject to measure the protein level of H-Ras in the sample, and determining that the subject has H-Ras overexpressing SCC, if the H-Ras protein level in the sample is higher than a reference level.

The FTI can be any FTI, including those described herein. For example, the FTI can be tipifarnib, lonafarnib, arglabin, perrilyl alcohol, L778123, L739749, FTI-277, L744832, CP-609,754, R208176, AZD3409, or BMS-214662. In some embodiments, the FTI is tipifarnib, and provided herein are methods to treat SCC in a subject, including administering a therapeutically effective amount of tipifarnib to the subject, wherein the subject has H-Ras protein level higher than a reference level. In some embodiments, the methods include analyzing a sample from the subject to measure the protein level of H-Ras in the sample, and determining that the subject has H-Ras overexpressing SCC if the H-Ras protein level in the sample is higher than a reference level.

In some embodiments, the subject has a H-Ras protein level that is at least 2 fold, at least 2.5 fold, at least 3 fold, at least 3.5 fold, at least 4 fold, at least 4.5 fold, at least 5 fold, at least 6 fold, at least 7 fold, at least 8 fold, at least 9 fold, at least 10 fold, at least 12 fold, at least 15 fold, or at least 20 fold greater than a reference level. In some embodiments, the subject has a H-Ras protein level that is at least 2 fold greater than a reference level. In some embodiments, the subject has a H-Ras protein level that is at least 2.5 fold greater than a reference level. In some embodiments, the subject has a H-Ras protein level that is at least 3 fold greater than a reference level. In some embodiments, the subject has a H-Ras protein level that is at least 3.5 fold greater than a reference level. In some embodiments, the subject has a H-Ras protein level that is at least 4 fold greater than a reference level. In some embodiments, the subject has a H-Ras protein level that is at least 4.5 fold greater than a reference level. In some embodiments, the subject has a H-Ras protein level that is at least 5 fold greater than a reference level. In some embodiments, the subject has a H-Ras protein level that is at least 6 fold greater than a reference level. In some embodiments, the subject has a H-Ras protein level that is at least 7 fold greater than a reference level. In some embodiments, the subject has a H-Ras protein level that is at least 8 fold greater than a reference level. In some embodiments, the subject has a H-Ras protein level that is at least 9 fold greater than a reference level. In some embodiments, the subject has a H-Ras protein level that is at least 10 fold greater than a reference level. In some embodiments, the subject has a H-Ras protein level that is at least 12 fold greater than a reference level. In some embodiments, the subject has a H-Ras protein level that is at least 15 fold greater than a reference level. In some embodiments, the subject has a H-Ras protein level that is at least 20 fold greater than a reference level. In some embodiments, the reference level is the median protein level of H-Ras in a population of healthy subjects. In some embodiments, the reference level is the median protein level of H-Ras in a population of subjects having SCC.

In some embodiments of the methods provided herein, wherein the expression level of a gene is determined by its protein level, the SCC is human papillomavirus (HPV)-negative SCC. In some embodiments, the SCC is at an advanced stage. In some embodiments, the SCC is metastatic SCC. In some embodiments, the SCC is relapsed SCC. In some embodiments, the SCC is refractory. The SCC can be a specific type of SCC. In some embodiments, the SCC is head and neck SCC (HNSCC). In some embodiments, the SCC is lung SCC (LSCC). In some embodiments, the SCC is thyroid SCC. In some embodiments, the SCC is esophagus SCC. In some embodiments, the SCC is bladder SCC. In some embodiments, the SCC is urothelial carcinoma (UC).

Methods to determine a protein level of a gene in a sample are well known in the art. For example, in some embodiments, the protein level can be determined by an immunohistochemistry (IHC) assay, an immunoblotting (IB) assay, an immunofluorescence (IF) assay, flow cytometry (FACS), or an Enzyme-Linked Immunosorbent Assay (ELISA). In some embodiments, the protein level can be determined by Hematoxylin and Eosin stain ("H&E staining").

The protein level of the gene can be detected by a variety of (IHC) approaches or other immunoassay methods. IHC staining of tissue sections has been shown to be a reliable method of assessing or detecting presence of proteins in a sample. Immunohistochemistry techniques utilize an antibody to probe and visualize cellular antigens in situ, generally by chromogenic or fluorescent methods. Thus, antibodies or antisera, including for example, polyclonal antisera, or monoclonal antibodies specific for each gene are used to detect expression. As discussed in greater detail below, the antibodies can be detected by direct labelling of the antibodies themselves, for example, with radioactive labels, fluorescent labels, hapten labels such as, biotin, or an enzyme such as horse radish peroxidase or alkaline phosphatase. Alternatively, unlabeled primary antibody is used in conjunction with a labeled secondary antibody, comprising antisera, polyclonal antisera or a monoclonal antibody specific for the primary antibody. Immunohistochemistry protocols and kits are well known in the art and are commercially available. Automated systems for slide preparation and IHC processing are available commercially. The Ventana® BenchMark XT system is an example of such an automated system.

Standard immunological and immunoassay procedures can be found in *Basic and Clinical Immunology* (Stites & Ten eds., 7th ed. 1991). Moreover, the immunoassays can be performed in any of several configurations, which are reviewed extensively in *Enzyme Immunoassay* (Maggio, ed., 1980); and Harlow & Lane, supra. For a review of the general immunoassays, see also *Methods in Cell Biology: Antibodies in Cell Biology*, volume 37 (Asai, ed. 1993); *Basic and Clinical Immunology* (Stites & Ten, eds., 7th ed. 1991).

Commonly used assays to detect protein level of a gene include noncompetitive assays, e.g., sandwich assays, and competitive assays. Typically, an assay such as an ELISA assay can be used. ELISA assays are known in the art, e.g., for assaying a wide variety of tissues and samples, including blood, plasma, serum, a tumor biopsy, a lymph node, or bone marrow. In some embodiments, the sample is a bone marrow biopsy. In some embodiments, the sample is a bone marrow aspirate. In some embodiments, the sample can be a spinal fluid sample, a liver sample, a testicle sample, a spleen sample, or a lymph node sample. In some embodiments, the sample is isolated cells.

A wide range of immunoassay techniques using such an assay format are available, see, e.g., U.S. Pat. Nos. 4,016, 043, 4,424,279, and 4,018,653, which are hereby incorporated by reference in their entireties. These include both single-site and two-site or "sandwich" assays of the non-competitive types, as well as in the traditional competitive binding assays. These assays also include direct binding of a labeled antibody to a target gene. Sandwich assays are commonly used assays. A number of variations of the sandwich assay technique exist. For example, in a typical forward assay, an unlabelled antibody is immobilized on a solid substrate, and the sample to be tested brought into contact with the bound molecule. After a suitable period of incubation, for a period of time sufficient to allow formation of an antibody-antigen complex, a second antibody specific to the antigen, labeled with a reporter molecule capable of producing a detectable signal is then added and incubated, allowing time sufficient for the formation of another complex of antibody-antigen-labeled antibody. Any unreacted material is washed away, and the presence of the antigen is determined by observation of a signal produced by the reporter molecule. The results may either be qualitative, by simple observation of the visible signal, or may be quantitated by comparing with a control sample containing known amounts of the gene.

Variations on the forward assay include a simultaneous assay, in which both sample and labeled antibody are added simultaneously to the bound antibody. These techniques are well known to those skilled in the art, including any minor variations as will be readily apparent. In a typical forward sandwich assay, a first antibody having specificity for the gene is either covalently or passively bound to a solid surface. The solid surface may be glass or a polymer, the most commonly used polymers being cellulose, polyacrylamide, nylon, polystyrene, polyvinyl chloride, or polypropylene. The solid supports may be in the form of tubes, beads, discs of microplates, or any other surface suitable for conducting an immunoassay. The binding processes are well-known in the art and generally consist of cross-linking covalently binding or physically adsorbing, the polymer-antibody complex is washed in preparation for the test sample. An aliquot of the sample to be tested is then added to the solid phase complex and incubated for a period of time sufficient (e.g. 2-40 minutes or overnight if more convenient) and under suitable conditions (e.g., from room temperature to 40° C. such as between 25° C. and 32° C. inclusive) to allow binding of any subunit present in the antibody. Following the incubation period, the antibody subunit solid phase is washed and dried and incubated with a second antibody specific for a portion of the gene. The second antibody is linked to a reporter molecule which is used to indicate the binding of the second antibody to the molecular marker.

An alternative method involves immobilizing the target gene in the sample and then exposing the immobilized target to specific antibody which may or may not be labelled with a reporter molecule. Depending on the amount of target and the strength of the reporter molecule signal, a bound target may be detectable by direct labelling with the antibody. Alternatively, a second labelled antibody, specific to the first antibody is exposed to the target-first antibody complex to form a target-first antibody-second antibody tertiary complex. The complex is detected by the signal emitted by a labelled reporter molecule.

In the case of an enzyme immunoassay, an enzyme is conjugated to the second antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, beta-galactosidase, and alkaline phosphatase, and other are discussed herein. The substrates to be used with the specific enzymes are generally chosen for the production, upon hydrolysis by the corresponding enzyme, of a detectable color change. Examples of suitable enzymes include alkaline phosphatase and peroxidase. It is also possible to employ fluorogenic substrates, which yield a fluorescent product rather than the chromogenic substrates noted above. In all cases, the enzyme-labeled antibody is added to the first antibody-molecular marker complex, allowed to bind, and then the excess reagent is washed away. A solution containing the appropriate substrate is then added to the complex of antibody-antigen-antibody. The substrate will react with the enzyme linked to the second antibody, giving a qualitative visual signal, which may be further quantitated, usually spectrophotometrically, to give an indication of the amount of gene which was present in the sample. Alternately, fluorescent compounds, such as fluorescein and rhodamine, can be chemically coupled to antibodies without altering their binding capacity. When activated by illumination with light of a particular wavelength, the fluorochrome-labeled antibody adsorbs the light energy, inducing a state to excitability in the molecule, followed by emission of the light at a characteristic color visually detectable with a light microscope. As in the EIA, the fluorescent labeled antibody is allowed to bind to the first antibody-molecular marker complex. After washing off the unbound reagent, the remaining tertiary complex is then exposed to the light of the appropriate wavelength, the fluorescence observed indicates the presence of the molecular marker of interest. Immunofluorescence and EIA techniques are both very well established in the art and are discussed herein.

Any methods as described herein or otherwise known in the art can be used to determine the protein level of a gene in a sample from a subject described herein. By way of example, in some embodiments, provided herein are methods to treat HNSCC in a subject that include determining the protein level of H-Ras in a sample from the subject by using an IF assay, and administering a therapeutically effective amount of tipifarnib to the subject if the protein level of H-Ras in the sample is higher than a reference level of the H-Ras protein.

Any methods for analyzing expression levels (e.g., the protein level or the mRNA level) as described herein or otherwise known in the art can be used to determine the level of the additional gene in a sample, such as an IHC assay, an IB assay, an IF assay, FACS, ELISA, protein microarray analysis, qPCR, qRT-PCR, RNA-seq, RNA microarray analysis, SAGE, MassARRAY technique, next-generation sequencing, or FISH.

In some embodiments, provided herein are methods for treating SCC in a subject, including administering a therapeutically effective amount of an FTI to the subject, wherein the subject carries an H-Ras gene mutation. In some embodiments, the H-Ras gene mutation results in activation of the corresponding H-Ras protein. In some embodiments, the H-Ras gene mutation results in alteration in the amino acid sequence of an H-Ras protein that results in its activation. In some embodiments, the methods include analyzing a sample from the subject to determine the H-Ras mutation status of the subject.

The FTI can be any FTI, including those described herein. For example, the FTI can be tipifarnib, lonafarnib, arglabin, perrilyl alcohol, L778123, L739749, FTI-277, L744832, CP-609,754, R208176, AZD3409, or BMS-214662. In some embodiments, the FTI is tipifarnib, and provided herein are methods to treat SCC in a subject, including administering a therapeutically effective amount of tipifarnib to the subject, wherein the subject carries an H-Ras gene mutation. In some embodiments, the H-Ras gene mutation results in activation of the corresponding H-Ras protein. In some embodiments, the H-Ras gene mutation results in alteration in the amino acid sequence of an H-Ras protein that results in its activation. In some embodiments, the methods include analyzing a sample from the subject to determine the H-Ras mutation status of the subject.

In some embodiments of the methods provided herein, wherein the subject carries an H-Ras gene mutation, the SCC is human papillomavirus (HPV)-negative SCC. In some embodiments, the SCC is at an advanced stage. In some embodiments, the SCC is metastatic SCC. In some embodiments, the SCC is relapsed SCC. In some embodiments, the SCC is refractory. The SCC can be a specific type of SCC. In some embodiments, the SCC is head and neck SCC (HNSCC). In some embodiments, the SCC is lung SCC (LSCC). In some embodiments, the SCC is thyroid SCC. In some embodiments, the SCC is esophagus SCC. In some embodiments, the SCC is bladder SCC. In some embodiments, the SCC is urothelial carcinoma (UC).

The methods provided herein can also be used in connection with other patient stratification approaches to further increase the response rate of a patient population to an FTI treatment. For example, in some embodiments, the methods provided herein further include determining the mutation status of H-Ras and selecting a subject for an FTI treatment, if the subject carries a H-Ras mutation. The term "H-Ras mutation" as used herein refers to an activation mutation in an HRAS gene or H-Ras protein. An H-Ras mutation can refer to either a genetic alternation in the DNA sequence of the HRAS gene that results in activation of the corresponding H-Ras protein, or the alteration in the amino acid sequence of an H-Ras protein that results in its activation. Thus, the term "H-Ras mutation" as used herein does not include an alternation in a HRAS gene that does not result in the activation of the H-Ras protein, or an alternation of an H-Ras protein sequence that does not lead to its activation. Accordingly, a sample or a subject that does not have any "H-Ras mutation" as used herein can still have a mutation in the HRAS gene that does not affect the activity of the H-Ras protein or a mutation that impairs the activity of the H-Ras protein, or have a mutation in an H-Ras protein that does not affect its activity or a mutation that impairs its activity. A sample or a subject can have multiple copies of the HRAS gene. A sample or a subject can also have both wild type and mutant H-Ras proteins. As used herein, a sample or a subject having an H-Ras mutation can also have a copy of wild type HRAS gene and/or the wild type H-Ras protein. A sample or a subject that is determined to "have wild type H-Ras," as used herein, refers to the sample or subject that only has the wild type HRAS gene and the wild type H-Ras protein, and no H-Ras mutation. In some embodiments, the mutant HRAS gene encodes a mutant H-Ras protein, wherein the HRAS gene mutation is or comprises a modification in a codon that encodes an amino acid substitution at a specific position selected from a group consisting of G12, G13, Q61, Q22, K117, A146, and any combination thereof, in the corresponding mutant H-Ras protein. In some embodiments, the HRAS gene mutation is a mutation at a codon that encodes an amino acid substitution at a position of G12 in the mutant H-Ras protein. In some embodiments, the HRAS gene mutation is at a codon that encodes a G12R substitution in the mutant H-Ras protein. The HRAS gene mutation can be a mutation at a codon that encodes a G12C, G12D, G12A, G12V, G12S, G12F, G12R, or G12N, substitution in the mutant H-Ras protein. In some embodiments, the HRAS gene mutation is a mutation at a codon that encodes a G12V substitution in the mutant H-Ras protein. In some embodiments, the HRAS gene mutation is a mutation at a codon that encodes an amino acid substitution at a position of G13 in the mutant H-Ras protein. The HRAS gene mutation can be a mutation at a codon that encodes a G13A, G13C, G13V, G13D, G13R, G13S, or G13N, substitution in the mutant H-Ras protein. In some embodiments, the HRAS gene mutation is a mutation at a codon that encodes a G13C substitution in the mutant H-Ras protein. In some embodiments, the HRAS gene mutation is a mutation at a codon that encodes a G13R substitution in the mutant H-Ras protein. In some embodiments, the HRAS gene mutation is a mutation at a codon that encodes an amino acid substitution at a position of Q61 in the mutant H-Ras protein. The HRAS gene mutation can be a mutation at a codon that encodes a Q61E, Q61K, Q61H, Q61L, Q61P, or Q61R, substitution in the mutant H-Ras protein. In some embodiments, the HRAS gene mutation is a mutation at a codon that encodes a Q61L substitution in the mutant H-Ras protein. In some embodiments, the HRAS gene mutation is a mutation at a codon that encodes a Q61R substitution in the mutant H-Ras protein. In some embodiments, the HRAS gene mutation is a mutation at a codon that encodes an amino acid substitution at a position of Q22 in the mutant H-Ras protein. In some embodiments, the HRAS gene mutation is a mutation at a codon that encodes a Q22K substitution in the mutant H-Ras protein. In some embodiments, the HRAS gene mutation is a mutation at a codon that encodes an amino acid substitution at a position of K117 in the mutant H-Ras protein. In some embodiments, the HRAS gene mutation is a mutation at a codon that encodes a K117N or K117L substitution in the mutant H-Ras protein. In some embodiments, the HRAS gene mutation is a mutation at a codon that encodes an amino acid substitution at a position of A146 in the mutant H-Ras protein. The HRAS gene mutation can be a mutation at a codon that encodes a A146V or A146P, substitution in the mutant H-Ras protein. In some embodiments, the HRAS gene mutation is a mutation at a codon that encodes an A146P substitution in the mutant H-Ras protein. In some embodiments, the mutation can be a mutation at another codon that results in activation of H-Ras protein.

Methods for determining mutation status are well known in the art. In some embodiments, the methods include sequencing, Polymerase Chain Reaction (PCR), DNA microarray, Mass Spectrometry (MS), Single Nucleotide Polymorphism (SNP) assay, denaturing high-performance liquid chromatography (DHPLC), or Restriction Fragment Length Polymorphism (RFLP) assay. In some embodiments, the mutation status of an HRAS gene is determined using standard sequencing methods, including, for example, Sanger sequencing, next generation sequencing (NGS). In some embodiments, the mutation status of an HRAS gene can be determined an NGS-based assay. In some embodiments, the mutation status of an HRAS gene can be determined by a qualitative PCR-based assay. In some embodiments, the SNV and/or mutation status is determined using MS. In some embodiments, the HRAS mutation status is determined by analyzing protein obtained from the sample. The mutated Ras H-protein can be detected by a variety of immunohistochemistry (IHC) approaches, Immunoblotting assay, Enzyme-Linked Immunosorbent Assay (ELISA) or other immunoassay methods known in the art.

As a person of ordinary skill in the art would understand, any methods described herein or otherwise known in the art for analyzing Ras mutation can be used to determining the presence or absence of a H-Ras mutation.

B. Pharmaceutical Compositions

In some embodiments, provided herein is a method of treating a subject with an FTI or a pharmaceutical composition having an FTI. The pharmaceutical compositions provided herein contain therapeutically effective amounts of an FTI and a pharmaceutically acceptable carrier, diluent or excipient. In some embodiments, the FTI is tipifarnib; lonafarnib (also known as SCH-66336); arglabin; perrilyl alcohol; CP-609,754, BMS 214662; L778123; L744832; L739749; R208176; AZD3409; or FTI-277. In some embodiments, the FTI is tipifarnib.

The FTI can be formulated into suitable pharmaceutical preparations such as solutions, suspensions, tablets, dispersible tablets, pills, capsules, powders, sustained release formulations or elixirs, for oral administration or in sterile solutions or suspensions for ophthalmic or parenteral administration, as well as transdermal patch preparation and dry powder inhalers. Typically the FTI is formulated into pharmaceutical compositions using techniques and procedures well known in the art (see, e.g., Ansel Introduction to Pharmaceutical Dosage Forms, Seventh Edition 1999).

In the compositions, effective concentrations of the FTI and pharmaceutically acceptable salts is (are) mixed with a suitable pharmaceutical carrier or vehicle. In certain embodiments, the concentrations of the FTI in the compositions are effective for delivery of an amount, upon administration, that treats, prevents, or ameliorates one or more of the symptoms and/or progression of cancer, including haematological cancers and solid tumors.

The compositions can be formulated for single dosage administration. To formulate a composition, the weight fraction of the FTI is dissolved, suspended, dispersed or otherwise mixed in a selected vehicle at an effective concentration such that the treated condition is relieved or ameliorated. Pharmaceutical carriers or vehicles suitable for administration of the FTI provided herein include any such carriers known to those skilled in the art to be suitable for the particular mode of administration.

In addition, the FTI can be formulated as the sole pharmaceutically active ingredient in the composition or may be combined with other active ingredients. Liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as known in the art. Briefly, liposomes such as multilamellar vesicles (MLV's) may be formed by drying down egg phosphatidyl choline and brain phosphatidyl serine (7:3 molar ratio) on the inside of a flask. A solution of an FTI provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

The FTI is included in the pharmaceutically acceptable carrier in an amount sufficient to exert a therapeutically useful effect in the absence of undesirable side effects on the patient treated. The therapeutically effective concentration may be determined empirically by testing the compounds in in vitro and in vivo systems described herein and then extrapolated therefrom for dosages for humans.

The concentration of FTI in the pharmaceutical composition will depend on absorption, tissue distribution, inactivation and excretion rates of the FTI, the physicochemical characteristics of the FTI, the dosage schedule, and amount administered as well as other factors known to those of skill in the art. For example, the amount that is delivered is sufficient to ameliorate one or more of the symptoms of cancer, including hematopoietic cancers and solid tumors.

In certain embodiments, a therapeutically effective dosage should produce a serum concentration of active ingredient of from about 0.1 ng/ml to about 50-100 µg/ml. In one embodiment, the pharmaceutical compositions provide a dosage of from about 0.001 mg to about 2000 mg of compound per kilogram of body weight per day. Pharmaceutical dosage unit forms are prepared to provide from about 1 mg to about 1000 mg and in certain embodiments, from about 10 to about 500 mg of the essential active ingredient or a combination of essential ingredients per dosage unit form.

The FTI may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

Thus, effective concentrations or amounts of one or more of the compounds described herein or pharmaceutically acceptable salts thereof are mixed with a suitable pharmaceutical carrier or vehicle for systemic, topical or local administration to form pharmaceutical compositions. Compounds are included in an amount effective for ameliorating one or more symptoms of, or for treating, retarding progression, or preventing. The concentration of active compound in the composition will depend on absorption, tissue distribution, inactivation, excretion rates of the active compound, the dosage schedule, amount administered, particular formulation as well as other factors known to those of skill in the art.

The compositions are intended to be administered by a suitable route, including but not limited to orally, parenterally, rectally, topically and locally. For oral administration, capsules and tablets can be formulated. The compositions are in liquid, semi-liquid or solid form and are formulated in a manner suitable for each route of administration.

Solutions or suspensions used for parenteral, intradermal, subcutaneous, or topical application can include any of the following components: a sterile diluent, such as water for injection, saline solution, fixed oil, polyethylene glycol, glycerine, propylene glycol, dimethyl acetamide or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose. Parenteral preparations can be enclosed in ampules, pens, disposable syringes or single or multiple dose vials made of glass, plastic or other suitable material.

In instances in which the FTI exhibits insufficient solubility, methods for solubilizing compounds can be used. Such methods are known to those of skill in this art, and include, but are not limited to, using cosolvents, such as dimethylsulfoxide (DMSO), using surfactants, such as TWEEN®, or dissolution in aqueous sodium bicarbonate.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil water emulsions containing suitable quantities of the compounds or pharmaceutically acceptable salts thereof. The pharmaceutically therapeutically active compounds and salts thereof are formulated and administered in unit dosage forms or multiple dosage forms. Unit dose forms as used herein refer to physically discrete units suitable for human and animal subjects and packaged individually as is known in the art. Each unit dose contains a predetermined quantity of the therapeutically active compound sufficient to produce the desired therapeutic effect, in association with the required pharmaceutical carrier, vehicle or diluent. Examples of unit dose forms include ampules and syringes and individually packaged tablets or capsules. Unit dose forms may be administered in fractions or multiples thereof. A multiple dose form is a plurality of identical unit dosage forms packaged in a single container to be administered in segregated unit dose form. Examples of multiple dose forms include vials, bottles of tablets or capsules or bottles of pints or gallons. Hence, multiple dose form is a multiple of unit doses which are not segregated in packaging.

Sustained-release preparations can also be prepared. Suitable examples of sustained-release preparations include semipermeable matrices of solid hydrophobic polymers containing the compound provided herein, which matrices are in the form of shaped articles, e.g., films, or microcapsule. Examples of sustained-release matrices include iontophoresis patches, polyesters, hydrogels (for example, poly(2-hydroxyethyl-methacrylate), or poly(vinylalcohol)), polylactides, copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated compound remain in the body for a long time, they may denature or aggregate as a result of exposure to moisture at 37° C., resulting in a loss of biological activity and possible changes in their structure. Rational strategies can be devised for stabilization depending on the mechanism of action involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Dosage forms or compositions containing active ingredient in the range of 0.005% to 100% with the balance made up from nontoxic carrier may be prepared. For oral administration, a pharmaceutically acceptable nontoxic composition is formed by the incorporation of any of the normally employed excipients, such as, for example pharmaceutical grades of mannitol, lactose, starch, magnesium stearate, talcum, cellulose derivatives, sodium crosscarmellose, glucose, sucrose, magnesium carbonate or sodium saccharin. Such compositions include solutions, suspensions, tablets, capsules, powders and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparation of these compositions are known to those skilled in the art. The contemplated compositions may contain about 0.001% 100% active ingredient, in certain embodiments, about 0.1-85% or about 75-95%.

The FTI or pharmaceutically acceptable salts can be prepared with carriers that protect the compound against rapid elimination from the body, such as time release formulations or coatings.

The compositions can include other active compounds to obtain desired combinations of properties. The compounds provided herein, or pharmaceutically acceptable salts thereof as described herein, can also be administered together with another pharmacological agent known in the general art to be of value in treating one or more of the diseases or medical conditions referred to hereinabove, such as diseases related to oxidative stress.

Lactose-free compositions provided herein can contain excipients that are well known in the art and are listed, for example, in the U.S. Pharmocopia (USP) SP (XXI)/NF (XVI). In general, lactose-free compositions contain an active ingredient, a binder/filler, and a lubricant in pharmaceutically compatible and pharmaceutically acceptable amounts. Exemplary lactose-free dosage forms contain an active ingredient, microcrystalline cellulose, pre-gelatinized starch and magnesium stearate.

Further encompassed are anhydrous pharmaceutical compositions and dosage forms containing a compound provided herein. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, Drug Stability: Principles & Practice, 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment and use of formulations.

Anhydrous pharmaceutical compositions and dosage forms provided herein can be prepared using anhydrous or low moisture containing ingredients and low moisture or low humidity conditions. Pharmaceutical compositions and dosage forms that comprise lactose and at least one active ingredient that comprises a primary or secondary amine are anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs and strip packs.

Oral pharmaceutical dosage forms are either solid, gel or liquid. The solid dosage forms are tablets, capsules, granules, and bulk powders. Types of oral tablets include compressed, chewable lozenges and tablets which may be enteric coated, sugar coated or film coated. Capsules may be hard or soft gelatin capsules, while granules and powders may be provided in noneffervescent or effervescent form with the combination of other ingredients known to those skilled in the art.

In certain embodiments, the formulations are solid dosage forms, such as capsules or tablets. The tablets, pills, capsules, troches and the like can contain any of the following ingredients, or compounds of a similar nature: a binder; a diluent; a disintegrating agent; a lubricant; a glidant; a sweetening agent; and a flavoring agent.

Examples of binders include microcrystalline cellulose, gum tragacanth, glucose solution, acacia mucilage, gelatin solution, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

Pharmaceutically acceptable carriers included in tablets are binders, lubricants, diluents, disintegrating agents, coloring agents, flavoring agents, and wetting agents. Enteric coated tablets, because of the enteric coating, resist the action of stomach acid and dissolve or disintegrate in the neutral or alkaline intestines. Sugar coated tablets are compressed tablets to which different layers of pharmaceutically acceptable substances are applied. Film coated tablets are compressed tablets which have been coated with a polymer or other suitable coating. Multiple compressed tablets are compressed tablets made by more than one compression cycle utilizing the pharmaceutically acceptable substances previously mentioned. Coloring agents may also be used in the above dosage forms. Flavoring and sweetening agents are used in compressed tablets, sugar coated, multiple compressed and chewable tablets. Flavoring and sweetening agents are especially useful in the formation of chewable tablets and lozenges.

Liquid oral dosage forms include aqueous solutions, emulsions, suspensions, solutions and/or suspensions reconstituted from non effervescent granules and effervescent preparations reconstituted from effervescent granules. Aqueous solutions include, for example, elixirs and syrups. Emulsions are either oil in-water or water in oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two phase system in which one liquid is dispersed in the form of small globules throughout another liquid. Pharmaceutically acceptable carriers used in emulsions are non aqueous liquids, emulsifying agents and preservatives. Suspensions use pharmaceutically acceptable suspending agents and preservatives. Pharmaceutically acceptable substances used in non effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic add, sodium benzoate and alcohol. Examples of non aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Diluents include lactose and sucrose. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic adds include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example propylene carbonate, vegetable oils or triglycerides, is encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include, but are not limited to, those containing a compound provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl) acetals of lower alkyl aldehydes such as acetaldehyde diethyl acetal.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

Parenteral administration, generally characterized by injection, either subcutaneously, intramuscularly or intravenously is also provided herein. Injectables can be prepared in conventional forms, either as liquid solutions or suspensions, solid forms suitable for solution or suspension in liquid prior to injection, or as emulsions. Suitable excipients are, for example, water, saline, dextrose, glycerol or ethanol. In addition, if desired, the pharmaceutical compositions to be administered may also contain minor amounts of non toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins. Implantation of a slow release or sustained release system, such that a constant level of dosage is maintained is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple dose containers which include phenols or cresols, mercurials, benzyl alcohol, chlorobutanol, methyl and propyl p hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylceluose, hydroxypropyl methylcellulose and polyvinylpyrrolidone. Emulsifying agents include Polysorbate 80 (TWEEN® 80). A sequestering or chelating agent of metal ions include EDTA. Pharmaceutical carriers also include ethyl alcohol, polyethylene glycol and propylene glycol for water miscible vehicles and sodium hydroxide, hydrochloric acid, citric acid or lactic acid for pH adjustment.

The concentration of the FTI is adjusted so that an injection provides an effective amount to produce the desired pharmacological effect. The exact dose depends on the age, weight and condition of the patient or animal as is known in the art. The unit dose parenteral preparations are packaged in an ampule, a vial or a syringe with a needle. All preparations for parenteral administration must be sterile, as is known and practiced in the art.

Illustratively, intravenous or intraarterial infusion of a sterile aqueous solution containing an FTI is an effective mode of administration. Another embodiment is a sterile aqueous or oily solution or suspension containing an active material injected as necessary to produce the desired pharmacological effect.

Injectables are designed for local and systemic administration. Typically a therapeutically effective dosage is formulated to contain a concentration of at least about 0.1% w/w up to about 90% w/w or more, such as more than 1% w/w of the active compound to the treated tissue(s). The active ingredient may be administered at once, or may be divided into a number of smaller doses to be administered at intervals of time. It is understood that the precise dosage and duration of treatment is a function of the tissue being treated and may be determined empirically using known testing protocols or by extrapolation from in vivo or in vitro test data. It is to be noted that concentrations and dosage values may also vary with the age of the individual treated. It is to be further understood that for any particular subject, specific dosage regimens should be adjusted over time according to the individual need and the professional judgment of the person administering or supervising the administration of the formulations, and that the concentration ranges set forth herein are exemplary only and are not intended to limit the scope or practice of the claimed formulations.

The FTI can be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

Of interest herein are also lyophilized powders, which can be reconstituted for administration as solutions, emulsions and other mixtures. They can also be reconstituted and formulated as solids or gels.

The sterile, lyophilized powder is prepared by dissolving an FTI provided herein, or a pharmaceutically acceptable salt thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. Generally, the resulting solution will be apportioned into vials for lyophilization. Each vial will contain a single dosage (including but not limited to 10-1000 mg or 100-500 mg) or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, about 1-50 mg, about 5-35 mg, or about 9-30 mg of lyophilized powder, is added per mL of sterile water or other suitable carrier. The precise amount depends upon the selected compound. Such amount can be empirically determined.

Topical mixtures are prepared as described for the local and systemic administration. The resulting mixture may be a solution, suspension, emulsion or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The FTI or pharmaceutical composition having an FTI can be formulated as aerosols for topical application, such as by inhalation (see, e.g., U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will have diameters of less than 50 microns or less than 10 microns.

The FTI or pharmaceutical composition having an FTI can be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered. These solutions, particularly those intended for ophthalmic use, may be formulated as 0.01%-10% isotonic solutions, pH about 5-7, with appropriate salts.

Other routes of administration, such as transdermal patches, and rectal administration are also contemplated herein. For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin gelatin, carbowax (polyoxyethylene glycol)

and appropriate mixtures of mono, di and triglycerides of fatty acids. Combinations of the various bases may be used. Agents to raise the melting point of suppositories include spermaceti and wax. Rectal suppositories may be prepared either by the compressed method or by molding. An exemplary weight of a rectal suppository is about 2 to 3 grams. Tablets and capsules for rectal administration are manufactured using the same pharmaceutically acceptable substance and by the same methods as for formulations for oral administration.

The FTI or pharmaceutical composition having an FTI provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, 5,639,480, 5,733,566, 5,739,108, 5,891,474, 5,922,356, 5,972,891, 5,980,945, 5,993,855, 6,045,830, 6,087,324, 6,113,943, 6,197,350, 6,248,363, 6,264,970, 6,267,981, 6,376,461,6,419,961, 6,589,548, 6,613,358, 6,699,500 and 6,740,634, each of which is incorporated herein by reference. Such dosage forms can be used to provide slow or controlled-release of FTI using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients provided herein.

All controlled-release pharmaceutical products have a common goal of improving drug therapy over that achieved by their non-controlled counterparts. In one embodiment, the use of an optimally designed controlled-release preparation in medical treatment is characterized by a minimum of drug substance being employed to cure or control the condition in a minimum amount of time. In certain embodiments, advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

In certain embodiments, the FTI can be administered using intravenous infusion, an implantable osmotic pump, a transdermal patch, liposomes, or other modes of administration. In one embodiment, a pump may be used (see, Sefton, CRC Crit. Ref. Biomed. Eng. 14:201 (1987); Buchwald et al., Surgery 88:507 (1980); Saudek et al., N. Engl. J. Med. 321:574 (1989). In another embodiment, polymeric materials can be used. In yet another embodiment, a controlled release system can be placed in proximity of the therapeutic target, i.e., thus requiring only a fraction of the systemic dose (see, e.g., Goodson, Medical Applications of Controlled Release, vol. 2, pp. 115-138 (1984).

In some embodiments, a controlled release device is introduced into a subject in proximity of the site of inappropriate immune activation or a tumor. Other controlled release systems are discussed in the review by Langer (Science 249:1527-1533 (1990). The F can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The active ingredient then diffuses through the outer polymeric membrane in a release rate controlling step. The percentage of active ingredient contained in such parenteral compositions is highly dependent on the specific nature thereof, as well as the needs of the subject.

The FTI or pharmaceutical composition of FTI can be packaged as articles of manufacture containing packaging material, a compound or pharmaceutically acceptable salt thereof provided herein, which is used for treatment, prevention or amelioration of one or more symptoms or progression of cancer, including haematological cancers and solid tumors, and a label that indicates that the compound or pharmaceutically acceptable salt thereof is used for treatment, prevention or amelioration of one or more symptoms or progression of cancer, including haematological cancers and solid tumors.

The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, pens, bottles, and any packaging material suitable for a selected formulation and intended mode of administration and treatment. A wide array of formulations of the compounds and compositions provided herein are contemplated.

In some embodiments, a therapeutically effective amount of the pharmaceutical composition having an FTI is administered orally or parenterally.

In some embodiments, the FTI is administered at a daily dose of from 0.05 up to 1800 mg/kg. In some embodiments, the FTI is administered at a daily dose of from 0.05 up to 1500 mg/kg. In some embodiments, the FTI is administered at a daily dose of from 0.05 up to 500 mg/kg. In some embodiments, the FTI is administered in an amount of 0.05 mg/kg daily, 0.1 mg/kg daily, 0.2 mg/kg daily, 0.5 mg/kg daily, 1 mg/kg daily, 2 mg/kg daily, 5 mg/kg daily, 10 mg/kg daily, 20 mg/kg daily, 50 mg/kg daily, 100 mg/kg daily, 200 mg/kg daily, 300 mg/kg daily, 400 mg/kg daily, 500 mg/kg daily, 600 mg/kg daily, 700 mg/kg daily, 800 mg/kg daily, 900 mg/kg daily, 1000 mg/kg daily, 1100 mg/kg daily, 1200 mg/kg daily, 1300 mg/kg daily, 1400 mg/kg daily, or 1500 mg/kg daily. In some embodiments, the FTI is administered at 1 mg/kg daily. In some embodiments, the FTI is administered at 2 mg/kg daily. In some embodiments, the FTI is administered at 5 mg/kg daily. In some embodiments, the FTI is administered at 10 mg/kg daily. In some embodiments, the FTI is administered at 20 mg/kg daily. In some embodiments, the FTI is administered at 50 mg/kg daily. In some embodiments, the FTI is administered at 100 mg/kg daily. In some embodiments, the FTI is administered at 200 mg/kg daily. In some embodiments, the FTI is administered at 500 mg/kg daily. The FTI can be administered either as a single dose or subdivided into more than one dose. In some embodiments, the FTI is tipifarnib.

In some embodiments, the FTI is administered at a dose of 50-2400 mg daily. In some embodiments, the FTI is administered at a dose of 100-1800 mg daily. In some embodiments, the FTI is administered at a dose of 100-1200 mg daily. In some embodiments, the FTI is administered at a dose of 50 mg, 100 mg, 200 mg, 300 mg, 400 mg, 500 mg, 600 mg, 700 mg, 800 mg, 900 mg, 1000 mg, 1100 mg, 1200 mg, 1300 mg, 1400 mg, 1500 mg, 1600 mg, 1700 mg, 1800 mg, 1900 mg, 2000 mg, 2100 mg, 2200 mg, 1200 mg, or 2400 mg daily. In some embodiments, the FTI is administered at a dose of 200 mg daily. The FTI can be administered at a dose of 300 mg daily. The FTI can be administered at a dose of 400 mg daily. The FTI can be administered at a dose of 500 mg daily. The FTI can be administered at a dose of 600 mg daily. The FTI can be administered at a dose of 700 mg daily. The FTI can be administered at a dose of 800 mg daily. The FTI can be administered at a dose of 900 mg daily. The FTI can be administered at a dose of 1000 mg daily. The FTI can be administered at a dose of 1100 mg daily. The FTI can be administered at a dose of 1200 mg daily. The FTI can be administered at a dose of 1300 mg daily. The FTI can be administered at a dose of 1400 mg daily. The FTI can be administered at a dose of 1500 mg daily. The FTI can be administered at a dose of 1600 mg daily. The FTI can be administered at a dose of 1700 mg daily. The FTI can be administered at a dose of 1800 mg daily. The FTI can be administered at a dose of 1900 mg daily. The FTI can be administered at a dose of 2000 mg daily. The FTI can be administered at a dose of 2100 mg daily. The FTI can be administered at a dose of 2200 mg daily. The FTI can be administered at a dose of 2300 mg daily. The FTI can be administered at a dose of 2400 mg daily. The FTI can be administered either as a single dose or subdivided into more than one dose. In some embodiments, the FTI is tipifarnib.

In some embodiments, an FTI is administered at a dose of 100, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1025, 1050, 1075, 1100, 1125, 1150, 1175, or 1200 mg twice a day (b.i.d). In some embodiments, the FTI is administered at a dose of 100-1400 mg b.i.d. In some embodiments, the FTI is administered at a dose of 100-1200 mg b.i.d. In some embodiments, the FTI is administered at a dose of 300-1200 mg b.i.d. In some embodiments, the FTI is administered at a dose of 300-900 mg b.i.d. In some embodiments, the FTI is administered at a dose of 300 mg b.i.d. In some embodiments, the FTI is administered at a dose of 400 mg b.i.d. In some embodiments, the FTI is administered at a dose of 500 mg b.i.d. In some embodiments, the FTI is administered at a dose of 600 mg b.i.d. In some embodiments, the FTI is administered at a dose of 700 mg b.i.d. In some embodiments, the FTI is administered at a dose of 800 mg b.i.d. In some embodiments, the FTI is administered at a dose of 900 mg b.i.d. In some embodiments, the FTI is administered at a dose of 1000 mg b.i.d. In some embodiments, the FTI is administered at a dose of 1100 mg b.i.d. In some embodiments, the FTI is administered at a dose of 1200 mg b.i.d. In some embodiments, the FTI for use in the compositions and methods provided herein is tipifarnib.

As a person of ordinary skill in the art would understand, the dosage varies depending on the dosage form employed, condition and sensitivity of the patient, the route of administration, and other factors. The exact dosage will be determined by the practitioner, in light of factors related to the subject that requires treatment. Dosage and administration are adjusted to provide sufficient levels of the active ingredient or to maintain the desired effect. Factors which can be taken into account include the severity of the disease state, general health of the subject, age, weight, and gender of the subject, diet, time and frequency of administration, drug combination(s), reaction sensitivities, and tolerance/response to therapy. During a treatment cycle, the daily dose could be varied. In some embodiments, a starting dosage can be titrated down within a treatment cycle. In some embodiments, a starting dosage can be titrated up within a treatment cycle. The final dosage can depend on the occurrence of dose limiting toxicity and other factors. In some embodiments, the FTI is administered at a starting dose of 300 mg daily and escalated to a maximum dose of 400 mg, 500 mg, 600 mg, 700 mg, 800 mg, 900 mg, 1000 mg, 1100 mg, or 1200 mg daily. In some embodiments, the FTI is administered at a starting dose of 400 mg daily and escalated to a maximum dose of 500 mg, 600 mg, 700 mg, 800 mg, 900 mg, 1000 mg, 1100 mg, or 1200 mg daily. In some embodiments, the FTI is administered at a starting dose of 500 mg daily and escalated to a maximum dose of 600 mg, 700 mg, 800 mg, 900 mg, 1000 mg, 1100 mg, or 1200 mg daily. In some embodiments, the FTI is administered at a starting dose of 600 mg daily and escalated to a maximum dose of 700 mg, 800 mg, 900 mg, 1000 mg, 1100 mg, or 1200 mg daily. In some embodiments, the FTI is administered at a starting dose of 700 mg daily and escalated to a maximum dose of 800 mg, 900 mg, 1000 mg, 1100 mg, or 1200 mg daily. In some embodiments, the FTI is administered at a starting dose of 800 mg daily and escalated to a maximum dose of 900 mg, 1000 mg, 1100 mg, or 1200 mg daily. In some embodiments, the FTI is administered at a starting dose of 900 mg daily and escalated to a maximum dose of 1000 mg, 1100 mg, or 1200 mg daily. The dose escalation can be done at once, or step wise. For example, a starting dose at 600 mg daily can be escalated to a final dose of 1000 mg daily by increasing by 100 mg per day over the course of 4 days, or by increasing by 200 mg per day over the course of 2 days, or by increasing by 400 mg at once. In some embodiments, the FTI is tipifarnib.

In some embodiments, the FTI is administered at a relatively high starting dose and titrated down to a lower dose depending on the patient response and other factors. In some embodiments, the FTI is administered at a starting dose of 1200 mg daily and reduced to a final dose of 1100 mg, 1000 mg, 900 mg, 800 mg, 700 mg, 600 mg, 500 mg, 400 mg, or 300 mg daily. In some embodiments, the FTI is administered at a starting dose of 1100 mg daily and reduced to a final dose of 1000 mg, 900 mg, 800 mg, 700 mg, 600 mg, 500 mg, 400 mg, or 300 mg daily. In some embodiments, the FTI is administered at a starting dose of 1000 mg daily and reduced to a final dose of 900 mg, 800 mg, 700 mg, 600 mg, 500 mg, 400 mg, or 300 mg daily. In some embodiments, the FTI is administered at a starting dose of 900 mg daily and reduced to a final dose of 800 mg, 700 mg, 600 mg, 500 mg, 400 mg, or 300 mg daily. In some embodiments, the FTI is administered at a starting dose of 800 mg daily and reduced to a final dose of 700 mg, 600 mg, 500 mg, 400 mg, or 300 mg daily. In some embodiments, the FTI is administered at a starting dose of 600 mg daily and reduced to a final dose of 500 mg, 400 mg, or 300 mg daily. The dose reduction can be done at once, or step wise. In some embodiments, the FTI is tipifarnib. For example, a starting dose at 900 mg daily can be reduced to a final dose of 600 mg daily by decreasing by 100 mg per day over the course of 3 days, or by decreasing by 300 mg at once. In some embodiments, the FTI is tipifarnib.

A treatment cycle can have different length. In some embodiments, a treatment cycle can be one week, 2 weeks, 3 weeks, 4 weeks, 5 weeks, 6 weeks, 7 weeks, 8 weeks, 3 months, 4 months, 5 months, 6 months, 7 months, 8 months, 9 months, 10 months, 11 months, or 12 months. In some embodiments, a treatment cycle is 4 weeks. A treatment cycle can have intermittent schedule. In some embodiments, a 2-week treatment cycle can have 5-day dosing followed by 9-day rest. In some embodiments, a 2-week treatment cycle can have 6-day dosing followed by 8-day rest. In some embodiments, a 2-week treatment cycle can have 7-day dosing followed by 7-day rest. In some embodiments, a 2-week treatment cycle can have 8-day dosing followed by 6-day rest. In some embodiments, a 2-week treatment cycle can have 9-day dosing followed by 5-day rest. In some embodiment, a 4 week treatment cycle can have 7 day dosing, followed by 21-day rest. In some embodiment, a 4 week treatment cycle can have 21 day dosing, followed by 7-day rest. In some embodiment, a 4 week treatment cycle can have dosing on days 1-7 and 15-21, and rest on days 8-14 and 22-28.

In some embodiments, the FTI can be administered for at least one treatment cycle. In some embodiments, the FTI can be administered for at least two, at least three, at least four, at least five, at least six, at least seven, at least eight, at least nine, at least ten, at least eleven, or at least twelve treatment cycles. In some embodiments, the FTI can be administered for at least two treatment cycles. In some embodiments, the FTI can be administered for at least three treatment cycles. In some embodiments, the FTI can be administered for at least six treatment cycles. In some embodiments, the FTI can be administered for at least nine treatment cycles. In some embodiments, the FTI can be administered for at least twelve treatment cycles. In some embodiments, the FTI is tipifarnib.

In some embodiments, the FTI is administered for up to two weeks. In some embodiments, the FTI is administered for up to three weeks, up to one month, up to two months, up to three months, up to four months, up to five months, up to six months, up to seven months, up to eight months, up to nine months, up to ten months, up to eleven months, or up to twelve months. In some embodiments, the FTI is administered for up to one month. In some embodiments, the FTI is administered for up to three months. In some embodiments, the FTI is administered for up to six months. In some embodiments, the FTI is administered for up to nine months. In some embodiments, the FTI is administered for up to twelve months.

In some embodiments, the FTI is administered daily for 3 of out of 4 weeks in repeated 4 week cycles. In some embodiments, the FTI is administered daily in alternate weeks (one week on, one week off) in repeated 4 week cycles. In some embodiments, the FTI is administered at a dose of 300 mg b.i.d. orally for 3 of out of 4 weeks in repeated 4 week cycles. In some embodiments, the FTI is administered at a dose of 600 mg b.i.d. orally for 3 of out of 4 weeks in repeated 4 week cycles. In some embodiments, the FTI is administered at a dose of 900 mg b.i.d. orally in alternate weeks (one week on, one week off) in repeated 4 week cycles. In some embodiments, the FTI is administered at a dose of 1200 mg b.i.d. orally in alternate weeks (days 1-7 and 15-21 of repeated 28-day cycles). In some embodiments, the FTI is administered at a dose of 1200 mg b.i.d. orally for days 1-5 and 15-19 out of repeated 28-day cycles.

In some embodiments, a 300 mg bid tipifarnib alternate week regimen can be used adopted. Under the regimen, patients receive a starting dose of 300 mg, po, bid on days 1-7 and 15-21 of 28-day treatment cycles. In the absence of unmanageable toxicities, subjects can continue to receive the tipifarnib treatment for up to 12 months. The dose can also be increased to 1200 mg bid if the subject is tolerating the treatment well. Stepwise 300 mg dose reductions to control treatment-related, treatment-emergent toxicities can also be included.

In some embodiments, a 600 mg bid tipifarnib alternate week regimen can be used adopted. Under the regimen, patients receive a starting dose of 600 mg, po, bid on days 1-7 and 15-21 of 28-day treatment cycles. In the absence of unmanageable toxicities, subjects can continue to receive the tipifarnib treatment for up to 12 months. The dose can also be increased to 1200 mg bid if the subject is tolerating the treatment well. Stepwise 300 mg dose reductions to control treatment-related, treatment-emergent toxicities can also be included.

In some embodiments, a 900 mg bid tipifarnib alternate week regimen can be used adopted. Under the regimen, patients receive a starting dose of 900 mg, po, bid on days 1-7 and 15-21 of 28-day treatment cycles. In the absence of unmanageable toxicities, subjects can continue to receive the tipifarnib treatment for up to 12 months. The dose can also be increased to 1200 mg bid if the subject is tolerating the treatment well. Stepwise 300 mg dose reductions to control treatment-related, treatment-emergent toxicities can also be included.

In some other embodiments, tipifarnib is given orally at a dose of 300 mg bid daily for 21 days, followed by 1 week of rest, in 28-day treatment cycles (21-day schedule; Cheng D T, et al., *J Mol Diagn.* (2015) 17(3):251-64). In some embodiments, a 5-day dosing ranging from 25 to 1300 mg bid followed by 9-day rest is adopted (5-day schedule; Zujewski J., *J Clin Oncol.,* (2000) February; 18(4):927-41). In some embodiments, a 7-day bid dosing followed by 7-day rest is adopted (7-day schedule; Lara P N Jr., *Anticancer Drugs.,* (2005) 16(3):317-21; Kirschbaum M H, *Leukemia.,* (2011) October; 25(10):1543-7). In the 7-day schedule, the patients can receive a starting dose of 300 mg bid with 300 mg dose escalations to a maximum planned dose of 1800 mg bid. In the 7-day schedule study, patients can also receive tipifarnib bid on days 1-7 and days 15-21 of 28-day cycles at doses up to 1600 mg bid.

In previous studies FTI were shown to inhibit the growth of mammalian tumors when administered as a twice daily dosing schedule. It was found that administration of an FTI in a single dose daily for one to five days produced a marked suppression of tumor growth lasting out to at least 21 days. In some embodiments, FTI is administered at a dosage range of 50-400 mg/kg. In some embodiments, FTI is administered at 200 mg/kg. Dosing regimen for specific FTIs are also well known in the art (e.g., U.S. Pat. No. 6,838,467, which is incorporated herein by reference in its entirety). For example, suitable dosages for the compounds Arglabin (WO98/28303), perrilyl alcohol (WO 99/45712), SCH-66336 (U.S. Pat. No. 5,874,442), L778123 (WO 00/01691), 2(S)-[2(S)-[2(R)-amino-3-mercapto]propylamino-3(S)-methyl]-pentyloxy-3-phenylpropionyl-methionine sulfone (WO94/10138), BMS 214662 (WO 97/30992), AZD3409; Pfizer compounds A and B (WO 00/12499 and WO 00/12498) are given in the aforementioned patent specifications which are incorporated herein by reference or are known to or can be readily determined by a person skilled in the art.

In relation to perrilyl alcohol, the medicament may be administered 1-4 g per day per 150 lb human patient. In one embodiment, 1-2 g per day per 150 lb human patient. SCH-66336 typically may be administered in a unit dose of about 0.1 mg to 100 mg, more preferably from about 1 mg to 300 mg according to the particular application. Compounds L778123 and 1-(3-chlorophenyl)-4-[1-(4-cyanobenzyl)-5-imidazolylmethyl]-2-piperazinone may be administered to a human patient in an amount between about 0.1 mg/kg of body weight to about 20 mg/kg of body weight per day, preferably between 0.5 mg/kg of bodyweight to about 10 mg/kg of body weight per day.

Pfizer compounds A and B may be administered in dosages ranging from about 1.0 mg up to about 500 mg per day, preferably from about 1 to about 100 mg per day in single or divided (i.e. multiple) doses. Therapeutic compounds will ordinarily be administered in daily dosages ranging from about 0.01 to about 10 mg per kg body weight per day, in single or divided doses. BMS 214662 may be administered in a dosage range of about 0.05 to 200 mg/kg/day, preferably less than 100 mg/kg/day in a single dose or in 2 to 4 divided doses.

C. Combination Therapy

The FTI treatment as described herein can also be used in combination with additional second therapies in selectively treating SCC in subjects having H-Ras overexpression, a higher ratio of H-Ras expression to K-Ras expression than a reference ratio, a higher ratio of H-Ras expression to N-Ras expression than a reference ratio, or a higher ratio of H-Ras expression to the combined expression of K-Ras and N-Ras than a reference ratio. The FTI treatment as described herein can also be used in combination with additional second therapies in selectively treating SCC in subjects carrying an H-Ras gene mutation. In some embodiments of the methods provided herein, the SCC is human papillomavirus (HPV)-negative. In some embodiments, the SCC is at an advanced stage. In some embodiments, the SCC is metastatic SCC. In some embodiments, the SCC is relapsed SCC. In some embodiments, the SCC is refractory. The SCC can be a specific type of SCC as described herein or otherwise known in the art. The SCC can be HNSCC. The SCC can be esophagus SCC. The SCC can be thyroid SCC. The SCC can be LSCC. The SCC can be bladder SCC. The SCC can be urothelial carcinoma (UC).

The FTI can be any FTI as described herein or otherwise known in the art. In some embodiments, the FTI can be tipifarnib, lonafarnib, arglabin, perrilyl alcohol, L778123, L739749, FTI-277, L744832, CP-609,754, 8208176, AZD3409, or BMS-214662. In some embodiments, the FTI is tipifarnib.

In some embodiments, the FTI treatment is administered in combination with radiotherapy, or radiation therapy. Radiotherapy includes using γ-rays, X-rays, and/or the directed delivery of radioisotopes to tumor cells. Other forms of DNA damaging factors are also contemplated, such as microwaves, proton beam irradiation (U.S. Pat. Nos. 5,760,395 and 4,870,287; all of which are hereby incorporated by references in their entireties), and UV-irradiation. It is most likely that all of these factors affect a broad range of damage on DNA, on the precursors of DNA, on the replication and repair of DNA, and on the assembly and maintenance of chromosomes.

In some embodiments, a therapeutically effective amount of the pharmaceutical composition having an FTI is administered that effectively sensitizes a tumor in a host to irradiation. (U.S. Pat. No. 6,545,020, which is hereby incorporated by reference in its entirety). Irradiation can be ionizing radiation and in particular gamma radiation. In some embodiments, the gamma radiation is emitted by linear accelerators or by radionuclides. The irradiation of the tumor by radionuclides can be external or internal.

Irradiation can also be X-ray radiation. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

In some embodiments, the administration of the pharmaceutical composition commences up to one month, in particular up to 10 days or a week, before the irradiation of the tumor. Additionally, irradiation of the tumor is fractionated the administration of the pharmaceutical composition is maintained in the interval between the first and the last irradiation session.

The amount of FTI, the dose of irradiation and the intermittence of the irradiation doses will depend on a series of parameters such as the type of tumor, its location, the patients' reaction to chemo- or radiotherapy and ultimately is for the physician and radiologists to determine in each individual case. In some embodiments, the FTI is administered before the administration of a radiation therapy. In some embodiments, the FTI is administered concurrently with a radiation therapy. In some embodiments, the FTI is administered after the administration of a radiation therapy. In some embodiments, the FTI is tipifarnib.

In some embodiments, the methods provided herein further include administering a therapeutically effective amount of a second active agent or a support care therapy. The second active agent can be a chemotherapeutic agent. A chemotherapeutic agent or drug can be categorized by its mode of activity within a cell, for example, whether and at what stage they affect the cell cycle. Alternatively, an agent can be characterized based on its ability to directly cross-link DNA, to intercalate into DNA, or to induce chromosomal and mitotic aberrations by affecting nucleic acid synthesis. The FTI can be administered before the administration of a second active agent. The FTI can be administered concurrently with a second active agent. The FTI can be administered after the administration of a second active agent.

Examples of chemotherapeutic agents include alkylating agents, such as thiotepa and cyclosphosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan);

bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammaI1 and calicheamicin omegaI1); dynemicin, including dynemicin A; bisphosphonates, such as clodronate; an esperamicin; as well as neocarzinostatin chromophore and related chromoprotein enediyne antibiotic chromophores, aclacinomysins, actinomycin, anthramycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids, such as retinoic acid; capecitabine; carboplatin, procarbazine, plicomycin, gemcitabine, navelbine, transplatinum, and pharmaceutically acceptable salts, acids, or derivatives of any of the above.

The second active agents can be large molecules (e.g., proteins) or small molecules (e.g., synthetic inorganic, organometallic, or organic molecules). In some embodiments, the second active agent is a DNA-hypomethylating agent, an alkylating agent, a topoisomerase inhibitor, a CDK inhibitor, a PI3K-α inhibitor, an AKT inhibitor an MTOR 1/2 inhibitor, or a therapeutic antibody that specifically binds to a cancer antigen. The second active agent can be also a hematopoietic growth factor, a cytokine, an antibiotic, a cox-2 inhibitor, an immunomodulatory agent, anti-thymocyte globulin, an immunosuppressive agent, corticosteroid or a pharmacologically active mutant or derivative thereof.

In some embodiments, the second therapy is a chemotherapy, such as cisplatin, 5-FU, carboplatin, paclitaxel, or platinum-based doublet (e.g., cisplatin/5-FU or carboplatin/paclitaxel). In some embodiments, the second therapy is taxanes and/or methotrexate. In some embodiments, the second therapy can be selected from those targeting PI3K pathway: BKM120 (buparlisib), BYL719 (PI3K-α inhibitor), Temsirolimus, Rigosertib; those targeting MET pathway: Tivantinib, Ficlatuzumab; those targeting the HER3 pathway, Patritumab; those targeting FGFR pathway: BGJ398; those targeting CDK4/6-cell cycle pathway: Palbociclib, LEE011, abemaciclib, and ribociclib; RTK inhibitor: Anlotinib; AKT inhibitors: MK2206, GSK2110183, and GSK2141795; MTOR 1/2 inhibitors: INK-128; and chemotherapy: Oral Azacitidine. In some embodiments, the second therapy is an immunotherapy, such as anti-PD 1 antibodies, anti-PDL1 antibodies, or ant-CTLA-4 antibodies. In some embodiments, the second therapy is a taxane.

In some embodiments, the second active agent is an alkylating agent, and provided herein are the combined uses of an alkylating agent and an FTI in selectively treating SCC in subjects having H-Ras overexpression, a higher ratio of H-Ras expression to K-Ras expression than a reference ratio, a higher ratio of H-Ras expression to N-Ras expression than a reference ratio, or a higher ratio of H-Ras expression to the combined expression of K-Ras and N-Ras than a reference ratio. In some embodiments, the second active agent is an alkylating agent, and provided herein are the combined uses of an alkylating agent and an FTI in selectively treating SCC in subjects carrying an H-Ras gene mutation. In some embodiments, the alkylating agent is Altretamine, Busulfan, Carboplatin, Carmustine, Chlorambucil, Cisplatin, Cyclophosphamide, Dacarbazine, Lomustine, Melphalan, Oxaliplatin, Temozolomide, or Thiotepa. In some embodiments, the FTI can be tipifarnib, lonafarnib, arglabin, perrilyl alcohol, L778123, L739749, FTI-277, L744832, CP-609, 754, R208176, AZD3409, or BMS-214662. The FTI can be administered before the administration of an alkylating agent. The FTI can be administered concurrently with an alkylating agent. The FTI can be administered after the administration of an alkylating agent.

In some embodiments, the second active agent is Cisplatin, and provided herein are the combined uses of cisplatin and an FTI in selectively treating SCC in subjects having H-Ras overexpression, a higher ratio of H-Ras expression to K-Ras expression than a reference ratio, a higher ratio of H-Ras expression to N-Ras expression than a reference ratio, or a higher ratio of H-Ras expression to the combined expression of K-Ras and N-Ras than a reference ratio. In some embodiments, the second active agent is cisplatin, and provided herein are the combined uses of cisplatin and an FTI in selectively treating SCC in subjects carrying an H-Ras gene mutation. In some embodiments, the FTI is tipifarnib, and provided herein are the combined use of cisplatin and tipifarnib in selectively treating SCC in subjects having H-Ras overexpression, a higher ratio of H-Ras expression to K-Ras expression than a reference ratio, a higher ratio of H-Ras expression to N-Ras expression than a reference ratio, or a higher ratio of H-Ras expression to the combined expression of K-Ras and N-Ras than a reference ratio. In some embodiments, the FTI is tipifarnib, and provided herein are the combined use of cisplatin and tipifarnib in selectively treating SCC in subjects carrying an H-Ras gene mutation. The tipifarnib can be administered before the administration of cisplatin. The tipifarnib can be administered concurrently with cisplatin. The tipifarnib can be administered after the administration of cisplatin.

In some embodiments, the SCC is human papillomavirus (HPV)-negative. In some embodiments, the SCC is at an advanced stage. In some embodiments, the SCC is metastatic SCC. In some embodiments, the SCC is relapsed SCC. In some embodiments, the SCC is refractory. The SCC can be a specific type of SCC as described herein or otherwise known in the art. The SCC can be HNSCC. The SCC can be esophagus SCC. The SCC can be thyroid SCC. The SCC can be LSCC. The SCC can be bladder SCC. The SCC can be urothelial carcinoma (UC). The FTI can be any FTI as described herein or otherwise known in the art. The cisplatin can be administered at a standard dose known in the art or other deemed appropriate by an oncologist. For example, the cisplatin can be administered intravenously at a daily dose of 20 mg/m$^2$, 50 mg/m$^2$, 80 mg/m$^2$, 100 mg/m$^2$, 120 mg/m$^2$, 150 mg/m$^2$, or 200 mg/m$^2$. The cisplatin can be administered weekly (QW), every 14 days (Q14D), every 21 days (Q21D), or every 28 days (Q28D). The cisplatin can be administered for at least 1 cycle, at least 2 cycles, at least 3 cycles, at least 4 cycles, at least 5 cycles, or at least 6 cycles. In some embodiments, the cisplatin is administered at a daily dose of 100 mg/m$^2$ Q21D for 3 cycles.

In some embodiments, the second active agent is a CDK inhibitor, and provided herein are the combined uses of an FTI and a CDK inhibitor in selectively treating SCC in subjects having H-Ras overexpression, a higher ratio of H-Ras expression to K-Ras expression than a reference ratio, a higher ratio of H-Ras expression to N-Ras expression than a reference ratio, or a higher ratio of H-Ras expression to the combined expression of K-Ras and N-Ras than a reference ratio. The CDK inhibitor can be palbociclib (Ibrance), ribociclib (Kisqali), or abemaciclib. The FTI can be tipifarnib, lonafarnib, arglabin, perrilyl alcohol, L778123, L739749, FTI-277, L744832, CP-609,754, R208176, AZD3409, or BMS-214662. The FTI can be administered before the administration of a CDK inhibitor. The FTI can be administered concurrently with a CDK inhibitor. The FTI can be administered after the administration of a CDK inhibitor. In some embodiments, the SCC is human papillomavirus (HPV)-negative. In some embodiments, the SCC is at an advanced stage. In some embodiments, the SCC is metastatic SCC. In some embodiments, the SCC is relapsed SCC. In some embodiments, the SCC is refractory. The SCC can be a specific type of SCC as described herein or otherwise known in the art. The SCC can be HNSCC. The SCC can be esophagus SCC. The SCC can be thyroid SCC. The SCC can be LSCC. The SCC can be bladder SCC. The SCC can be urothelial carcinoma (UC).

For example, in some embodiments, the CDK inhibitor is palbociclib, and provided herein are the combined uses of an FTI and palbociclib in selectively treating SCC in subjects having H-Ras overexpression, a higher ratio of H-Ras expression to K-Ras expression than a reference ratio, a higher ratio of H-Ras expression to N-Ras expression than a reference ratio, or a higher ratio of H-Ras expression to the combined expression of K-Ras and N-Ras than a reference ratio. In some embodiments, the FTI is tipifarnib, and provided herein are the combined uses of tipifarnib and palbociclib in selectively treating SCC in subjects having H-Ras overexpression, a higher ratio of H-Ras expression to K-Ras expression than a reference ratio, a higher ratio of H-Ras expression to N-Ras expression than a reference ratio, or a higher ratio of H-Ras expression to the combined expression of K-Ras and N-Ras than a reference ratio. In some embodiments, the SCC is human papillomavirus (HPV)-negative. In some embodiments, the SCC is at an advanced stage. In some embodiments, the SCC is metastatic SCC. In some embodiments, the SCC is relapsed SCC. In some embodiments, the SCC is refractory. The SCC can be a specific type of SCC as described herein or otherwise known in the art. The SCC can be HNSCC. The SCC can be esophagus SCC. The SCC can be thyroid SCC. The SCC can be LSCC. The SCC can be bladder SCC. The SCC can be urothelial carcinoma (UC).

The tipifarnib can be administered before the administration of palbociclib. The tipifarnib can be administered concurrently with palbociclib. The tipifarnib can be administered after the administration of palbociclib. The palbociclib can be administered at a standard dose known in the art or other deemed appropriate by an oncologist. For example, the palbociclib can be administered orally at a dose of 25 mg/day, 50 mg/day, 75 mg/day, 100 mg/day, 125 mg/day, 150 mg/day, 175 mg/day, 200 mg/day, 225 mg/day, or 250 mg/day. The palbociclib can be administered in 14 day treatment cycles or 28 day treatment cycles. In some embodiments, a 2-week treatment cycle can have 7-day dosing followed by 7-day rest. In some embodiment, a 4 week treatment cycle can have 7 day dosing, followed by 21-day rest. In some embodiment, a 4 week treatment cycle can have 21 day dosing, followed by 7-day rest. In some embodiment, a 4 week treatment cycle can have dosing on days 1-7 and 15-21, and rest on days 8-14 and 22-28. In some embodiments, the palbociclib can be administered for at least 1 cycle, at least 2 cycles, at least 3 cycles, at least 4 cycles, at least 5 cycles, or at least 6 cycles. In some embodiments, the palbociclib is administered at 125 mg/day orally on days 1-21 of a 28-day cycle.

In some embodiments, the second active agent is an EGFR inhibitor, and provided herein are the combined uses of an FTI and an EGFR inhibitor in selectively treating SCC in subjects having H-Ras overexpression, a higher ratio of H-Ras expression to K-Ras expression than a reference ratio, a higher ratio of H-Ras expression to N-Ras expression than a reference ratio, or a higher ratio of H-Ras expression to the combined expression of K-Ras and N-Ras than a reference ratio. The EGFR inhibitor can be an anti-EGFR antibody, for example, gefitinib, erlotinib, neratinib, lapatinib, vandetanib, cetuximab, necitumumab, osimertinib, or panitumumab. The FTI can be administered before the administration of an EGFR inhibitor. The FTI can be administered concurrently with an EGFR inhibitor. The FTI can be administered after the administration of an EGFR inhibitor.

In some embodiments, the second active agent is cetuximab, and provided herein are the combined use of an FTI and cetuximab in selectively treating SCC in subjects having H-Ras overexpression, a higher ratio of H-Ras expression to K-Ras expression than a reference ratio, a higher ratio of H-Ras expression to N-Ras expression than a reference ratio, or a higher ratio of H-Ras expression to the combined expression of K-Ras and N-Ras than a reference ratio. In some embodiments, the second active agent is panitumumab, and provided herein are the combined use of an FTI and panitumumab in selectively treating SCC in subjects having H-Ras overexpression, a higher ratio of H-Ras expression to K-Ras expression than a reference ratio, a higher ratio of H-Ras expression to N-Ras expression than a reference ratio, or a higher ratio of H-Ras expression to the combined expression of K-Ras and N-Ras than a reference ratio. In some embodiments, the SCC is human papillomavirus (HPV)-negative. In some embodiments, the SCC is at an advanced stage. In some embodiments, the SCC is metastatic SCC. In some embodiments, the SCC is relapsed SCC. In some embodiments, the SCC is refractory. The SCC can be a specific type of SCC as described herein or otherwise known in the art. The SCC can be HNSCC. The SCC can be esophagus SCC. The SCC can be thyroid SCC. The SCC can be LSCC. The SCC can be bladder SCC. The SCC can be urothelial carcinoma (UC).

The FTI can be any FTI as described herein or otherwise known in the art. The FTI can be tipifarnib, lonafarnib, arglabin, perrilyl alcohol, L778123, L739749, FTI-277, L744832, CP-609,754, R208176, AZD3409, or BMS-214662. In some embodiments, the FTI is tipifarnib, and provided herein are the combined use of tipifarnib and an EGFR inhibitor in selectively treating SCC in subjects having H-Ras overexpression, a higher ratio of H-Ras expression to K-Ras expression than a reference ratio, a higher ratio of H-Ras expression to N-Ras expression than a reference ratio, or a higher ratio of H-Ras expression to the combined expression of K-Ras and N-Ras than a reference ratio.

In some embodiments, provided herein are the combined use of tipifarnib and an panitumumab in selectively treating SCC in subjects having H-Ras overexpression, a higher ratio of H-Ras expression to K-Ras expression than a reference ratio, a higher ratio of H-Ras expression to N-Ras expression than a reference ratio, or a higher ratio of H-Ras expression to the combined expression of K-Ras and N-Ras than a reference ratio. In some embodiments, the SCC is at an advanced stage. In some embodiments, the SCC is metastatic SCC. In some embodiments, the SCC is relapsed SCC. In some embodiments, the SCC is refractory. The SCC can be a specific type of SCC as described herein or otherwise known in the art. The SCC can be HNSCC. The SCC can be esophagus SCC. The SCC can be thyroid SCC. The SCC can be LSCC. The SCC can be bladder SCC. The SCC can be urothelial carcinoma (UC).

The tipifarnib can be administered before the administration of panitumumab. The tipifarnib can be administered concurrently with panitumumab. The tipifarnib can be administered after the administration of panitumumab. The panitumumab can be administered at a standard dose known in the art or other deemed appropriate by an oncologist. For example, the panitumumab can be administered orally at a daily dose of 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, or 18 mg/kg body weight. The cetuximab can be administered weekly (QW), every 14 days (Q14D), every 21 days (Q21D), or every 28 days (Q28D). The panitumumab can be administered for at least 1 cycle, at least 2 cycles, at least 3 cycles, at least 4 cycles, at least 5 cycles, or at least 6 cycles. In some embodiments, the panitumumab is administered at 6 mg/kg Q14D.

In some embodiments, provided herein are the combined use of tipifarnib and cetuximab in selectively treating SCC in subjects having H-Ras overexpression, a higher ratio of H-Ras expression to K-Ras expression than a reference ratio, a higher ratio of H-Ras expression to N-Ras expression than a reference ratio, or a higher ratio of H-Ras expression to the combined expression of K-Ras and N-Ras than a reference ratio. In some embodiments, the SCC is at an advanced stage. In some embodiments, the SCC is metastatic SCC. In some embodiments, the SCC is relapsed SCC. In some embodiments, the SCC is refractory. The SCC can be a specific type of SCC as described herein or otherwise known in the art. The SCC can be HNSCC. The SCC can be esophagus SCC. The SCC can be thyroid SCC. The SCC can be LSCC. The SCC can be bladder SCC. The SCC can be urothelial carcinoma (UC).

The tipifarnib can be administered before the administration of cetuximab. The tipifarnib can be administered concurrently with cetuximab. The tipifarnib can be administered after the administration of cetuximab. The cetuximab can be administered at a standard dose known in the art or other deemed appropriate by an oncologist. For example, the cetuximab can be administered orally at a daily dose of 50 mg/m$^2$, 100 mg/m$^2$, 150 mg/m$^2$, 200 mg/m$^2$, 250 mg/m$^2$ 300 mg/m$^2$, 350 mg/m$^2$, 400 mg/m$^2$, 450 mg/m$^2$, or 500 mg/m$^2$. The cetuximab can be administered weekly (QW), every 14 days (Q14D), every 21 days (Q21D), or every 28 days (Q28D). The cetuximab can be administered with a loading dose followed by the standard dose. The loading dose can be at least 1.5 fold, 2 fold, 2.5 fold, 3 fold greater than the standard dose. In some embodiments, the loading dose can be 400 mg/m$^2$, 450 mg/m$^2$, 500 mg/m$^2$, 600 mg/m$^2$, 700 mg/m$^2$, 800 mg/m$^2$, 900 mg/m$^2$ or 1000 mg/m$^2$. The cetuximab can be administered for at least 1 cycle, at least 2 cycle, at least 3 cycle, at least 4 cycle, at least 5 cycle, or at least 6 cycle. In some embodiments, the cetuximab is administered at 400 mg/m$^2$ loading dose followed by 250 mg/m$^2$ QW.

In some embodiments, the second active agent targets the PI3K pathway, and provided herein are the combined uses of a PI3K pathway targeting agent and an FTI in selectively treating SCC in subjects having H-Ras overexpression, a higher ratio of H-Ras expression to K-Ras expression than a reference ratio, a higher ratio of H-Ras expression to N-Ras expression than a reference ratio, or a higher ratio of H-Ras expression to the combined expression of K-Ras and N-Ras than a reference ratio. In some embodiments, the second active agent targets the PI3K pathway, and provided herein are the combined uses of a PI3K pathway targeting agent and an FTI in selectively treating SCC in subjects carrying an H-Ras gene mutation. In some embodiments, the second active agent targets the PI3K pathway, and provided herein are the combined uses of a PI3K pathway targeting agent and an FTI in selectively treating SCC in subjects carrying an H-Ras gene mutation and a PIK3CA gene mutation. In some embodiments, the PI3K pathway targeting agent is BKM120 (buparlisib), BYL719 (PI3K-α inhibitor), Temsirolimus, or Rigosertib. In some embodiments, the PI3K pathway targeting agent is a PI3K-α inhibitor. In some embodiments, the FTI can be tipifarnib, lonafarnib, arglabin, perrilyl alcohol, L778123, L739749, FTI-277, L744832, CP-609,754, R208176, AZD3409, or BMS-214662. The FTI can be administered before the administration of a PI3K pathway targeting agent. The FTI can be administered concurrently with a PI3K pathway targeting agent. The FTI can be administered after the administration of a PI3K pathway targeting agent. The FTI can be administered before the administration of a PI3K-α inhibitor. The FTI can be administered concurrently with a PI3K-α inhibitor. The FTI can be administered after the administration of a PI3K-α inhibitor.

In some embodiments, the PI3K-α inhibitor is BYL719, and provided herein are the combined uses of BYL719 and an FTI in selectively treating SCC in subjects having H-Ras overexpression, a higher ratio of H-Ras expression to K-Ras expression than a reference ratio, a higher ratio of H-Ras expression to N-Ras expression than a reference ratio, or a higher ratio of H-Ras expression to the combined expression of K-Ras and N-Ras than a reference ratio. In some embodiments, the second active agent is BYL719, and provided herein are the combined uses of BYL719 and an FTI in selectively treating SCC in subjects carrying an H-Ras gene mutation. In some embodiments, the second active agent is BYL719, and provided herein are the combined uses of BYL719 and an FTI in selectively treating SCC in subjects carrying an H-Ras gene mutation and a PIK3CA gene mutation. In some embodiments, the FTI is tipifarnib, and provided herein are the combined use of BYL719 and tipifarnib in selectively treating SCC in subjects having H-Ras overexpression, a higher ratio of H-Ras expression to K-Ras expression than a reference ratio, a higher ratio of H-Ras expression to N-Ras expression than a reference ratio, or a higher ratio of H-Ras expression to the combined expression of K-Ras and N-Ras than a reference ratio. In some embodiments, the FTI is tipifarnib, and provided herein are the combined use of BYL719 and tipifarnib in selectively treating SCC in subjects carrying an H-Ras gene mutation. In some embodiments, the FTI is tipifarnib, and provided herein are the combined use of BYL719 and tipifarnib in selectively treating SCC in subjects carrying an H-Ras gene mutation and a PIK3CA gene mutation. The tipifarnib can be administered before the administration of BYL719. The tipifarnib can be administered concurrently with BYL719. The tipifarnib can be administered after the administration of BYL719.

In some embodiments, the SCC is human papillomavirus (HPV)-negative. In some embodiments, the SCC is at an advanced stage. In some embodiments, the SCC is metastatic SCC. In some embodiments, the SCC is relapsed SCC. In some embodiments, the SCC is refractory. The SCC can be a specific type of SCC as described herein or otherwise known in the art. The SCC can be HNSCC. The SCC can be esophagus SCC. The SCC can be thyroid SCC. The SCC can be LSCC. The SCC can be bladder SCC. The SCC can be urothelial carcinoma (UC).

In some embodiments, the second active agent is an AKT inhibitor, and provided herein are the combined uses of an AKT inhibitor and an FTI in selectively treating SCC in subjects having H-Ras overexpression, a higher ratio of H-Ras expression to K-Ras expression than a reference ratio, a higher ratio of H-Ras expression to N-Ras expression than a reference ratio, or a higher ratio of H-Ras expression to the combined expression of K-Ras and N-Ras than a reference ratio. In some embodiments, the second active agent is an AKT inhibitor, and provided herein are the combined uses of an AKT inhibitor and an FTI in selectively treating SCC in subjects carrying an H-Ras gene mutation. In some embodiments, the AKT inhibitor is MK2206, GSK2110183, or GSK2141795. In some embodiments, the FTI can be tipifarnib, lonafarnib, arglabin, perrilyl alcohol, L778123, L739749, FTI-277, L744832, CP-609,754, R208176, AZD3409, or BMS-214662. The FTI can be administered before the administration of an AKT inhibitor. The FTI can be administered concurrently with an AKT inhibitor. The FTI can be administered after the administration of an AKT inhibitor.

In some embodiments, the AKT inhibitor is GSK2141795, and provided herein are the combined uses of GSK2141795 and an FTI in selectively treating SCC in subjects having H-Ras overexpression, a higher ratio of H-Ras expression to K-Ras expression than a reference ratio, a higher ratio of H-Ras expression to N-Ras expression than a reference ratio, or a higher ratio of H-Ras expression to the combined expression of K-Ras and N-Ras than a reference ratio. In some embodiments, the second active agent is GSK2141795, and provided herein are the combined uses of GSK2141795 and an FTI in selectively treating SCC in subjects carrying an H-Ras gene mutation. In some embodiments, the FTI is tipifarnib, and provided herein are the combined use of GSK2141795 and tipifarnib in selectively treating SCC in subjects having H-Ras overexpression, a higher ratio of H-Ras expression to K-Ras expression than a reference ratio, a higher ratio of H-Ras expression to N-Ras expression than a reference ratio, or a higher ratio of H-Ras expression to the combined expression of K-Ras and N-Ras than a reference ratio. In some embodiments, the FTI is tipifarnib, and provided herein are the combined use of GSK2141795 and tipifarnib in selectively treating SCC in subjects carrying an H-Ras gene mutation. The tipifarnib can be administered before the administration of GSK2141795. The tipifarnib can be administered concurrently with GSK2141795. The tipifarnib can be administered after the administration of GSK2141795.

In some embodiments, the SCC is human papillomavirus (HPV)-negative. In some embodiments, the SCC is at an advanced stage. In some embodiments, the SCC is metastatic SCC. In some embodiments, the SCC is relapsed SCC. In some embodiments, the SCC is refractory. The SCC can be a specific type of SCC as described herein or otherwise known in the art. The SCC can be HNSCC. The SCC can be esophagus SCC. The SCC can be thyroid SCC. The SCC can be LSCC. The SCC can be bladder SCC. The SCC can be urothelial carcinoma (UC).

In some embodiments, the second active agent is an MTOR 1/2 inhibitor, and provided herein are the combined uses of an MTOR 1/2 inhibitor and an FTI in selectively treating SCC in subjects having H-Ras overexpression, a higher ratio of H-Ras expression to K-Ras expression than a reference ratio, a higher ratio of H-Ras expression to N-Ras expression than a reference ratio, or a higher ratio of H-Ras expression to the combined expression of K-Ras and N-Ras than a reference ratio. In some embodiments, the second active agent is an MTOR 1/2 inhibitor, and provided herein are the combined uses of an MTOR 1/2 inhibitor and an FTI in selectively treating SCC in subjects carrying an H-Ras gene mutation. In some embodiments, the MTOR 1/2 inhibitor is INK-128. In some embodiments, the FTI can be tipifarnib, lonafarnib, arglabin, perrilyl alcohol, L778123, L739749, FTI-277, L744832, CP-609,754, R208176, AZD3409, or BMS-214662. The FTI can be administered before the administration of an MTOR 1/2 inhibitor. The FTI can be administered concurrently with an MTOR 1/2 inhibitor. The FTI can be administered after the administration of an MTOR 1/2 inhibitor.

In some embodiments, the MTOR 1/2 inhibitor is INK-128, and provided herein are the combined uses of INK-128 and an FTI in selectively treating SCC in subjects having H-Ras overexpression, a higher ratio of H-Ras expression to K-Ras expression than a reference ratio, a higher ratio of H-Ras expression to N-Ras expression than a reference ratio, or a higher ratio of H-Ras expression to the combined expression of K-Ras and N-Ras than a reference ratio. In some embodiments, the second active agent is INK-128, and provided herein are the combined uses of INK-128 and an FTI in selectively treating SCC in subjects carrying an H-Ras gene mutation. In some embodiments, the FTI is tipifarnib, and provided herein are the combined use of INK-128 and tipifarnib in selectively treating SCC in subjects having H-Ras overexpression, a higher ratio of H-Ras expression to K-Ras expression than a reference ratio, a higher ratio of H-Ras expression to N-Ras expression than a reference ratio, or a higher ratio of H-Ras expression to the combined expression of K-Ras and N-Ras than a reference ratio. In some embodiments, the FTI is tipifarnib, and provided herein are the combined use of INK-128 and tipifarnib in selectively treating SCC in subjects carrying an H-Ras gene mutation. The tipifarnib can be administered before the administration of INK-128. The tipifarnib can be administered concurrently with INK-128. The tipifarnib can be administered after the administration of INK-128.

In some embodiments, the SCC is human papillomavirus (HPV)-negative. In some embodiments, the SCC is at an advanced stage. In some embodiments, the SCC is metastatic SCC. In some embodiments, the SCC is relapsed SCC. In some embodiments, the SCC is refractory. The SCC can be a specific type of SCC as described herein or otherwise known in the art. The SCC can be HNSCC. The SCC can be esophagus SCC. The SCC can be thyroid SCC. The SCC can be LSCC. The SCC can be bladder SCC. The SCC can be urothelial carcinoma (UC).

In some embodiments, the second active agent is a DNA hypomethylating agent, such as a cytidine analog (e.g., azacitidine) or a 5-azadeoxycytidine (e.g. decitabine). In some embodiments, the second active agent is a cytoreductive agent, including but not limited to Induction, Topotecan, Hydrea, PO Etoposide, Lenalidomide, LDAC, and Thioguanine. In some embodiments, the second active agent is Mitoxantrone, Etoposide, Cytarabine, or Valspodar. In some embodiment, the second active agent is Mitoxantrone plus Valspodar, Etoposide plus Valspodar, or Cytarabine plus Valspodar. In some embodiment, the second active agent is idarubicin, fludarabine, topotecan, or ara-C. In some other embodiments, the second active agent is idarubicin plus ara-C, fludarabine plus ara-C, mitoxantrone plus ara-C, or topotecan plus ara-C. In some embodiments, the second active agent is a quinine. Other combinations of the agents specified above can be used, and the dosages can be determined by the physician.

Treatments as described herein or otherwise available in the art can be used in combination with the FTI treatment. For example, drugs that can be used in combination with the FTI include belinostat (Beleodaq®) and pralatrexate (Folotyn®), marketed by Spectrum Pharmaceuticals, romidepsin (Istodax®), marketed by Celgene, and brentuximab vedotin (Adcetris®), marketed by Seattle Genetics; azacytidine (Vidaza®) and lenalidomide (Revlimid®), marketed by Celgene, and decitabine (Dacogen®) marketed by Otsuka and Johnson & Johnson; vandetanib (Caprelsa®), Bayer's sorafenib (Nexavar®), Exelixis' cabozantinib (Cometriq®) and Eisai's lenvatinib (Lenvima®).

Non-cytotoxic therapies such as pralatrexate (Folotyn®), romidepsin (Istodax®) and belinostat (Beleodaq®) can also be used in combination with the FTI treatment.

In some embodiments, the secondary active agent is a DNA-hypomethylating agent. In some embodiments, the secondary active agent is cytarabine, daurubicin, idarubicin, or gentuzumab, or ozogamicin. In some embodiments, the secondary active agent is a DNA-hypomethylating agent, such as azacitidine or decitabine.

In some embodiments, the second active agent is an immunotherapy agent. In some embodiments, the second active agent is anti-PD1 antibody. In some embodiments, the second active agent is an anti-PDL1 antibody. In some embodiments, the second active agent is an anti-CTLA-4 antibody.

In some embodiments, it is contemplated that the second active agent or second therapy used in combination with a FTI can be administered before, at the same time, or after the FTI treatment. In some embodiments, the second active agent or second therapy used in combination with a FTI can be administered before the FTI treatment. In some embodiments, the second active agent or second therapy used in combination with a FTI can be administered at the same time as FTI treatment. In some embodiments, the second active agent or second therapy used in combination with a FTI can be administered after the FTI treatment.

In some embodiments, the FTI treatment is administered in combination with a bone marrow transplant. In some embodiments, the FTI is administered before the administration of a bone marrow transplant. In some embodiments, the FTI is administered concurrently with a bone marrow transplant. In some embodiments, the FTI is administered after the administration of a bone marrow transplant.

In some embodiments, the FTI treatment is administered in combination with a stem cell transplant. In some embodiments, the FTI is administered before the administration of a stem cell transplant. In some embodiments, the FTI is administered concurrently with a stem cell transplant. In some embodiments, the FTI is administered after the administration of a stem cell transplant.

A person of ordinary skill in the art would understand that the methods described herein include using any permutation or combination of the specific FTI, formulation, dosing regimen, additional therapy to treat a subject described herein.

It is understood that modifications which do not substantially affect the activity of the various embodiments of this invention are also provided within the definition of the invention provided herein. Accordingly, the following examples are intended to illustrate but not limit the present invention. All of the references cited to herein are incorporated by reference in their entireties.

Example I

Increased In Vivo Efficacy of Tipifarnib in HNSCC with High H-Ras Expression or High H/N+K Ratios Female BALB/c nude or Nu/nu mice (6-8 weeks) were inoculated subcutaneously on the right flank with primary human tumor model fragment (2-3 mm in diameter) for tumor development. When average tumor size reaches about 250-350 mm$^3$, mice were randomly grouped into dosing groups. Animals were dosed with tipifarnib vehicle (20% w/v Hydroxypropyl-β-cyclodextrin) or tipifarnib at a dose of 80 mg/kg BID PO for 3-4 weeks and tumor dimensions were measured twice per week.

The ability of tipifarnib to inhibit tumor growth was determined using selected patient-derived xenograft (PDX) models of HNSCC. The selected models expressed different levels of H-Ras or had different high ratios of H-Ras expression to the combined expression of K-Ras and N-Ras ("H/K+N ratio"). The expression levels of H-Ras, K-Ras and N-Ras in these PDX models were determined by RNAseq. These H-Ras expression level and H/K+N ratios of these models are summarized in Table 1. All models in Table 1 express wild type H-Ras.

TABLE 1

H-Ras expression levels and H-Ras:K-Ras + N-Ras Ratios ("H/K + N") in PDX Models

| PDX Model | Cancer Type | H-Ras expression (fold median)* | H/K + N ** |
|---|---|---|---|
| HN0586 | HNSCC | 2.1 | 2.9 |
| HN2222 | HNSCC | 0.49 | 0.48 |
| HN2576 | HNSCC | 3.0 | 4.6 |
| HN2593 | HNSCC | 3.4 | 4.5 |
| HN2594 | HNSCC | 2.8 | 3.6 |
| HN3067 | HNSCC | 2.7 | 2.8 |
| HN3411 | HNSCC | 4.1 | 2.7 |
| HN3461 | HNSCC | 2.1 | 2.4 |
| HN3474 | HNSCC | 2.4 | 5.5 |
| HN3679 | HNSCC | 2.6 | 3.6 |
| HN3690 | HNSCC | 3.1 | 3.5 |
| HN3776 | HNSCC | 2.2 | 2.7 |
| HN3792 | HNSCC | 2.5 | 3.4 |
| HN5111 | HNSCC | 1.3 | 2.2 |
| HN5115 | HNSCC | ND | ND |
| HN5123 | HNSCC | 1.6 | 2.1 |
| ES0204 | ESCC | 3.1 | 6.3 |
| ES0172 | ESCC | 2.2 | 6.3 |
| BR1282 | Breast Cancer | 3.6 | 22.6 |
| BR1458 | Breast Cancer | 1.4 | 10.4 |

*H-Ras expression data expressed relative to the median expression of H-Ras in Crown Bio PDX cohort (n = 866); ND is not determined;
** Median H/K + N ratio in Crown Bio HNSCC PDX cohort (n = 66) = 2.8; median H/K + N ratio in Crown Bio ESCC PDX cohort (n = 32) = 2.7; median H/K + N ratio in Crown Bio breast cancer PDX cohort (n = 27) = 3.1; median H/K + N ratio in Crown Bio breast cancer PDX cohort without two outliers BR1282 and BR1458 (n = 25) = 2.0; ND is not determined.

Figure 1B:
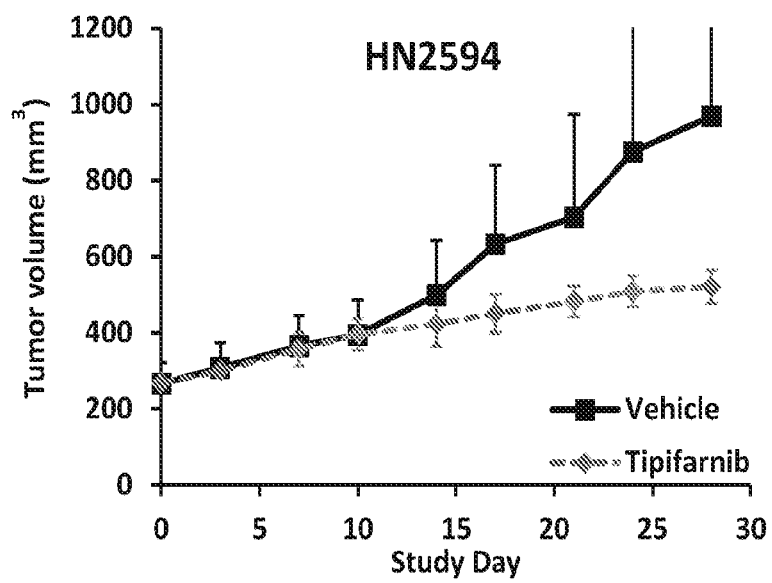
Figure 1C:
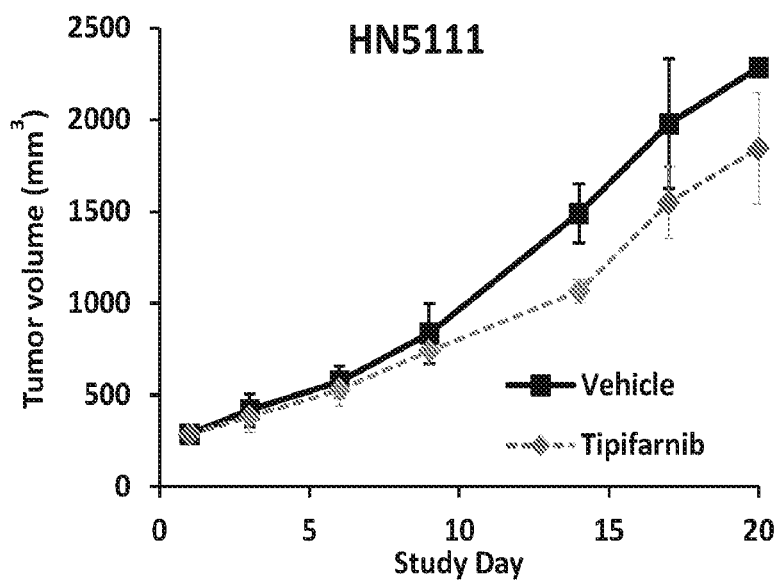
Figure 1D:
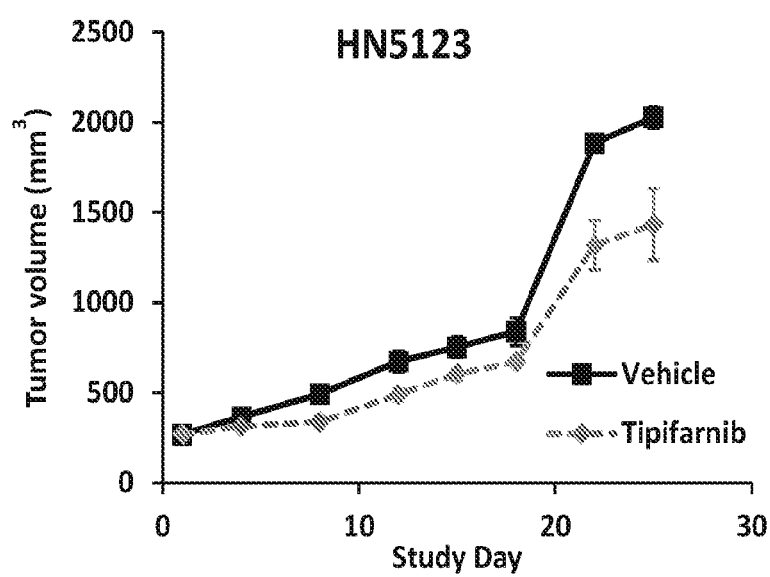

FIGS. 1A-1D show the efficacy of tipifarnib in HNSCC PDX models with different H-Ras expression levels and different H/K+N ratios. As shown, the HNSCC PDX models with relatively high H-Ras expression and/or high H/K+N ratio (HN2576 and HN2594) were more responsive to tipifarnib treatment (FIGS. 1A and 1B) as compared to those with relatively low H-Ras expression and/or low H/K+N ratio (HN5111 and HN5123; FIGS. 1C and 1D). Notably, tipifarnib significantly inhibited tumor growth in models HN2576 and HN2594, and even induced tumor regression in model HN2576 (FIGS. 1A and 1B). Although tipifarnib also inhibited tumor growth in models HN5111 and HN5123 as compared to the vehicle control, its efficacy was significantly less pronounced than that in models HN2576 or HN2594.

FIGS. 5A-5D show the efficacy of tipifarnib in HNSCC PDX models with high H-Ras expression levels of wild type H-Ras. As shown, the HNSCC PDX models having relatively high H-Ras expression FIG. 5A (HN2576), FIG. 5B (HN2594), FIG. 5C (HN3461), and FIG. 5D (HN3679), having 213, 138, 104, and 125 units (units expressed as H-Ras Expression RNAseq V2 (linear)), respectively, were more responsive to tipifarnib treatment as compared to those with relatively low H-Ras expression (HN5111 and HN5123; FIGS. 1C and 1D, respectively). Notably, tipifarnib significantly inhibited tumor growth in each of models HN2576, HN2594, HN3461, and HN3679.

FIGS. 6A-6D show the efficacy of tipifarnib in HNSCC PDX models with low H-Ras expression levels of wild type H-Ras. As shown, the HNSCC PDX models having relatively low H-Ras expression FIG. 6A (HN2222), FIG. 6B (HN5111), FIG. 6C (HN5115), and FIG. 6D (HN5123), having 24, 57, ND, and 65 units (units expressed as H-Ras Expression RNAseq V2 (linear)), respectively, were inactive or less responsive to tipifarnib treatment as compared to those with relatively high H-Ras expression (FIGS. 1C, 1D, and FIGS. 5A-5D). Although tipifarnib also inhibited tumor growth in models HN2222, HN5111, HN5115, and HN5123, as compared to the vehicle control, its efficacy was significantly less pronounced than that in models HN2576, HN2594, HN3461, and HN3679.

Example II

Figure 2A:
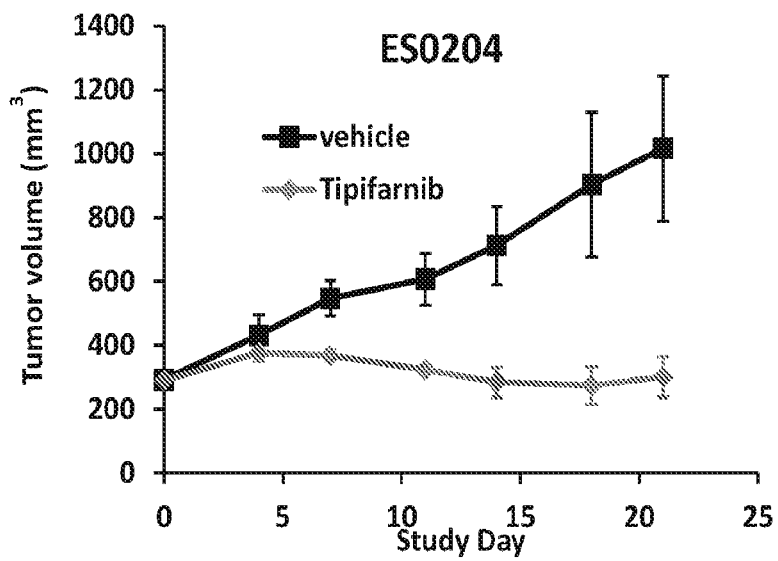
FIGS. 2A-2D. Increased efficacy of tipifarnib in ESCC but not breast cancer PDX models with high H-Ras/K-Ras+ N-Ras ratios.
Figure 2B:
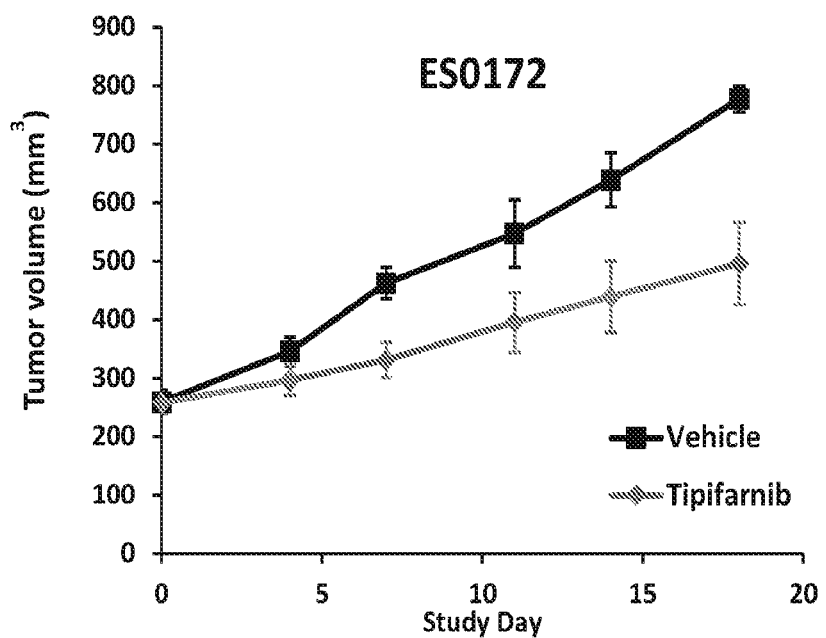
Figure 2C:
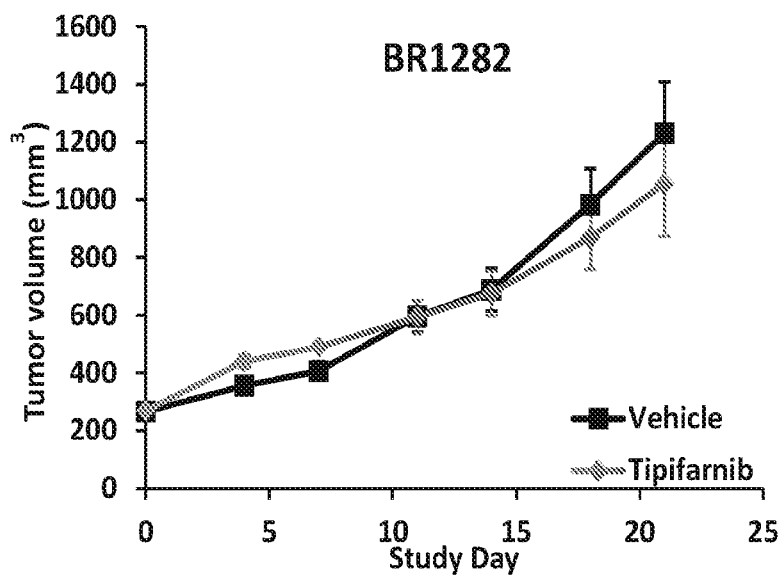
Figure 2D:
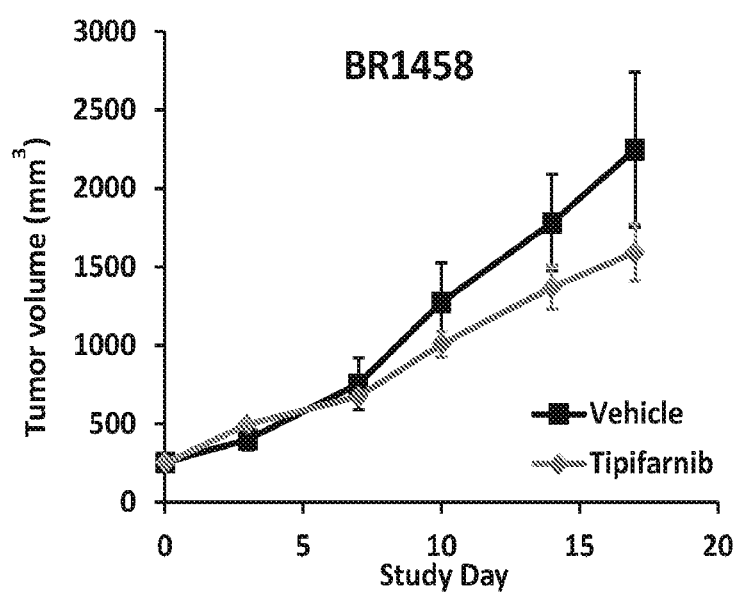

Increased In Vivo Efficacy of Tipifarnib in Esophagus Squamous Cell Carcinoma but not Breast Cancer with High H/N+K Ratios As described in Example 1, nude mice were inoculated subcutaneously on the flank with either a PDX model of esophagus squamous cell carcinoma (ESCC) (ES0204 or ES0172), or a PDX model of breast cancer (BR1282 or BR1458). The H/K+N ratios of these models are detailed in Table 1. As shown in FIG. 2A and FIG. 2B, tipifarnib effectively inhibited the tumor growth in both ES0172 (p=0.02) and ES0204 (p=0.04) models having relatively high H/K+N ratio (FIG. 2A). Such efficacy, however, was not observed in either the BR1282 (p=0.53) or BR1458 (p=0.28) breast cancer PDX models, although these models also had relatively high H/K+N ratios (FIG. 2C and FIG. 2D). As such, high H-Ras expression or high H/K+N ratio specifically correlated with the FTI (e.g. tipifarnib) efficacy in SCCs, such as HNSCC, ESCC, and urothelial carcinoma, but not other non-squamous type of cancers such as breast cancer.

Example III

Synergistic Effect of Tipifarnib and Second Therapies in HNSCC with High H-Ras Expression or High H/N+K Ratios As described in Example I, mice were inoculated subcutaneously on the flank with PDX HNSCC models (HN3411 and HN2594). After tumor development, mice were administered either vehicle, tipifarnib, a second active agent, or a combination of tipifarnib and a second active agent. The second agent was either the alkylating agent cisplatin, the EGFR inhibitor cetuximab, or the CDK inhibitor palbociclib. In the HN3411 model (H-Ras=4.1×median; H/K+N=2.7), as shown, neither cisplatin (FIG. 3B) nor palbociclib (FIG. 3C) had any activity when used alone. When combined with tipifarnib, however, both cisplatin and palbociclib resulted in further inhibition of tumor growth as compared to tipifarnib alone (FIGS. 3B and 3C). As such, tipifarnib not only directly inhibited tumor growth in HNSCC, but also sensitized the tumor to other treatments, such as cisplatin or palbociclib.

Figure 3A:
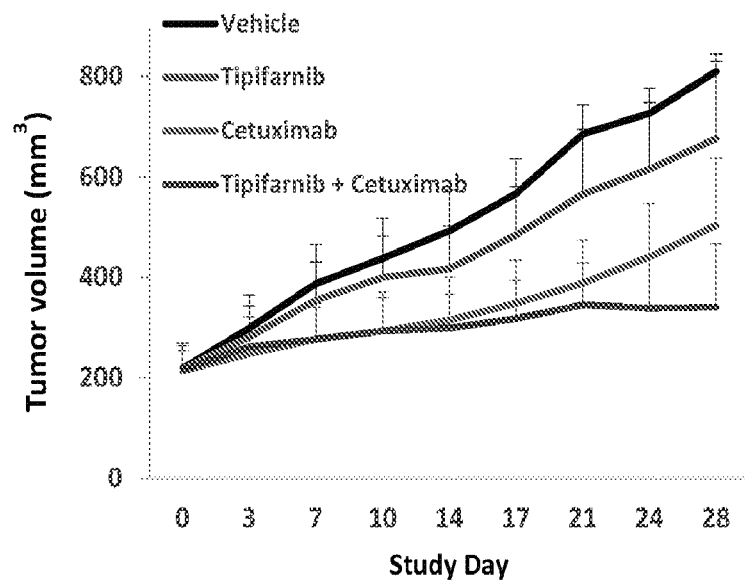
FIGS. 3A-3C. Combination treatment of tipifamib and a second agent synergistically inhibited tumor growth in HNSCC PDX Model HN3411 (H-Ras=4.1×median; H/K+ N=2.7).
Figure 3B:
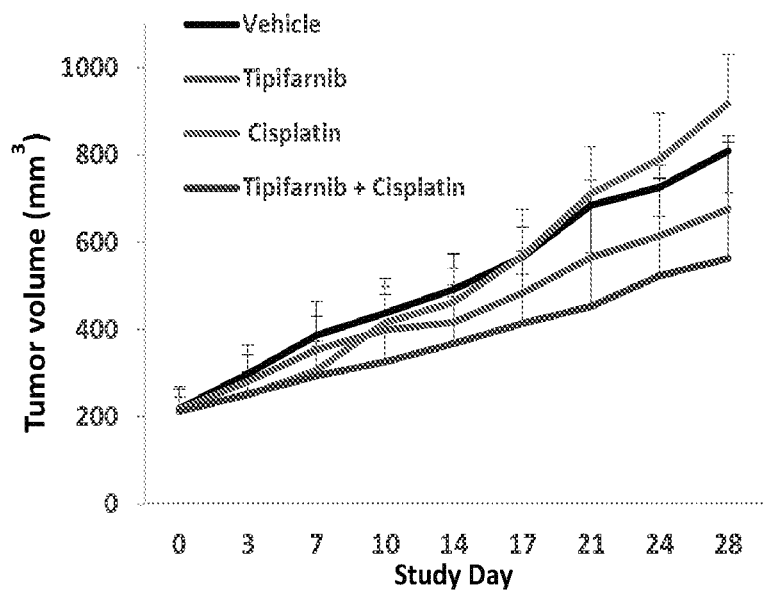
Figure 3C:
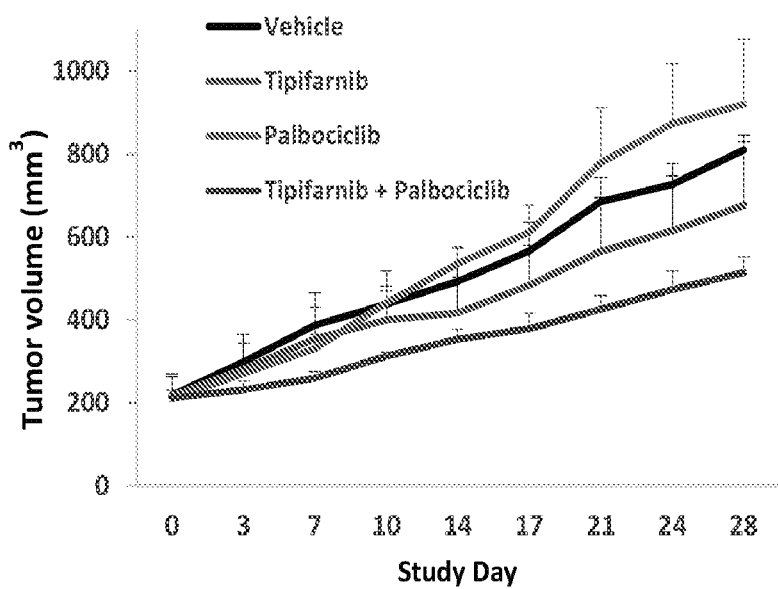

Both cetuximab and tipifarnib partially inhibited tumor growth as a single agent (FIG. 3A). When combined, near-stasis of tumor growth was observed in the HN3411 model, evidencing the synergistic activity of both agents (FIG. 3A).

Figure 4A:
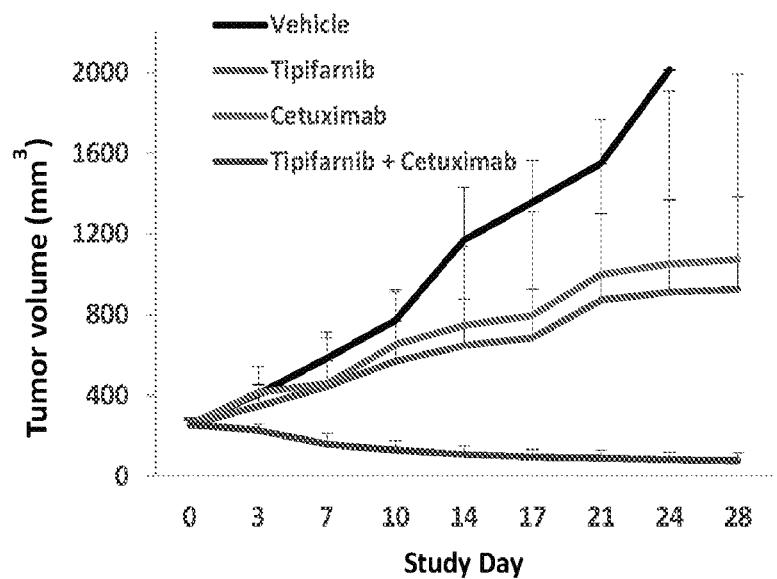
FIGS. 4A-4C. Combination treatment of tipifarnib and a second agent synergistically inhibited tumor growth in HNSCC PDX Model HN2594 (H-Ras=2.8×median; H/K+ N=3.6).
Figure 4B:
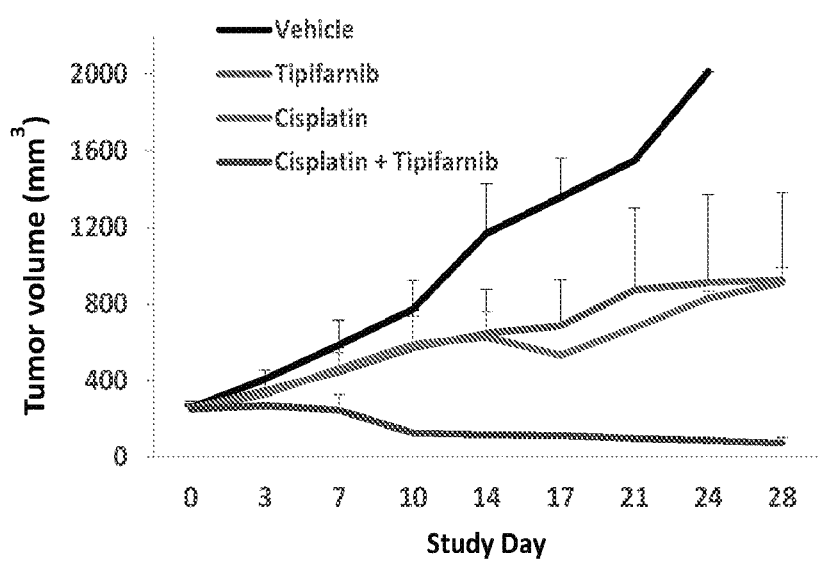
Figure 4C:
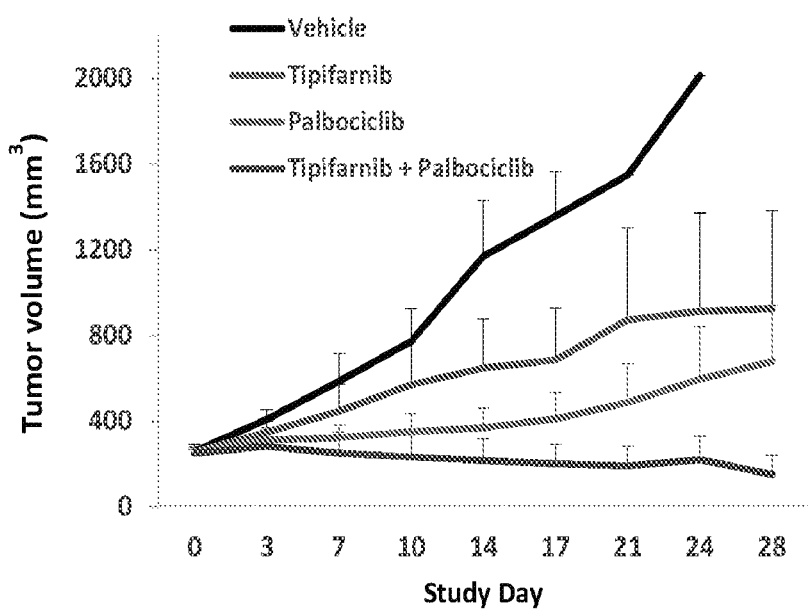
Figure 5A:
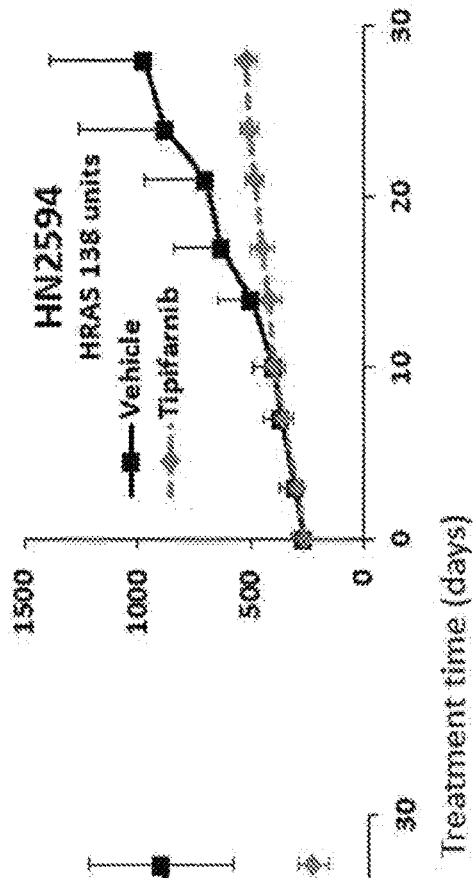
FIGS. 5A-5D. Increased efficacy of tipifarnib in HNSCC PDX models with high H-Ras expression levels or high H-Ras/K-Ras+N-Ras ("H/K+N") ratios.
Figure 5B:
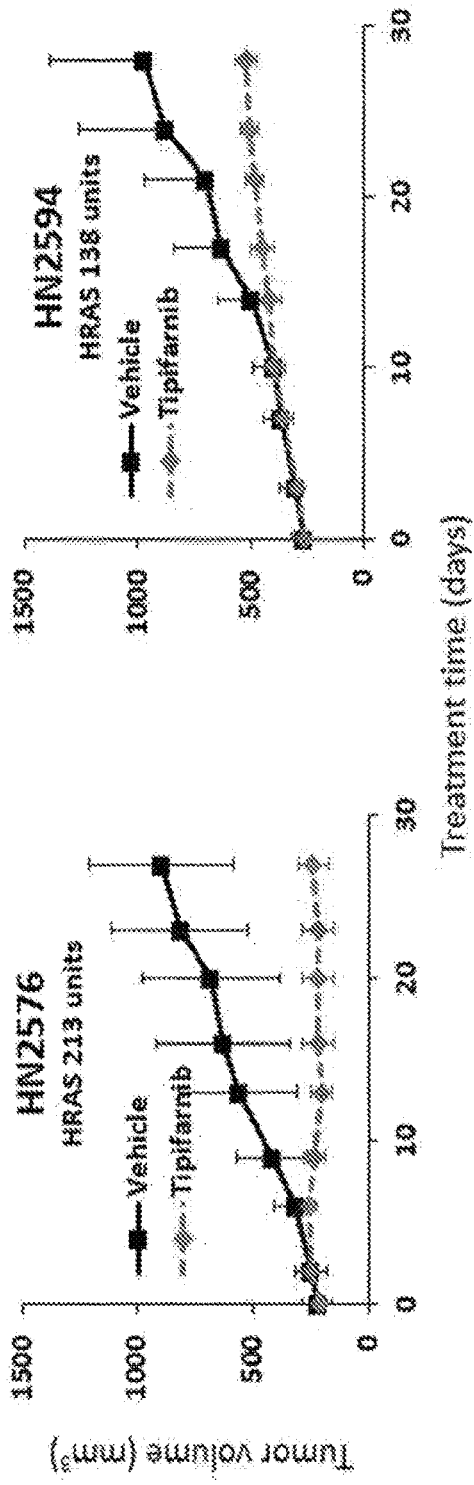
Figure 5C:
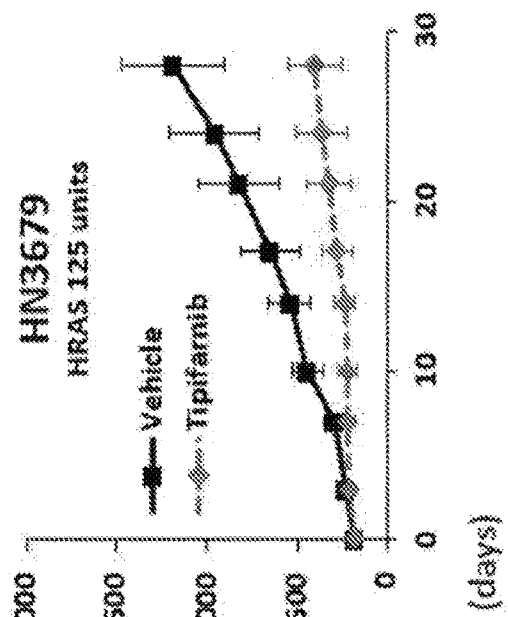
Figure 5D:
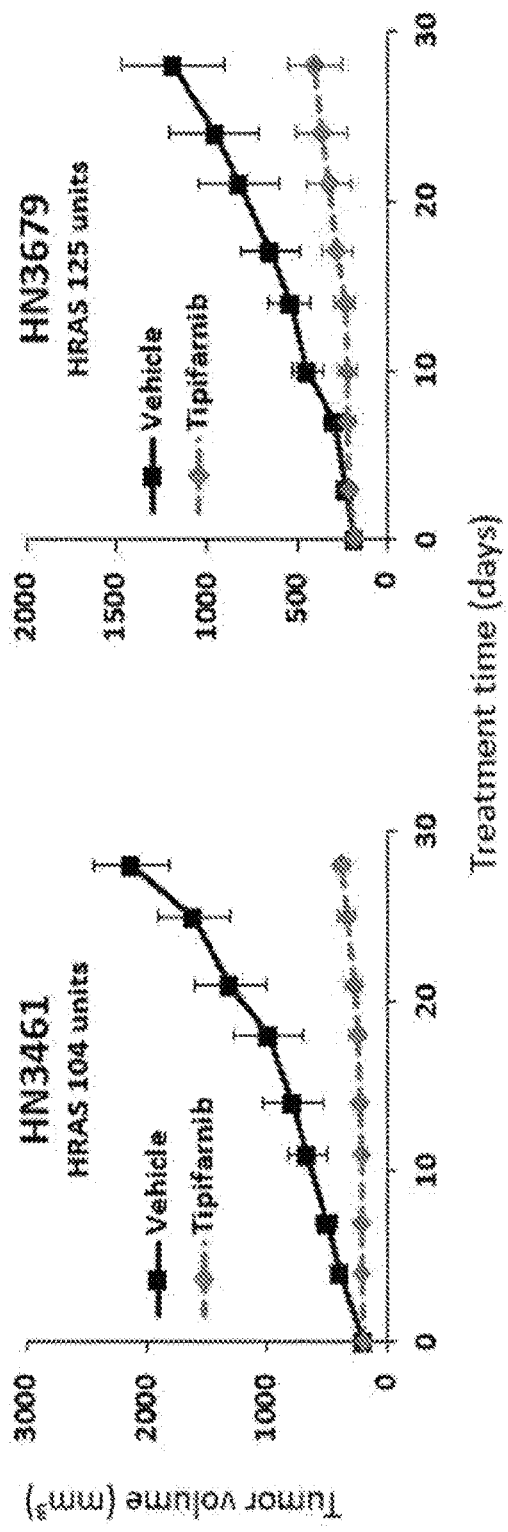

The synergistic effects of tipifarnib and a second agent were also observed in the HNSCC model HN2594 (H-Ras=2.8×median; H/K+N=3.6; FIGS. 4A-4C). As shown, while tipifarnib alone or the second therapy (cetuximab, cisplatin, or palbociclib) alone achieved partial response (inhibited tumor growth), all combinations induced tumor regression (FIGS. 4A-4C).

Example IV

Effect of Tipifarnib and Second Therapies in HNSCC with H-Ras Mutant Expression

The ability of tipifarnib in combination with a second therapy to inhibit tumor growth was determined using selected patient-derived xenograft (PDX) models of HNSCC, wherein the selected models expressed mutated H-Ras. The expression levels of the H-Ras mutants in these PDX models were determined by RNAseq. These H-Ras mutant expression level and H/K+N ratios of these models are summarized in Table 2. All models in Table 2 express mutant H-Ras.

TABLE 2

H-Ras mutant expression levels, H/K + N Ratios, and H-Ras Mutations in PDX Models

| PDX Model | Cancer Type | H-Ras expression (fold median)* | H/K + N ** | Mutation*** |
|---|---|---|---|---|
| HN1420 | HNSCC | 8.8 | 10.4 | HRAS A146P |
| HN2579 | HNSCC | 2.2 | 2.8 | HRAS G12S |
| HN2581 | HNSCC | 3.1 | 3.7 | HRAS G13C |
| HN3504 | HNSCC | 2.3 | 3.3 | HRAS K117L |

*HNSCC data expressed relative to the median expression of H-Ras in Crown Bio HNSCC PDX cohort (n = 886);
** Median H/K + N ratio in Crown Bio HNSCC PDX cohort (n = 66) = 2.8;
***Mutation is or comprises a modification in a codon of the H-Ras gene that encodes an amino acid substitution at the specified position in the corresponding mutant H-Ras protein.

As described in Example I, mice were inoculated subcutaneously on the flank with PDX HNSCC models (HN2579, HN2581, HN1420, and HN3504, having a mutation that is or comprises a modification in a codon of the mutant H-Ras gene encoding an amino acid at the specified position to provide the resulting mutated H-Ras protein HRAS G12S, HRAS G13C, HRAS A146P, and HRAS K117L, respectively). After tumor development, mice were administered either vehicle, tipifarnib (80 mg/kg PO BID), a second active agent, or a combination of tipifarnib and a second active agent. The second agent was alkylating agent cisplatin (3 mg/kg IP QW). Cisplatin monotherapy had activity in the HN2579 model (FIG. 7A) and the HN2581 model (FIG. 7B), but was inactive in the HN1420 model (FIG. 7C) and the HN3504 model (FIG. 7D), relative to vehicle. Tipifarnib monotherapy had high activity and induced tumor regression in each of the four models, relative to vehicle (FIGS. 7A-7D). When cisplatin was combined with tipifarnib, it resulted in further inhibition of tumor growth as compared to tipifarnib alone in those models where cisplatin monotherapy had shown activity (FIGS. 7A and 7B), whereas the combination therapy was no better than the tipifarnib monotherapy in those models where cisplatin monotherapy was inactive (FIGS. 7C and 7D). As such, tipifarnib not only directly inhibited tumor growth in HNSCC having H-Ras mutant expression (FIGS. 7A-7D), but also sensitized the tumor to cisplatin treatments, where the tumor is shown to have some sensitivity to cisplatin (FIGS. 7A and 7B).

Example V

Effect of Tipifarnib and Second Therapies in HNSCC with High H-Ras Expression and/or High H/N+K Ratios As described in Example I, mice were inoculated subcutaneously on the flank with PDX HNSCC models HN3792, HN0586, HN2576, HN3067, HN2594, HN3461, HN3776, HN3474, and HN3679, with each of the nine models having high H-Ras expression level and/or high H/N+K Ratios, as detailed in Table 1). After tumor development, mice were administered either vehicle, tipifarnib (80 mg/kg PO BID), a second active agent, or a combination of tipifarnib and a second active agent. The second agent was either the alkylating agent cisplatin (3 mg/kg IP QW), the CDK inhibitor palbociclib (35 mg/kg PO QD), or the EGFR inhibitor cetuximab (1 mg/mouse IP QW).

Figure 8A:
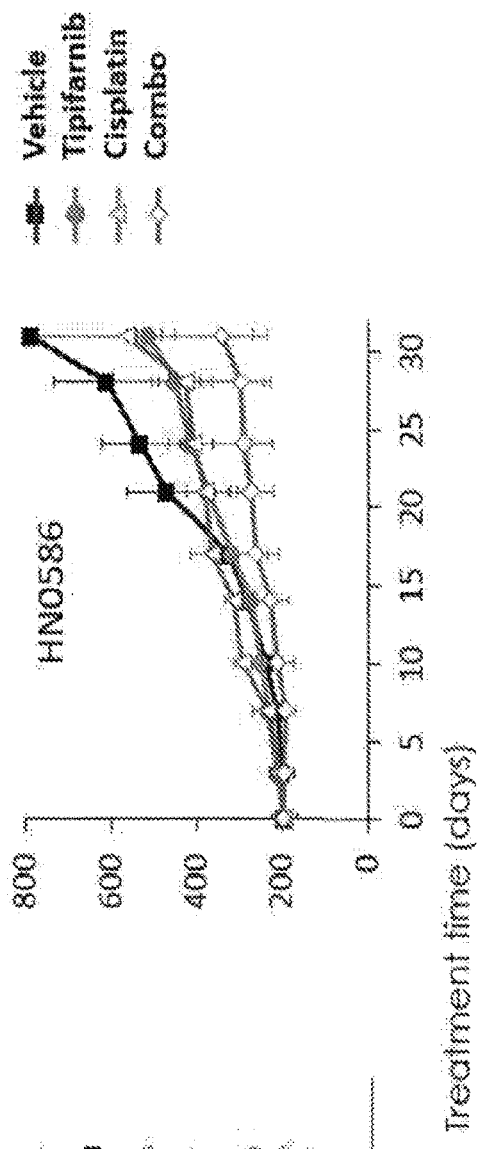
FIGS. 8A-8D. Combination treatment of tipifarnib and a second agent (cisplatin) inhibited tumor growth in HNSCC PDX Models HN3792 (FIG. 8A), HN0586 (FIG. 8B), HN2576 (FIG. 8C), and HN3067 (FIG. 8D), wherein the models have high H-Ras expression and/or high H/N+K Ratios, and figure showing tumor growth curves of mice treated with vehicle, tipifarnib, cisplatin, or combination therapy with both agents in the respective models.
Figure 8B:
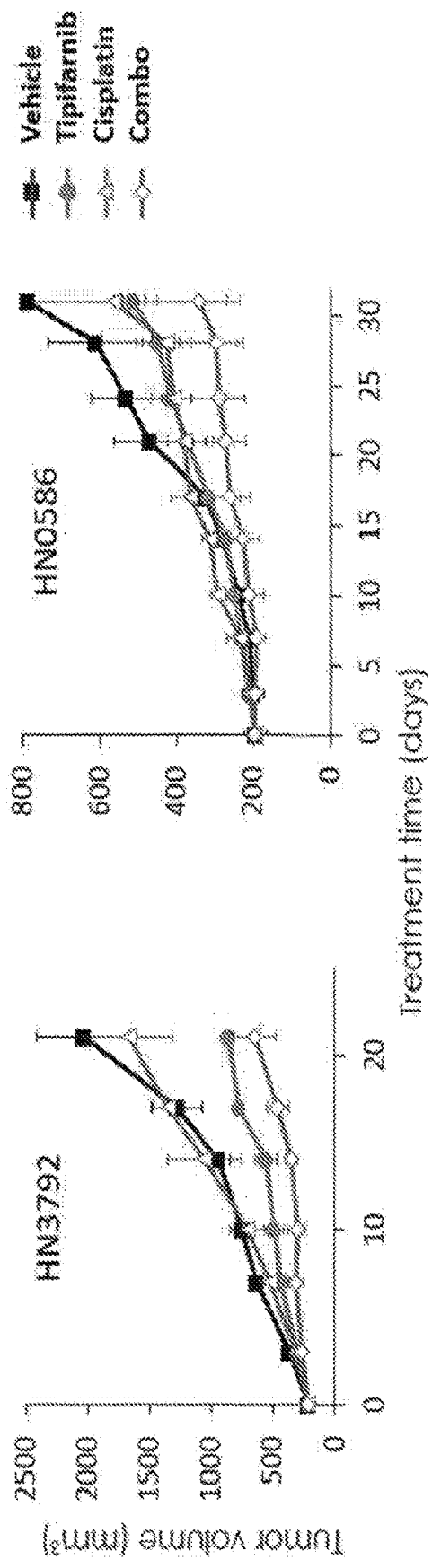
Figure 8C:
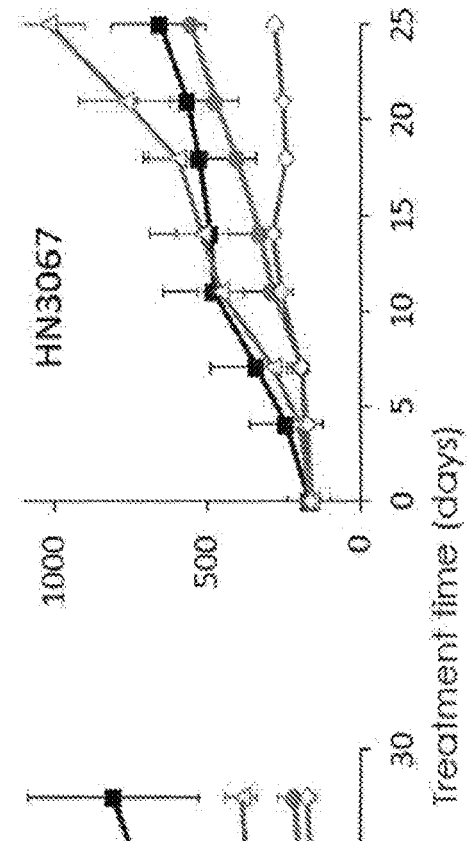
Figure 8D:
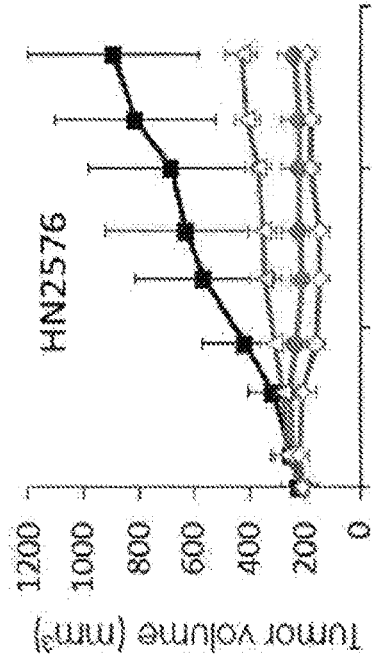

Cisplatin monotherapy was inactive in models HN3792, HN3067, and HN3776 (FIGS. 8A, 8D, and 9C, respectively) and had activity in models HN0586, HN2576, HN2594, HN3461, and HN3474 (FIGS. 8B-8C, 9A-9B, and 9D, respectively), relative to vehicle. Tipifarnib monotherapy had activity in each of the models (FIGS. 8A-8D and 9A-9D) and induced tumor regression in one model (FIG. 8C), relative to vehicle. When cisplatin was combined with tipifarnib, it resulted in further inhibition of tumor growth as compared to tipifarnib alone in models where cisplatin monotherapy had shown activity (FIGS. 8B-8C and 9A). Additionally, in those models where cisplatin monotherapy was inactive, the combination therapy increased the activity relative the tipifarnib monotherapy (FIGS. 8A, 8D, 9A, and 9C). As such, tipifarnib not only directly inhibited tumor growth in HNSCC having high H-Ras expression (FIGS. 8A-8D and 9A-9D), but also sensitized the tumor to cisplatin treatments (FIGS. 8A-8D, 9A, and 9C), even where the tumor was shown to have no sensitivity to cisplatin (FIGS. 8A, 8D, and 9C).

Figures 10A, 10B, 10C, 10D:
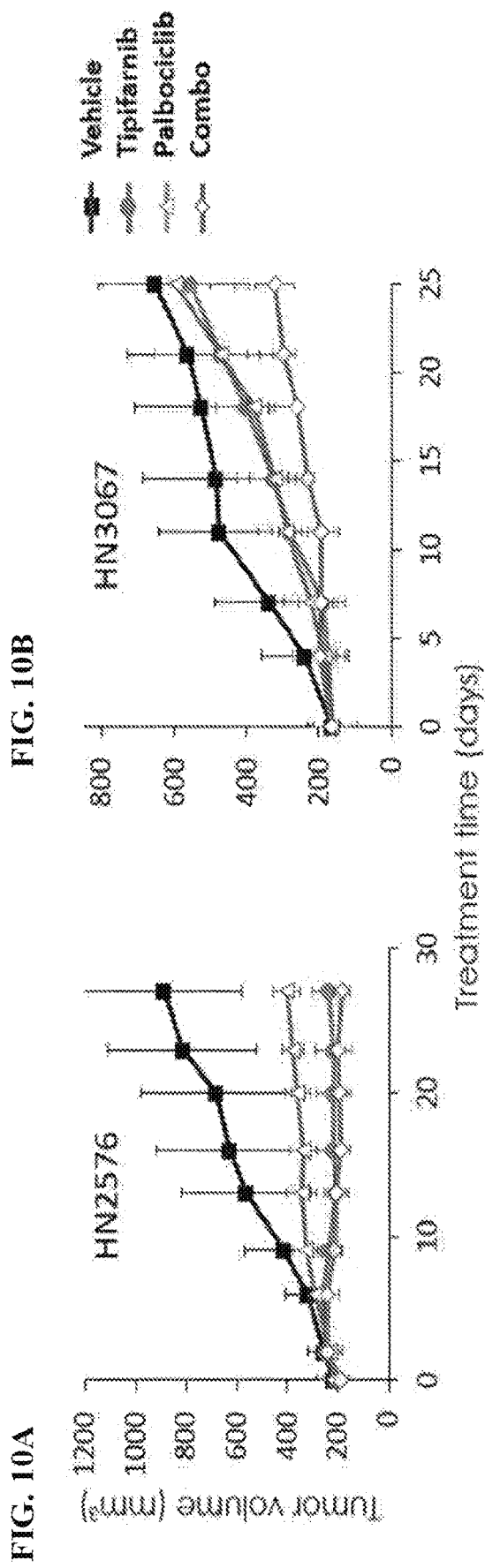
FIGS. 10A-10D. Combination treatment of tipifarnib and a second agent (palbociclib) inhibited tumor growth in HNSCC PDX Models HN2576 (FIG. 10A), HN3067 (FIG. 10B), HN2594 (FIG. 10C), and HN3679 (FIG. 10D), wherein the models have high H-Ras expression and/or high H/N+K Ratios, and figure showing tumor growth curves of mice treated with vehicle, tipifarnib, palbociclib, or combination therapy with both agents in the respective models.

Palbociclib monotherapy had activity in models HN2576, HN2594, and HN3679 (FIGS. 10A and 10C-10D, respectively), and had moderate activity in model HN3067 (FIG. 10B), relative to vehicle. Tipifarnib monotherapy had activity in models HN2576, HN2594, and HN3679 (FIGS. 10A and 10C-10D, respectively), induced tumor regression in one model (FIG. 10A), and had moderate activity in model HN3067 (FIG. 10B), relative to vehicle. When palbociclib was combined with tipifarnib, it resulted in further inhibition of tumor growth where palbociclib monotherapy had shown activity (FIGS. 10A-10D), and even increased inhibition of tumor growth in the model where palbociclib monotherapy was only moderately active (FIG. 10B), relative to tipifarnib monotherapy in said models. As such, tipifarnib not only directly inhibited tumor growth in HNSCC having high H-Ras expression (FIGS. 10A-10D), but also sensitized the tumor to palbociclib treatments (FIGS. 10A-10D), even where the tumor was shown to have moderate sensitivity to palbociclib (FIG. 10B).

Cetuximab monotherapy had high activity in models HN2576, HN3067, and HN3679 (FIGS. 11A-11B and 11D, respectively), and had activity in model HN2594 (FIG. 11C), relative to vehicle. Tipifarnib monotherapy had high activity in models HN2576 and HN3679 (FIGS. 11A and 11D, respectively), induced tumor regression in one model (FIG. 11A), and had activity in models HN3067 and HN2594 (FIG. 11B-11C, respectively), relative to vehicle. When cetuximab was combined with tipifarnib, it resulted in further inhibition of tumor growth where cetuximab monotherapy had shown activity (FIGS. 11B-11C), relative to cetuximab monotherapy or relative to tipifarnib monotherapy in said models. As such, tipifarnib not only directly inhibited tumor growth in HNSCC having high H-Ras expression (FIGS. 11A-11D), but also increased the sensitivity of the tumor to cetuximab treatments (FIGS. 11B-11C).

Example VI

Effect of Tipifarnib and Second Therapies in HNSCC with High H-Ras Expression or Mutant H-Ras Expression As described in Example I, mice were inoculated subcutaneously on the flank with PDX HNSCC models HN2594 and HN2576, with each model having high H-Ras expression level and/or high H/N+K Ratios (as detailed in Table 1), and with PDX HNSCC model HN1420, having a mutation that is or comprises a modification in a codon of the mutant H-Ras gene encoding an amino acid at the specified position to provide the resulting mutated H-Ras protein HRAS A146P. After tumor development, mice were administered either vehicle, tipifarnib (at a reduced dosing of 60 mg/kg PO BID), a second active agent, or a combination of tipifarnib and a second active agent. The second agent was either the PI3K-α inhibitor BYL719 (50 mg/kg PO QD) (FIGS. 12A-12C), the AKT inhibitor GSK2141795 (30 mg/kg PO QD) (FIGS. 13A-13C), or the MTORC 1/2 inhibitor INK-128 (0.3 mg/kg PO QD) (FIGS. 14A-14C).

PI3K-α inhibitor BYL719 monotherapy and tipifarnib monotherapy had activity in high H-Ras expression level models HN2594 and HN2576 (FIGS. 12A-12B), and mutated H-Ras model HN1420 (FIG. 12C), relative to vehicle. Tipifarnib monotherapy induced tumor regression in one model (FIG. 12C), relative to vehicle. When PI3K-α inhibitor BYL719 was combined with tipifarnib, it resulted in further inhibition of tumor growth in high H-Ras expression level models HN2594 and HN2576 (FIGS. 12A-12B) and mutated H-Ras model HN1420 (FIG. 12C), relative to tipifarnib monotherapy or relative to PI3K-α inhibitor BYL719 monotherapy in said models. The combination therapy induced tumor regression in each of the models, relative to vehicle (FIGS. 12A-12C). As such, tipifarnib not only directly inhibited tumor growth in HNSCC having high H-Ras expression (FIGS. 12A-12B) or mutated H-Ras expression (FIG. 12C), but also increased the sensitivity of the tumor to PI3K-α inhibitor BYL719 treatments in high H-Ras expression level models (FIGS. 12A-12B) and a mutated H-Ras model (FIG. 12C).

Figure 13A:
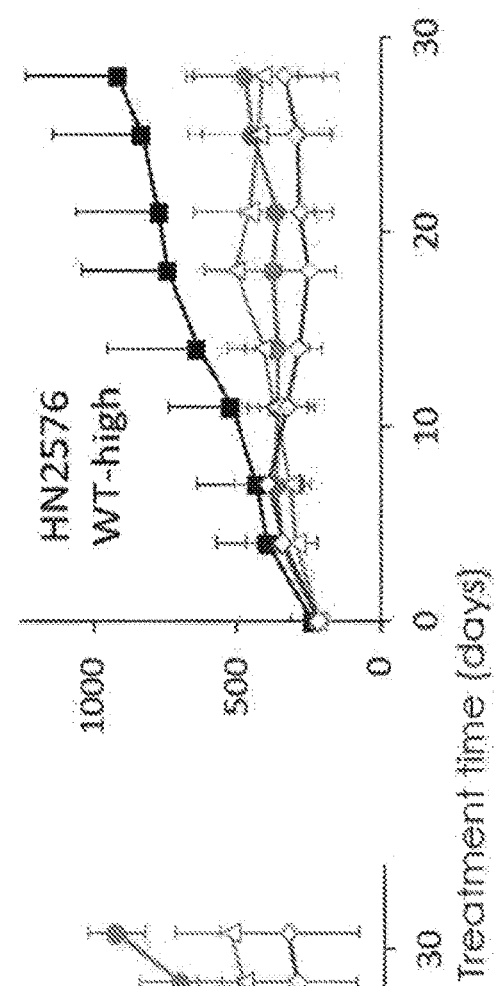
FIGS. 13A-13C. Combination treatment of tipifarnib and a second agent (AKT inhibitor GSK2141795) inhibited tumor growth in HNSCC PDX Models HN2594 (FIG. 13A) and HN2576 (FIG. 13B) (wherein both models have high H-Ras expression and/or high H/N+K Ratios), and in PDX HNSCC model HN1420 (FIG. 13C) having mutated H-Ras gene expression (at codon for HRAS A146P), wherein the FIGS. 13A-13C show tumor growth curves of mice treated with vehicle, tipifarnib, GSK2141795, or combination therapy with both agents in the respective models.
Figure 13B:
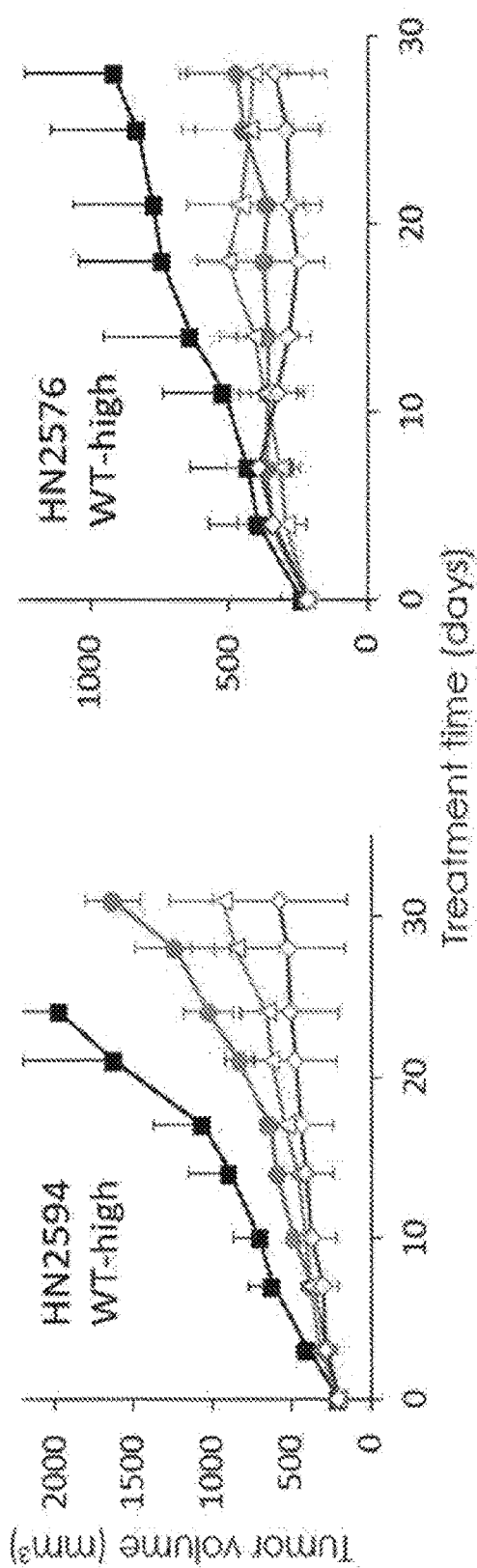
Figure 13C:
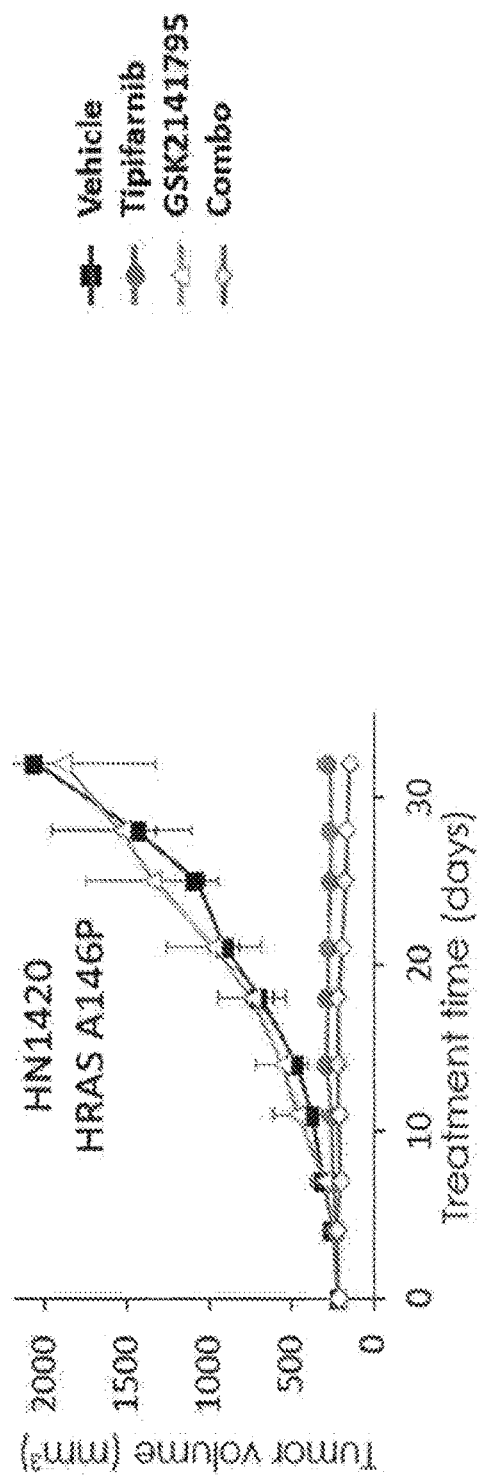

AKT inhibitor GSK2141795 monotherapy had activity in high H-Ras expression level models HN2594 and HN2576 (FIGS. 13A-13B), but was inactive in the mutated H-Ras model HN1420 (FIG. 13C), relative to vehicle. Tipifarnib monotherapy had activity in high H-Ras expression level models HN2594 and HN2576 (FIGS. 13A-13B) and the mutated H-Ras model HN1420 (FIG. 13C), relative to vehicle, induced tumor regression in one model (FIG. 13C), relative to vehicle. When AKT inhibitor GSK2141795 was combined with tipifarnib, it resulted in further inhibition of tumor growth in high H-Ras expression level models HN2594 and HN2576 (FIGS. 13A-13B) and mutated H-Ras model HN1420 (FIG. 13C), relative to tipifarnib monotherapy or relative to AKT inhibitor GSK2141795 monotherapy in said models. The combination therapy induced tumor regression in high H-Ras expression level model HN2576 (FIG. 13B) and mutated H-Ras model HN1420 (FIG. 13C), relative to vehicle. As such, tipifarnib not only directly inhibited tumor growth in HNSCC having high H-Ras expression (FIGS. 13A-13B) or mutated H-Ras expression (FIG. 13C), it increased the sensitivity of the tumor to AKT inhibitor GSK2141795 treatments in high H-Ras expression level models (FIGS. 13A-13B). The combination with tipifarnib also sensitized the tumor to AKT inhibitor GSK2141795 treatments where the tumor was shown to have no sensitivity to AKT inhibitor GSK2141795 in a mutated H-Ras model (FIG. 13C).

MTORC 1/2 inhibitor INK-128 monotherapy and tipifarnib monotherapy had activity in high H-Ras expression level models HN2594 and HN2576 (FIGS. 14A-14B), and mutated H-Ras model HN1420 (FIG. 14C), relative to vehicle. Tipifarnib monotherapy induced tumor regression in one model (FIG. 14C), relative to vehicle. When MTORC 1/2 inhibitor INK-128 was combined with tipifarnib, it resulted in further inhibition of tumor growth in high H-Ras expression level models HN2594 and HN2576 (FIGS. 14A-14B) and mutated H-Ras model HN1420 (FIG. 14C), relative to tipifarnib monotherapy or relative to MTORC 1/2 inhibitor INK-128 monotherapy in said models. The combination therapy induced tumor regression in each of the models, relative to vehicle (FIGS. 14A-14C). As such, tipifarnib not only directly inhibited tumor growth in HNSCC having high H-Ras expression (FIGS. 14A-14B) or mutated H-Ras expression (FIG. 14C), but also increased the sensitivity of the tumor to MTORC 1/2 inhibitor INK-128 treatments in high H-Ras expression level models (FIGS. 14A-14B) and a mutated H-Ras model (FIG. 14C).

Example VII

Effect of Tipifarnib and Second Therapies in HNSCC with Mutant H-Ras Expression

As described in Example I, mice were inoculated subcutaneously on the flank with PDX HNSCC models HN1420 (FIG. 15A), HN2581 (FIG. 15B), HN2579 (FIG. 15C), and HN3504 (FIG. 15D), having a mutation that is or comprises a modification in a codon of the mutant H-Ras gene encoding an amino acid at the specified position to provide the resulting mutated H-Ras protein HRAS A146P, HRAS G13C, HRAS G12S, and HRAS K117L, respectively. After tumor development, mice were administered either vehicle, tipifarnib (at a reduced dosing of 60 mg/kg PO BID), a second active agent, or a combination of tipifarnib and a second active agent. The second agent was PI3K-α inhibitor BYL719 (50 mg/kg PO QD).

PI3K-α inhibitor BYL719 monotherapy had activity in each of the mutated H-Ras models (FIGS. 15A-15D), relative to vehicle. Tipifarnib monotherapy had activity in each of the mutated H-Ras models (FIGS. 15A-15D), and induced tumor regression in two models (FIGS. 15A-15B), relative to vehicle. When PI3K-α inhibitor BYL719 was combined with tipifarnib, it resulted in further inhibition of tumor growth in each of the mutated H-Ras models (FIGS. 15A-15D), relative to tipifarnib monotherapy or relative to PI3K-α inhibitor BYL719 monotherapy in said models. The combination therapy induced tumor regression in each of the models, relative to vehicle (FIGS. 15A-15D). As such, tipifarnib not only directly inhibited tumor growth in mutated H-Ras expression HNSCC models (FIGS. 15A-15D), but also increased the sensitivity of the tumor to PI3K-α inhibitor BYL719 treatments in mutated H-Ras models (FIGS. 15A-15D).

Example VIII

Effect of Tipifarnib and Second Therapies in HNSCC with Mutant H-Ras Expression and with or without Co-Mutations in PIK3CA As described in Example I, mice were inoculated subcutaneously on the flank with PDX HNSCC models having high H-Ras expression levels and having wild type PIK3CA expression levels HN3067 (FIG. 16A) and HN3411 (FIG. 16C), or having high H-Ras expression levels and having mutated PIK3CA expression levels HN2593 (FIG. 16B) and HN3690 (FIG. 16D), wherein the mutation is or comprises a modification in a codon of the mutant PIK3CA gene (referred to as PIK3CA$^{G118D}$ and PIK3CA$^{E545K}$ in FIGS. 16B and 16D, respectively) encoding an amino acid at the specified position to provide the resulting mutated PI3K-α protein PI3K-α G118D and PI3K-α E545K, respectively. After tumor development, mice were administered either vehicle, tipifarnib (at a reduced dosing of 60 mg/kg PO BID), a second active agent, or a combination of tipifarnib and a second active agent. The second agent was PI3K-α inhibitor BYL719 (50 mg/kg PO QD).

PI3K-α inhibitor BYL719 monotherapy and tipifarnib monotherapy had activity in the high H-Ras expression/wild type PIK3CA expression models (FIGS. 16A and 16C), and in the high H-Ras expression/mutated PIK3CA expression models (FIGS. 16B and 16D), relative to vehicle. When PI3K-α inhibitor BYL719 was combined with tipifarnib, it resulted in further inhibition of tumor growth in each of the models (FIGS. 16A-16D), relative to tipifarnib monotherapy or relative to PI3K-α inhibitor BYL719 monotherapy in said models. The combination therapy induced tumor regression in one of the high H-Ras expression/wild type PIK3CA expression models, relative to vehicle (FIG. 16A). As such, tipifarnib not only directly inhibited tumor growth in the high H-Ras expression/wild type PIK3CA expression models (FIGS. 16A and 16C) and in the high H-Ras expression/ mutated PIK3CA expression models (FIGS. 16B and 16D), but also increased the sensitivity of the tumor to PI3K-α inhibitor BYL719 treatments in each of these models (FIGS. 16A-16D).

Example IX

TCGA PanCancer Atlas Data Analysis

The H-Ras expression levels were surveyed and evaluated based on the data available from the studies within the database TCGA PanCancer Atlas. In particular, the H-Ras expression levels were evaluated within two subsets of carcinomas: squamous cell carcinomas (HNSCC, LSCC, and UC) and adenocaarcinomas (colorectal cancer ("CRC"), pancreatic ductal adenocarcinoma ("PDAC"), and lung adenocarcinoma ("LUAD")). An H-Ras Expression RNAseq V2 (log) value of 11 was set as the cutoff for H-Ras overexpression. A summary of the data is provided in FIG. 17 and in Table 3 below.

TABLE 3

H-Ras mutant expression levels in Squamous Cell Carcinomas and within Adenocaarcinomas

| Carcinoma | Mean | SEM | z-score* | # > Cutoff | Total | % High |
|---|---|---|---|---|---|---|
| HNSCC | 10.63 | 0.04 | 24.96 | 146 | 482 | 30.3 |
| LSCC | 9.96 | 0.03 | 19.75 | 39 | 461 | 8.5 |
| UC | 10.31 | 0.04 | 21.56 | 78 | 306 | 25.5 |
| CRC | 8.92 | 0.03 | NA | 1 | 520 | 0.2 |
| PDAC | 9.30 | 0.05 | 6.37 | 2 | 163 | 1.2 |
| LUAD | 8.86 | 0.03 | 1.13 | 1 | 498 | 0.2 |

*vs. CRC.

Figure 17:
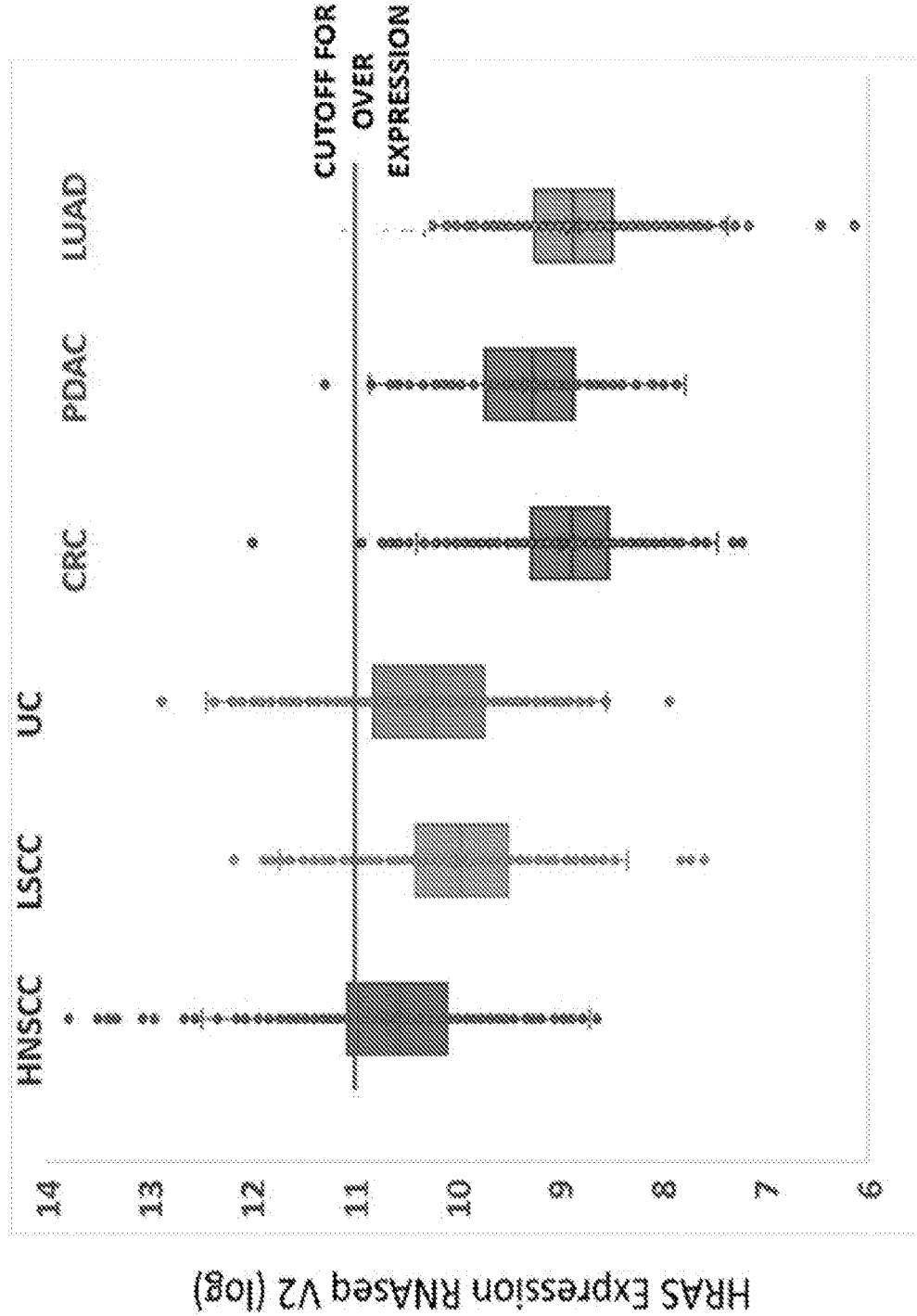
FIG. 17. H-Ras expression levels in patients having squamous cell carcinomas (HNSCC, LSCC, and UC) and adenocaarcinomas (CRC, PDAC, and LUAD), according to data available within the database TCGA PanCancer Atlas.

As shown in FIG. 17 and as detailed in Table 3, the H-Ras gene expression levels observed in patients having squamous cell carcinomas (HNSCC, LSCC, and UC) are generally higher than those in patients having colorectal, pancreatic ductal or lung adenocarcinomas (CRC, PDAC, and LUAD), relative to the cutoff for H-Ras overexpression, in terms of mean average of expression levels and the number (or percentage) above the cutoff level. For example, according to the data available from the studies within the database TCGA PanCancer Atlas, the H-Ras gene is overexpressed in 30.3% of HNSCC patients, in 8.5% of LSCC patients, and in 25.5% of UC patients, compared to 0.2%, 1.2%, and 0.2% of CRC, PDAC, and LUAD patients, respectively.

Figure 18:
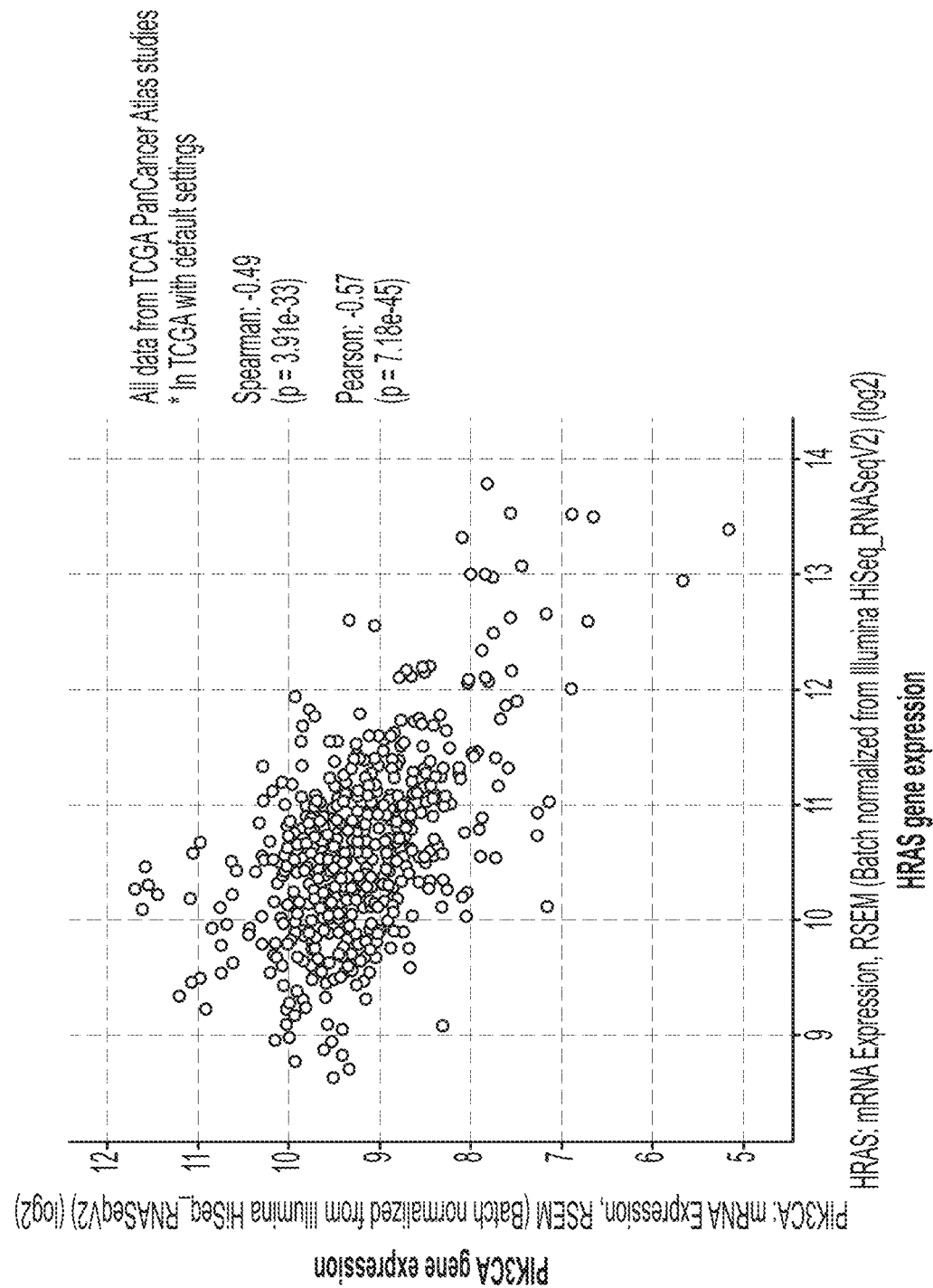
FIG. 18. Correlation between H-Ras gene expression levels and PIK3CA gene expression levels in HNSCC patients, according to data available within the database TCGA PanCancer Atlas.

Within the HNSCC patient population, the data available from the studies within the database TCGA PanCancer Atlas was further evaluated based on both the H-Ras gene expression levels and the PIK3CA gene expression levels (using the TCGA default settings), with the H-Ras gene and PIK3CA gene expression levels provided in mRNA Expression, RSEM (Batch normalized from Illumina HiSeq_R-NASeqV2) (log 2), and is shown FIG. 18 (with a Spearman value −0.49 (p=3.91e-33), and a Pearson value −0.57 (p=7.18e-45)). A summary of this data is provided below in Table 4.

TABLE 4

H-Ras and PIK3CA gene Expression Levels in HNSCC Patients

| Gene 1 | Gene 2 | Spearman | p-value |
|---|---|---|---|
| PIK3CA | HRAS | −0.49 | 3.91E−33 |
| PIK3R1 | HRAS | −0.33 | 3.77e−14 |
| PIK3CA | KRAS | 0.49 | 1.98E−30 |
| PIK3R1 | KRAS | 0.22 | 1.01e−6 |
| HRAS | AKT1 | −0.05 | 2.96E−01 |
| HRAS | AKT2 | −0.01 | 7.45E−01 |
| HRAS | MTOR | −0.35 | 2.48E−15 |

As shown in FIG. 18 and as detailed in Table 4, from the TCGA data available, there appears to be an inverse relationship between H-Ras gene expression and PIK3CA gene expression within the HNSCC patient population. For example, as H-Ras gene expression levels increase there appears to be a decrease in PIK3CA gene expression levels, indicating that there may be a compensatory relationship between H-Ras gene expression and PIK3CA gene expression within the HNSCC patient population. Additionally, from the data provided in Table 4, there appears to be a modest inverse relationship between H-Ras gene expression and MTOR gene expression, indicating that there may be a modest compensatory relationship between H-Ras gene expression and MTOR gene expression within the HNSCC patient population. In contrast, from the data provided in Table 4, there appears to be a positive correlation within the HNSCC patient population between KRAS gene expression and PIK3CA gene expression, suggesting that their expressions may provide a redundant function. From the data provided in Table 4, there does not appear to be a correlation between H-Ras gene expression and AKT gene expression within the HNSCC patient population.

Figures 19A, 19B:
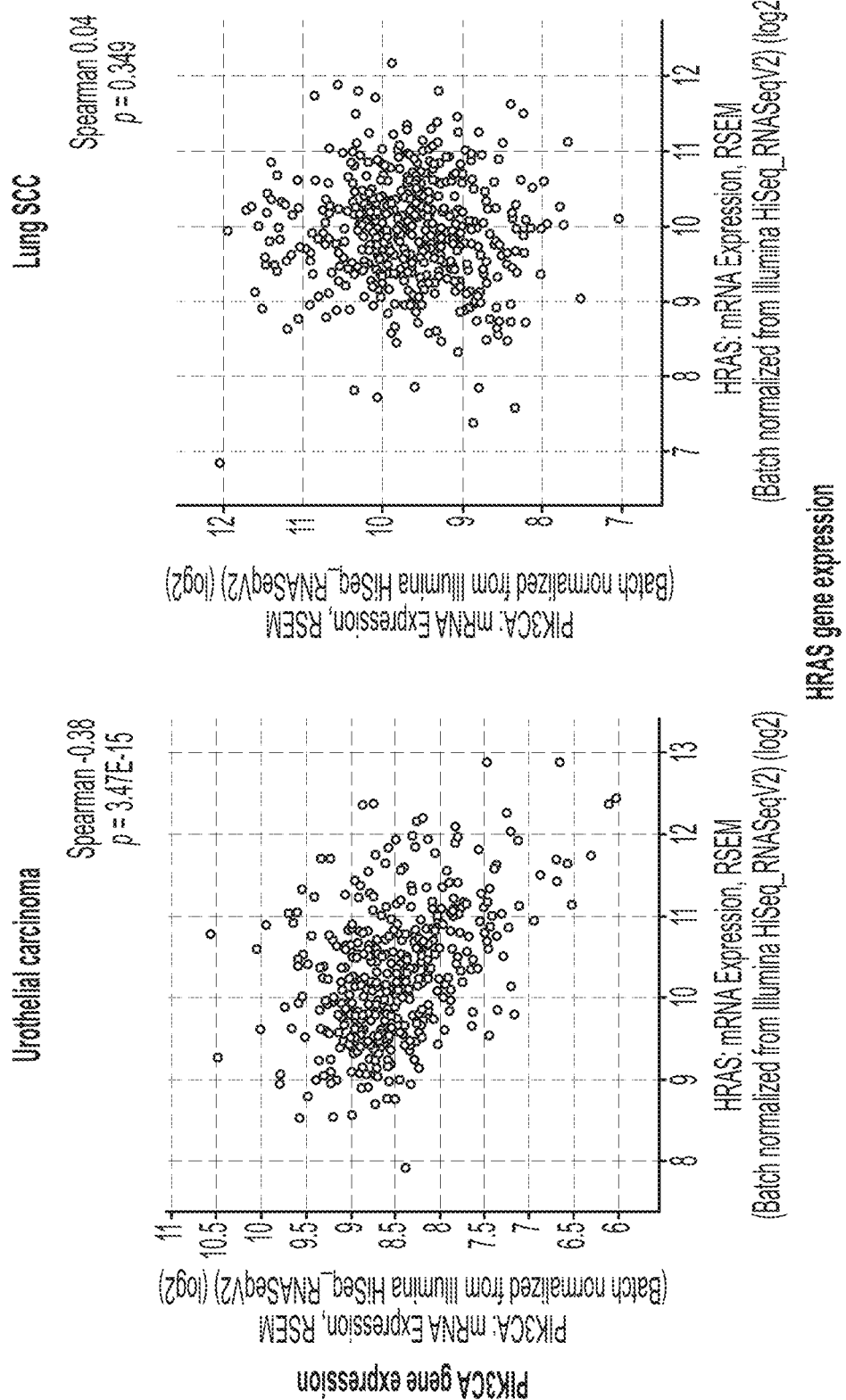
FIGS. 19A-19B. Correlation between H-Ras gene expression levels and PIK3CA gene expression levels in UC patients (FIG. 19A) and in LSCC patients (FIG. 19B), according to data available within the database TCGA PanCancer Atlas.

The data regarding H-Ras gene expression levels and the PIK3CA gene expression levels available within the database TCGA PanCancer Atlas (using the TCGA default settings) was further evaluated based on the type of squamous cell carcinoma, specifically UC (FIG. 19A) and LSCC (FIG. 19B). In particular, the relationship between the H-Ras gene expression levels and the PIK3CA gene expression levels for UC is shown in FIG. 19A (with a Spearman value −0.38; p=3.47e-15) and for LSCC is shown in FIG. 19B (with a Spearman value −0.04; p=0.349). This data indicates that there may be more of a compensatory relationship (an inverse relationship) between H-Ras gene expression and PIK3CA gene expression in patients having UC (FIG. 19A) than those having LSCC (FIG. 19B). As such, UC patients having high H-Ras expression may be more likely to respond and benefit from a combination of tipifarnib with a PI3K-α inhibitor, relative to LSCC patients.

Figure 20:
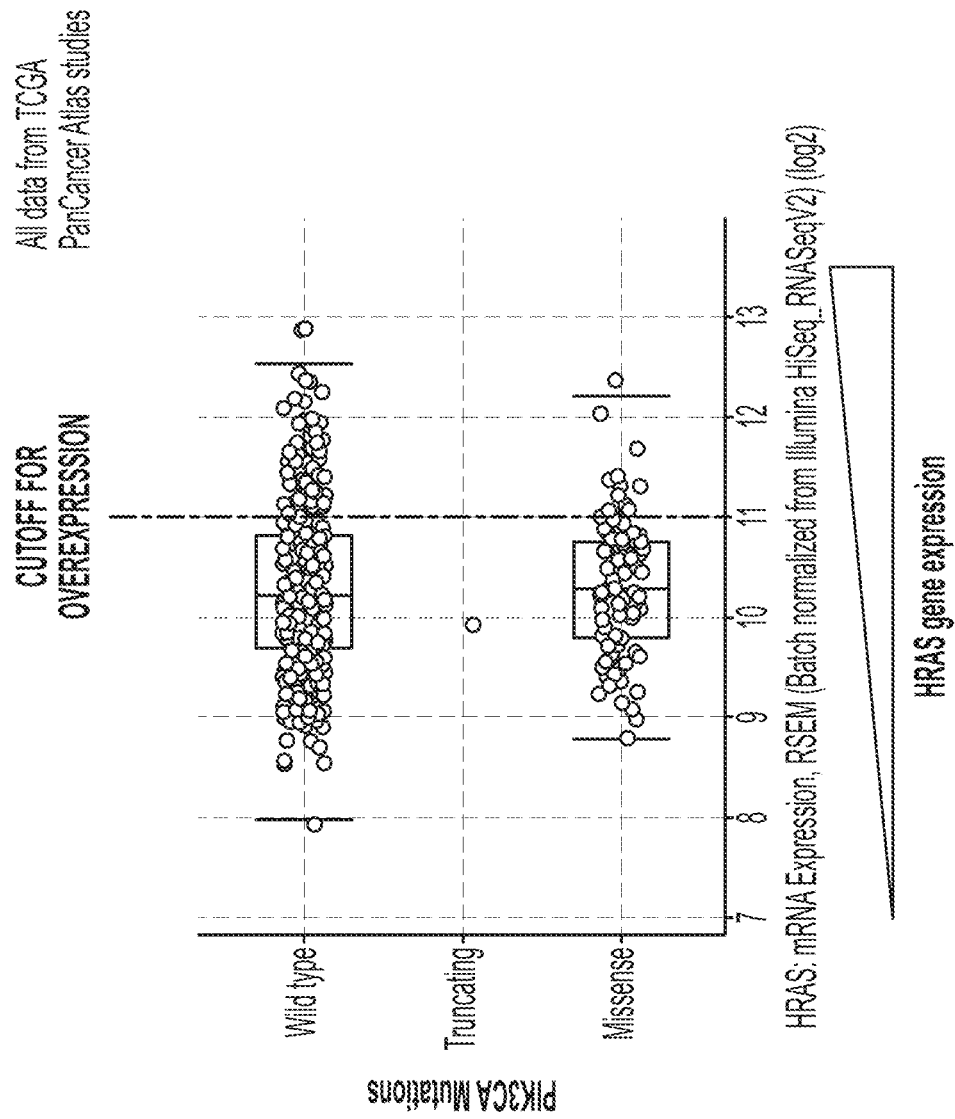
FIG. 20. Distribution of H-Ras expression levels within UC patients having wild type PIK3CA gene expression compared to the distribution having particular types of mutated forms of the PIK3CA gene expressed, according to data available within the database TCGA PanCancer Atlas.

The data regarding H-Ras gene expression levels relative to wild type and various mutated forms of PIK3CA gene expressions was further evaluated from the data available within the database TCGA PanCancer Atlas within the UC patient population. In particular, for patients having UC, according to the TCGA PanCancer Atlas data, the distribution of H-Ras expression levels within UC patients having wild type PIK3CA gene expression compared to the distribution having particular types of mutated forms of the PIK3CA gene expressed (such as a truncated or missense forms), appear similarly distributed relative to the cutoff value for H-Ras overexpression (set at an H-Ras Expression RNAseq V2 (log) value of 11) (FIG. 20). As such, UC patients having high H-Ras expression and having either wild type or mutated PIK3CA gene expression, may benefit from a combination of tipifarnib with a PI3K-α inhibitor, particularly in those UC patients having a tumor that is sensitive to PI3K-α inhibitor treatment.

Example X

Individualized Treatment Decisions for HNSCC Patients

The following procedures can be taken to determine whether a HNSCC patient is suitable for an FTI treatment, such as a tipifarnib treatment.

A tumor biopsy is collected from the patient before treatment. Total RNA is extracted from cell samples using the Trizol Kit (Qiagen, Santa Clarita, Calif.). RNA quality is determined by assessing the presence of ribosomal bands on an Agilent Bioanalyzer (Agilent, Palo Alto, Calif.). Good-quality samples are further processed for microarray analysis.

For each sample, 1 g total RNA (as assessed by OD260) is reverse transcribed using the High Capacity cDNA Reverse Transcription kit (Applied Biosystems, Foster City, Calif.) according to the manufacturer's instructions. Samples can then be incubated at 25° C. for 10 minutes and then 37° C. for 30 minutes for optimum RNA conversion. QPCR is performed using the ABI Prism 7900HT sequence detection system (Applied Biosystems) with all samples run in triplicate. Each reaction contains 5 µL Taqman Universal PCR Master Mix containing uracil-N-glycosylase (Applied Biosystems), 4.5 µL, cDNA template, and 0.5 µL of 20× Assay on Demand Gene Expression Assay Mix (Applied Biosystems) or 9 pmol both forward and reverse primer and 2.5 pmol probe in a total reaction volume of 10 µL. All primer and fluorescein amidite (FAM) fluorogenic probe sets are chosen to generate amplicons less than 100 nucleotides, allowing for amplification of transcripts from degraded RNA samples. Primers and probes are designed for specific amplification of the h-ras, k-ras and n-ras genes. All primer sets span exon boundaries and thus specifically amplify mRNA transcripts and not genomic DNA.

The H-Ras, K-Ras and N-Ras expression levels are then calculated using methods known in the art. The raw Ct values are normalized by subtracting the mean Ct from the sample set, dividing by the standard deviation, and then calculating the difference of the normalized Ct values of each gene. The median H-Ras expression level, or a cutoff percentile (e.g. the top 30%) of the H-Ras expression in a HNSCC patient population of appropriate size can be used as the reference expression level, and the median H/K+N ratio, or a cutoff percentile (e.g. the top 30%) of the H/K+N ratio in a HNSCC patient population of appropriate size can be used as the reference ratio. If the H-Ras expression of the HNSCC patient is determined to be higher than the reference level, or the H/K+N ratio in the HNSCC patient is determined to be higher than the reference ratio, and that the patient is not otherwise prevented from receiving a tipifarnib treatment, a tipifarnib treatment is prescribed. On the other hand, if the H-Ras expression of the HNSCC patient is determined to be no more than the reference level, and the H/K+N ratio in the HNSCC patient is determined to be no more than the reference ratio, a tipifarnib treatment is not recommended.

If a tipifarnib treatment is prescribed to the HNSCC patient, the HNSCC patient can simultaneously receive another treatment, such as cetuximab, cisplatin, or palbociclib, as deemed fit by an oncologist.

Throughout this application various publications have been referenced. The disclosures of these publications in their entireties, including GenBank and GI number publications, are hereby incorporated by reference in this application in order to more fully describe the state of the art to which this disclosure pertains. Although the invention has been described with reference to the examples provided above, it should be understood that various modifications can be made without departing from the spirit of the invention.

We claim:

1. A method of treating wild-type H-Ras-overexpressing head and neck squamous cell carcinoma (HNSCC) in a subject, comprising administering a therapeutically effective amount of tipifarnib and a therapeutically effective amount of PI3K-α inhibitor BYL719 to the subject having wild-type H-Ras-overexpressing HNSCC.

2. The method of claim 1, wherein the HNSCC has wild-type H-Ras overexpression that is greater than a median expression level of wild-type H-Ras in corresponding tissue in a population of healthy subjects.

3. The method of claim 1, wherein said HNSCC is HNSCC of the trachea, HNSCC of the maxilla, or HNSCC of the oral cavity.

4. The method of claim 1, wherein said HNSCC is human papillomavirus (HPV)-negative.

5. The method of claim 1, wherein said HNSCC is metastatic.

6. The method of claim 1, wherein said HNSCC is at an advanced stage, relapsed, or refractory.

7. The method of claim 1, wherein the tipifarnib is administered twice a day.

8. The method of claim 1, wherein the tipifarnib is administered at a dose of 100-1200 mg twice a day.

9. The method of claim 1, wherein the tipifarnib is administered on days 1-7 and 15-21 of a 28-day treatment cycle, administered on days 1-21 of a 28-day treatment cycle, or administered on days 1-7 of a 28-day treatment cycle.

10. The method of claim 9, wherein the tipifarnib is administered for at least 1 cycle.

11. The method of claim 1, wherein the tipifarnib is administered before, during, or after radiation.

12. The method of claim 1, wherein the HNSCC has wild-type H-Ras overexpression that is greater than a median expression level of wild-type H-Ras in corresponding tissue in a population of HNSCC subjects.

13. The method of claim 1, wherein the HNSCC has a PIK3CA gene mutation.

14. The method of claim 13, wherein the HNSCC has wild-type H-Ras overexpression that is greater than a median expression level of wild-type H-Ras in corresponding tissue in a population of healthy subjects.

15. The method of claim 13, wherein the HNSCC has wild-type H-Ras overexpression that is greater than a median expression level of wild-type H-Ras in corresponding tissue in a population of HNSCC subjects.

16. The method of claim 13, wherein said HNSCC is at an advanced stage, relapsed, or refractory.

17. The method of claim 13, wherein the tipifarnib is administered at a dose of 100-1200 mg twice a day.

18. The method of claim 13, wherein the tipifarnib is administered on days 1-7 and 15-21 of a 28-day treatment cycle, administered on days 1-21 of a 28-day treatment cycle, or administered on days 1-7 of a 28-day treatment cycle.

19. The method of claim 1, wherein the HNSCC has an amplification of PIK3CA gene.

20. The method of claim 19, wherein the HNSCC has wild-type H-Ras overexpression that is greater than a median expression level of wild-type H-Ras in corresponding tissue in a population of healthy subjects.

21. The method of claim 19, wherein the HNSCC has wild-type H-Ras overexpression that is greater than a median expression level of wild-type H-Ras in corresponding tissue in a population of HNSCC subjects.

22. The method of claim 19, wherein said HNSCC is at an advanced stage, relapsed, or refractory.

23. The method of claim 19, wherein the tipifarnib is administered at a dose of 100-1200 mg twice a day.

24. The method of claim 19, wherein the tipifarnib is administered on days 1-7 and 15-21 of a 28-day treatment cycle, administered on days 1-21 of a 28-day treatment cycle, or administered on days 1-7 of a 28-day treatment cycle.

25. The method of claim 1, wherein the wild-type H-Ras overexpressing HNSCC comprises increased transcription of wild-type H-Ras or increased translation of wild-type H-Ras.

26. The method of claim 8, wherein the tipifarnib is administered on days 1-7 and 15-21 of a 28-day treatment cycle.

27. The method of claim 8, wherein the tipifarnib is administered on days 1-21 of a 28-day treatment cycle.

28. The method of claim 8, wherein the tipifarnib is administered on days 1-7 of a 28-day treatment cycle.

29. The method of claim 1, wherein the tipifarnib is administered at a dose of 300 mg, 400 mg, 500 mg, 600 mg, 700 mg, 800 mg, 900 mg, 1000 mg, 1100 mg, or 1200 mg twice a day.

30. The method of claim 29, wherein the tipifarnib is administered on days 1-7 and 15-21 of a 28-day treatment cycle.

31. The method of claim 29, wherein the tipifarnib is administered on days 1-21 of a 28-day treatment cycle.

32. The method of claim 29, wherein the tipifarnib is administered on days 1-7 of a 28-day treatment cycle.

33. The method of claim 17, wherein the tipifarnib is administered on days 1-7 and 15-21 of a 28-day treatment cycle.

34. The method of claim 17, wherein the tipifarnib is administered on days 1-21 of a 28-day treatment cycle.

35. The method of claim 17, wherein the tipifarnib is administered on days 1-7 of a 28-day treatment cycle.

36. The method of claim 13, wherein the tipifarnib is administered at a dose of 300 mg, 400 mg, 500 mg, 600 mg, 700 mg, 800 mg, 900 mg, 1000 mg, 1100 mg, or 1200 mg twice a day.

37. The method of claim 36, wherein the tipifarnib is administered on days 1-7 and 15-21 of a 28-day treatment cycle.

38. The method of claim 36, wherein the tipifarnib is administered on days 1-21 of a 28-day treatment cycle.

39. The method of claim 36, wherein the tipifarnib is administered on days 1-7 of a 28-day treatment cycle.

40. The method of claim 13, wherein the wild-type H-Ras overexpressing HNSCC comprises increased transcription of wild-type H-Ras or increased translation of wild-type H-Ras.

41. The method of claim 23, wherein the tipifarnib is administered on days 1-7 and 15-21 of a 28-day treatment cycle.

42. The method of claim 23, wherein the tipifarnib is administered on days 1-21 of a 28-day treatment cycle.

43. The method of claim 23, wherein the tipifarnib is administered on days 1-7 of a 28-day treatment cycle.

44. The method of claim 19, wherein the tipifarnib is administered at a dose of 300 mg, 400 mg, 500 mg, 600 mg, 700 mg, 800 mg, 900 mg, 1000 mg, 1100 mg, or 1200 mg twice a day.

45. The method of claim 44, wherein the tipifarnib is administered on days 1-7 and 15-21 of a 28-day treatment cycle.

46. The method of claim 44, wherein the tipifarnib is administered on days 1-21 of a 28-day treatment cycle.

47. The method of claim 44, wherein the tipifarnib is administered on days 1-7 of a 28-day treatment cycle.

48. The method of claim 19, wherein the wild-type H-Ras overexpressing HNSCC comprises increased transcription of wild-type H-Ras or increased translation of wild-type H-Ras.

49. The method of claim 13, wherein said HNSCC is metastatic.

50. The method of claim 19, wherein said HNSCC is metastatic.

* * * * *